US007081279B2

(12) United States Patent
Kato et al.

(10) Patent No.: US 7,081,279 B2
(45) Date of Patent: *Jul. 25, 2006

(54) ALKENYL COMPOUND HAVING A NEGATIVE Δε VALUE, LIQUID CRYSTAL COMPOSITION, AND LIQUID CRYSTAL DISPLAY DEVICE

(75) Inventors: Takashi Kato, Chiba (JP); Tomoyuki Kondo, Chiba (JP); Henry Bernhardt, Berlin (DE); Shuichi Matsui, Chiba (JP); Hiroyuki Takeuchi, Chiba (JP); Yasuhiro Kubo, Chiba (JP); Fusayuki Takeshita, Chiba (JP); Etsuo Nakagawa, Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/650,765

(22) Filed: Aug. 29, 2003

(65) Prior Publication Data
US 2004/0065866 A1   Apr. 8, 2004

Related U.S. Application Data

(63) Continuation of application No. 09/323,820, filed on Jun. 2, 1999, now Pat. No. 6,692,657.

(30) Foreign Application Priority Data

Jun. 2, 1998    (JP) ................................. 10-169251
Feb. 26, 1999   (JP) ................................. 11-049565

(51) Int. Cl.
C09K 19/34   (2006.01)
C09K 19/30   (2006.01)
C09K 19/32   (2006.01)
C09K 19/12   (2006.01)
C07C 43/225  (2006.01)

(52) U.S. Cl. ............. 428/1.1; 252/299.61; 252/299.62; 252/299.63; 252/299.66; 570/127; 570/129; 570/135; 549/13; 549/356; 549/369

(58) Field of Classification Search .......... 252/299.01, 252/299.63, 299.61, 299.66, 299.62; 428/1.1; 570/127, 129, 135; 549/369, 13, 356, 362
See application file for complete search history.

(56) References Cited

U.S. PATENT DOCUMENTS

| 5,122,295 | A  |   | 6/1992  | Weber et al.    |          |
|-----------|----|---|---------|-----------------|----------|
| 5,599,480 | A  |   | 2/1997  | Tarumi et al.   |          |
| 5,707,547 | A  |   | 1/1998  | Fujimoto et al. |          |
| 6,030,546 | A  | * | 2/2000  | Fujimoto et al. | 252/299.6|
| 6,217,953 | B1 |   | 4/2001  | Heckmeier et al.|          |
| 6,287,650 | B1 |   | 9/2001  | Pauluth et al.  |          |
| 6,348,244 | B1 |   | 2/2002  | Miyazawa        |          |
| 6,399,164 | B1 | * | 6/2002  | Yanai et al.    | 428/1.1  |
| 6,468,608 | B1 | * | 10/2002 | Bremer et al.   | 428/1.1  |
| 6,475,595 | B1 | * | 11/2002 | Bremer et al.   | 428/111  |
| 6,558,758 | B1 | * | 5/2003  | Yanai et al.    | 428/1.1  |
| 6,692,657 | B1 | * | 2/2004  | Kato et al.     | 252/299.63|

FOREIGN PATENT DOCUMENTS

| DE | 42 11 694 A1 | 4/1992  |
| DE | 195 20 246   | 7/1995  |
| DE | 198 48 800   | 5/1999  |
| EP | 0 377 469    | 7/1990  |
| EP | 0 563 982    | 10/1992 |
| JP | 2-4725       | 1/1990  |
| JP | 2-503441     | 10/1990 |
| WO | WO 98/08791  | 3/1998  |

OTHER PUBLICATIONS

CAPLUS 1995: 784832.*
"In-Plane Switching: A Novel Electrooptic Effect" by G. Baur et al., Freiburger Argeistagung Flussigkristralle, Abstract No. 22, 1993, pp. 1-6.
"Principles and Characteristics of Electro-Optical Behaviour with In-Plane Switching Mode" by M. Oh-e, et al., ASIA Display '95, pp. 577-580.
"Development of Super-High-Image-Quality Vertical-Alignment-Mode LCD" by K. Ohmuro, et al., SID 97 Digest, 1997, pp. 845-848.

* cited by examiner

*Primary Examiner*—Shean C. Wu
(74) *Attorney, Agent, or Firm*—McDermott Will & Emery LLP

(57) ABSTRACT

Liquid crystalline compounds having a large negative $\Delta\epsilon$ low viscosity, a large $K_{33}/K_{11}$ value, a small $\Delta\epsilon/\Delta\perp$ and mutually excellent solubility even at low temperature, compositions containing at least one of the compounds and liquid crystal display devices containing such a liquid crystal compositions are disclosed.

10 Claims, No Drawings

ALKENYL COMPOUND HAVING A NEGATIVE Δε VALUE, LIQUID CRYSTAL COMPOSITION, AND LIQUID CRYSTAL DISPLAY DEVICE

This application is a continuation of application Ser. No. 09/323,820, filed Jun. 2, 1999, now U.S. Pat. No. 6,692,657.

TECHNICAL FIELD

The present invention relates to a liquid crystalline compound and a liquid crystal composition, and more particularly, to a novel liquid crystalline compound simultaneously having an alkenyl group and 2,3-difluorophenyl group, a liquid crystal composition containing such a compound, and a liquid crystal display device constituted from such a liquid crystal composition.

BACKGROUND ART

When a voltage is impressed to a conventional TN mode TFT display or a conventional STN display, liquid crystal molecules rotate to extend in the direction perpendicular to the substrate. When such liquid crystal molecules rise diagonally (i.e., such that they extend perpendicular to the substrate), there arise problems in that the optical properties of the liquid crystal molecules differ depending on the angle from which the liquid crystal panel is viewed, and in that the view angle is narrow.

As systems for realizing a wide view angle, the In-Plane-Switching (IPS) system characterized in the formation of comb style electrodes on one substrate (G. Baur, Freiburger Arbeistagung Flussigkristalle, Abstract No. 22 (1993), M. Oh-e, et al., ASIA DISPLAY '95, 577 (1995)), and the Vertically Aligned (VA) system (K. Ohmuro, et al., SID 97 DIGEST, 845 (1997)) have attracted attention, and have been put into practical use.

In the IPS system, since liquid crystal molecules rotate within the surface plane of the glass substrate, the view angle is greatly widened. In the VA system, liquid crystal molecules rotate from the vertical direction to the horizontal direction to the substrate, and a wide view angle is realized by controlling orientation in a kind of multi-domain system.

However, as compared to CRTs, these display systems still have problems, and there are the demands for improvement of response time, improvement of contrast, and decrease of driving voltage.

The liquid crystalline compound employed in IPS and VA systems must have the large negative value of dielectric anisotropy (Δε) for its display properties, and a low viscosity for improving response time. Since active matrix driving is utilized as the driving method, the compound must have a high voltage holding ratio (V.H.R.) in order to improve contrast.

Various compounds have been known to have negative values of dielectric anisotropy, and the following compounds (a) and (b) are disclosed in Japanese Patent Application Laid Open No. 2-4725 and Japanese-translated PCT Patent Application Laid-open No. 2-503441:

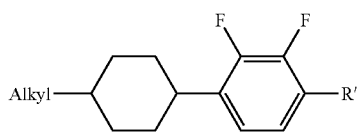

(a)

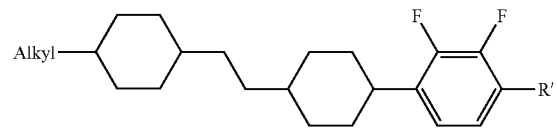

(b)

Where, R' represents an alkyl group or an alkoxy group.

Although each of the above liquid crystalline compounds, (a) and (b), has 2,3-difluoro-1,4-phenylene group as part of its structure, and has a negative Δε, |Δε| is not sufficiently large and viscosity is high. Furthermore, mutually good solubility its with other liquid crystalline compounds, especially mutually good solubility at very low temperature, is not sufficiently high, and a liquid crystal composition containing such compounds is so unstable that low-temperature storage results in precipitation of crystals or appearance of a smectic phase.

In order to solve the problems involved in the prior art techniques, an object of the present invention is to provide a liquid crystalline compound having a wide temperature range within which a liquid crystal phase exists (hereinafter called a "liquid crystal phase temperature range"), a large negative Δε, low viscosity, and mutually good solubility at low temperature, which can contribute to improving response time and contrast and lowering driving voltage in IPS and VA systems and can contribute to improving steepness of the V-T (voltage-transmissivity) curve and contrast by increasing the $K_{33}/K_{11}$ value in the STN system; a liquid crystal composition containing such liquid crystalline compounds, and a liquid crystal display device constituted from such a liquid crystal composition.

DISCLOSURE OF INVENTION

The present inventors conducted repeated examinations for achieving the above and other objects, and found that each of a group of compounds containing an alkenyl group and 2,3-difluoro-1,4-phenylene group, represented by formula (1), exhibits a large negative Δε, wide liquid crystal phase temperature range, low viscosity, and mutually excellent solubility at low temperature, and that Δε/ε⊥ can be decreased and the $K_{33}/K_{11}$ value can be increased by appropriate selection of the positions of double bonds in the alkenyl group to attain the present invention.

The present invention is described as follows.

According to a first aspect of the present invention, there is provided a liquid crystalline compound represented by the following general formula (1):

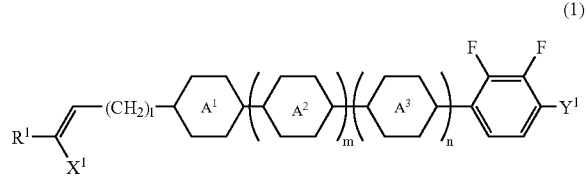

(1)

where, $R^1$ represents hydrogen, fluorine, an alkyl group having 1 to 15 carbon atoms, or an alkenyl group having 2 to 15 carbon atoms; each of rings $A^1$, $A^2$ and $A^3$ independently represents trans-i 4-cyclohexylene group, 1,4-cyclohexenylene group, trans-1,4-silacyclohexylene group, 1,4-phenylene group, 2,3-difluoro-1,4-phenylene group, 2-fluoro-1,4-phenylene group, 3-fluoro-1,4-phenylene group, pyrimidine-2,5-diyl group, pyridine-2,5-diyl group, 1,3-dioxane-2,5-diyl group, tetrahydro-pyrane-2,5-diyl group, 1,3-dithiane-2,5-diyl group, or tetrahydrothiopyrane-2,5-diyl group; $X^1$ represents hydrogen or fluorine; $Y^1$ represents hydrogen or an alkyl group having 1 to 15 carbon atoms, in which each of optional nonadjacent methylene groups (—$CH_2$—) may be substituted by oxygen; l represents an integer from 0 to 10; in which each of optional nonadjacent methylene groups in (—$CH_2$—)e may be substituted by oxygen; and each of m and n independently represents 0 or 1.

According to a second aspect of the present invention, there is provided a liquid crystalline compound according to the first aspect, wherein the ring $A_1$ in the general formula (1) is trans-1,4-cyclohexylene group and m and n are both 0.

According to a third aspect of the present invention, there is provided a liquid crystalline compound according to the first aspect, wherein each of the rings $A^1$ and $A^2$ in general formula (1) is independently trans-1,4-cyclohexylene group, 2,3-difluoro-1,4-phenylene group or 1,3-dioxane-2,5-diyl group; m is 1; and n is 0.

According to a fourth aspect of the present invention, there is provided a liquid crystalline compound according to the first aspect, wherein each of the rings $A^1$, $A^2$ and A in general formula (1) is independently trans-1,4-cyclohexylene group, 2,3-difluoro-1,4-phenylene group or 1,3-dioxane-2,5-diyl group; and m and n are both 1.

According to a fifth aspect of the present invention, there is provided a liquid crystal composition comprising at least two components, characterized by containing at least one liquid crystalline compound represented by general formula (1).

According to a sixth aspect of the present invention, there is provided a liquid crystal composition comprising at least one liquid crystalline compound according to any of the first through fourth aspects as a first component and at least one compound selected from a group consisting of compounds represented by general formulas (2), (3) and (4) as a second component,

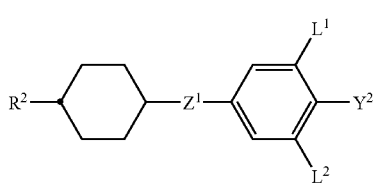

(2)

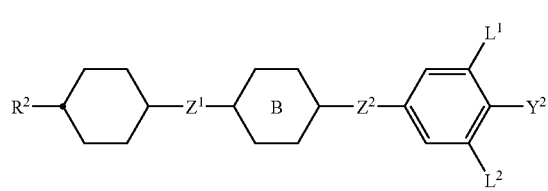

(3)

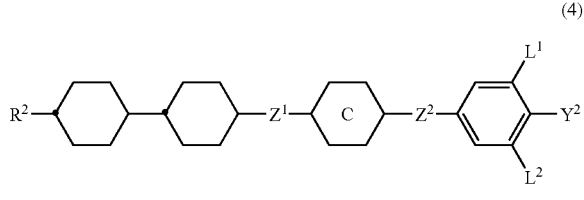

(4)

where $R^2$ represents an alkyl group having 1 to 10 carbon atoms, in which each of optional nonadjacent methylene groups may be substituted by oxygen or —CH=CH— group, and in which each of optional hydrogen in these methylene groups may be substituted by fluorine; $Y^2$ represents fluorine, chlorine, —$OCF_3$, —$OCF_2H$, —$CF_3$, —$CF_2H$, —$CFH_2$, —$OCF_2CF_2H$ or —$OCF_2CFHCF_3$; each of $L^1$ and $L^2$ independently represents hydrogen or fluorine; each of $Z^1$ and $Z^2$ independently represents 1,2-ethylene group, vinylene group, 1,4-butylene group, —COO—, —$CF_2O$—, —$OCF_2$— or a single bond; ring B represents trans-1,4-cyclohexylene group, 1,3-dioxane-2,5-diyl group or 1,4-phenylene group, in which each of hydrogen may be substituted by fluorine; and ring C represents trans-1,4-cyclohexylene group or 1,4-phenylene group, in which each of hydrogen may be substituted by fluorine.

According to a seventh aspect of the present invention, there is provided a liquid crystal composition comprising at least one liquid crystalline compound according to any of the first through fourth aspects as a first component, and at least one compound selected from a group consisting of compounds represented by general formulas (5) and (6) as a second component,

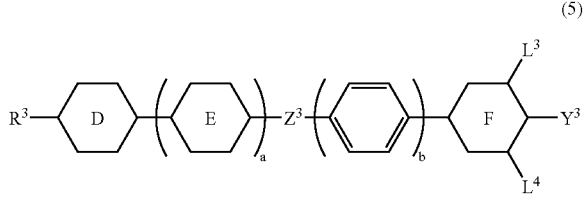

(5)

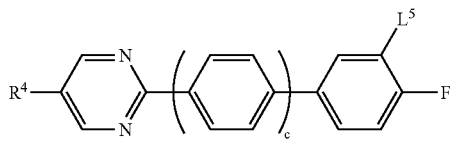

(6)

where each of $R^3$ and $R^4$ independently represents an alkyl group having 1 to 10 carbon atoms, in which each of optional nonadjacent methylene groups may be substituted by oxygen or vinylene group, and in which each of optional hydrogen in these methylene groups may be substituted by fluorine; $Y^3$ represents —CN or —C≡C—CN; ring D represents trans-1,4-cyclohexylene group, 1,4-phenylene group, pyrimidine-2,5-diyl group or 1,3-dioxane-2,5-diyl group; ring E represents trans-1,4-cyclohexylene group or 1,4-phenylene group, in which each of optional hydrogen may be substituted by fluorine; or pyrimidine-2,5-diyl group; ring F represents trans-1,4-cyclohexylene group or 1,4-phenylene group; $Z^3$ represents 1,2-ethylene group, —COO— or a single bond; each of $L^3$, $L^4$ and $L^5$ independently represents hydrogen or fluorine; and each of a, b and c independently represents 0 or 1.

According to an eighth aspect of the present invention, there is provided a liquid crystal composition comprising at least one liquid crystalline compound according to any of the first through fourth aspects as a first component and at least one compound selected from a group consisting of compounds represented by general formulas (7), (8) and (9) as a second component,

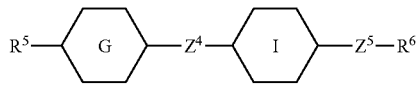

(7)

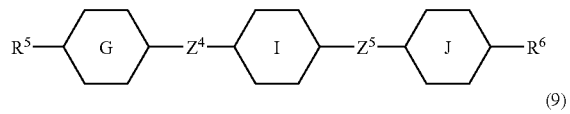

(8)

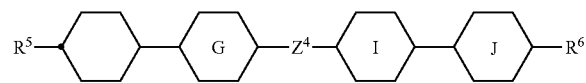

(9)

where each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene groups may be substituted by fluorine; each of rings G, I and J independently represents trans-1,4-cyclohexylene group, pyrimidine-2,5-diyl group or 1,4-phenylene group in which hydrogen may be substituted by fluorine; and each of $Z^4$ and $Z^5$ independently represents 1,2-ethylene group, vinylene group, —COO—, —C≡C— or a single bond.

According to a ninth aspect of the present invention, there is provided a liquid crystal composition comprising at least one liquid crystalline compound according to any of the first through fourth aspects as a first component and at least one compound selected from a group consisting of compounds represented by general formulas (10), (11) and (12) as a second component,

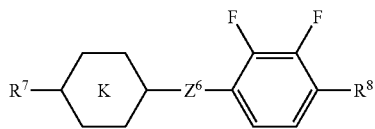

(10)

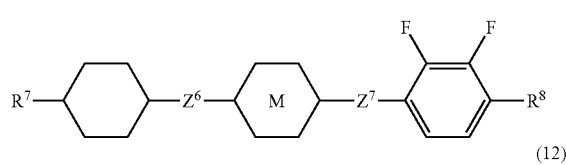

(11)

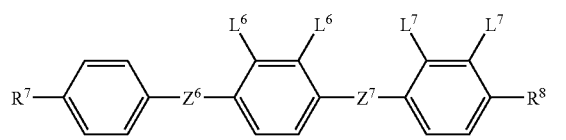

(12)

where each of $R^7$ and $R^8$ independently represents an alkyl group having 1 to 10 carbon atoms, in which each of optional nonadjacent methylene groups may be substituted by oxygen or vinylene group, and in which each of optional hydrogen in these methylene groups may be substituted by fluorine; each of rings K and M independently represents trans-1,4-cyclohexylene group or 1,4-phenylene group; each of $L^6$ and $L^7$ independently represents hydrogen or fluorine, but $L^6$ and $L^7$ are not both hydrogen simultaneously; and each of $Z^6$ and $Z^7$ independently represents —CH$_2$CH$_2$—, —CH$_2$O— or a single bond.

According to a tenth aspect of the present invention, there is provided a liquid crystal composition comprising at least one liquid crystalline compound according to any of the first through fourth aspects as a first component, at least one compound selected from a group consisting of compounds represented by general formulas (7), (8) and (9) as a second component and at least one compound selected from a group consisting of compounds represented by general formulas (10), (11) and (12) as a third component.

According to an eleventh aspect of the present invention, there is provided a liquid crystal composition comprising at least one liquid crystalline compound according to any of the first through fourth aspects as a first component, at least one compound selected from a group consisting of compounds represented by general formulas (2), (3) and (4) as a second component and at least one compound selected from a group consisting of compounds represented by general formulas (7), (8) and (9) as a third component.

According to a twelfth aspect of the present invention, there is provided a liquid crystal composition comprising at least one liquid crystalline compound according to any of the first through fourth aspects as a first component, at least one compound selected from a group consisting of compounds represented by general formulas (5) and (6) as a second component and at least one compound selected from a group consisting of compounds represented by general formulas (7), (8) and (9) as a third component.

According to a thirteenth aspect of the present invention, there is provided a liquid crystal composition comprising at least one liquid crystalline compound according to any of the first through fourth aspects as a first component, at least one compound selected from a group consisting of compounds represented by general formulas (2), (3) and (4) as a second component, at least one compound selected from a group consisting of compounds represented by general formulas (5) and (6) as a third component, and at least one compound selected from a group consisting of compounds represented by general formulas (7), (8) and (9) as a fourth component.

According to a fourteenth aspect of the present invention, there is provided a liquid crystal composition according to any of the fifth through thirteenth aspects further comprising one or more optically active compounds.

According to a fifteenth aspect of the present invention, there is provided a liquid crystal display device constituted from a liquid crystal composition according to any of the fifth through fourteenth aspects.

The liquid crystalline compounds of the present invention represented by the general formula (1) are compounds having two to four rings and characterized by containing an alkenyl group and 2,3-difluorophenyl group simultaneously. These liquid crystalline compounds not only exhibit physical and chemical stability under conditions where liquid crystal display devices are used, but also have a wide liquid crystal phase temperature range, a large negative Δε, and low viscosity, enable an increase in the $K_{33}/K_{11}$ value, and are highly soluble in liquid crystal compositions even at low temperature.

Although, as described in the description of the Background Art, compounds having 2,3-difluoro-1,4-phenylene group in respective partial structures have been disclosed in patent gazettes or other references, the present inventors are the first to discover that compounds having both an alkenyl group and the above structure have the above features. In the compounds of the present invention, desired properties can be adjusted by suitable selection of the ring structures, or the structures of bonding groups or side chains among the elements constituting a molecule. Therefore, when the compounds of the present invention ate used as the components of liquid crystal compositions, nemetic liquid crystal compositions having the following preferable properties can be prepared.

1) Since the liquid crystal phase temperature range is wide, the usable temperature range is expanded.

2) Since the compositions have large negative Δε and low viscosity, response time is improved and driving voltage is lowered in IPS and VA systems. 3) Since the $K_{33}/K_{11}$ value can be increased and $\Delta\epsilon/\epsilon\perp$ can be decreased in the STN system, the steepness of the V-T (voltage-transmissivity) curve is improved.

4) Stable nematic liquid crystal compositions can be prepared without the precipitation of crystals and the appearance of a smectic phase, even at extremely low temperature.

Thus, there can be provided novel liquid crystal compositions and liquid crystal display devices which are stable in usage environments, which realize the expansion of usable temperature range, and which have a low driving voltage and high response speed and provide high contrast.

Although all compounds of the present invention have favorable properties, a liquid crystal composition meeting the requirements of specific applications can be prepared by use of compounds in which $R^1$, ring $A^1$, ring $A^2$, ring $A^3$, $X^1$, $Y^1$, l, m and n in general formula (1) have been properly selected.

If a compound having a large negative Δε is desired, 2,3-difluoro-1,4-phenylene group may be bonded at the site of ring $A^1$, ring $A^2$, or ring $A^3$; if the liquid crystal phase temperature range is required to be on the low-temperature side, a two-ring compound (m=n=0) may be selected; if the liquid crystal phase temperature range is required to be on the high-temperature side, a three-ring or four-ring compound (m+n=1 or m+n=2) may be selected; and if a large refractive index of anisotropy is required, 1,4-phenylene group may be bonded at the site of ring $A^1$, ring $A^2$ or ring $A^3$. The compound in which a hydrogen atom on the 1,4-phenylene group is substituted by a fluorine atom has especially excellent solubility at low temperature.

Among the compounds represented by the general formula (1), examples of especially favorable compounds are those represented by the following general formulas (1-1) through (1-7):

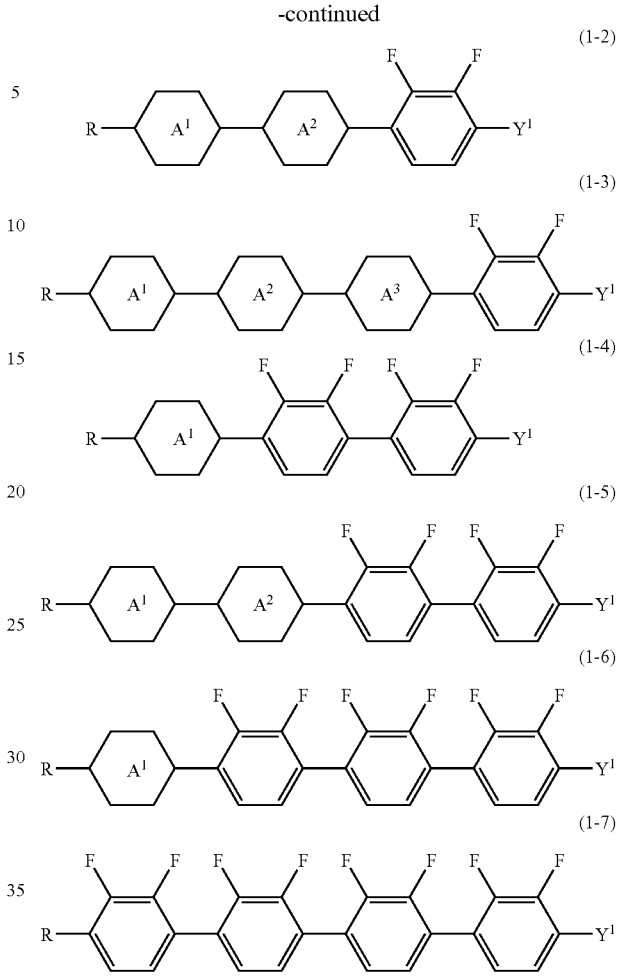

where, ring $A^1$, ring $A^2$, ring $A^3$, and $Y^1$ have the same meanings as described above, and R has the following structure;

R:

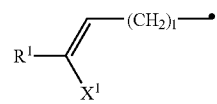

where, $R^1$ and $X^1$ have the same meanings as described above.

In general formulas (1-1) through (1-7), R represents an alkenyl group or an alkenyloxy group having 2 to 15 carbon atoms, among which vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy and 4-pentenyloxy groups are particularly preferable; and $Y^1$ represents hydrogen, an alkyl group having 1 to 15 carbon atoms or an alkoxy group, among which methyl, ethyl, propyl, butyl, pentyl, hexyl, heptyl, octyl, methoxy, ethoxy, propoxy, butoxy, pentyloxy, hexyloxy, heptyloxy, and octyloxy groups are particularly preferable.

The liquid crystal composition of the present invention will be described below. In order to exhibit favorable properties, the liquid crystal composition of the present invention preferably contains at least one of the compounds represented by the general formula (1) in a total amount of 0.1 to 99.9% by weight.

More specifically, the liquid crystal composition of the present invention comprises a first component containing at least one of the compounds represented by general formula (1) and a second component comprising a compound selected from the group of compounds represented by general formulas (2) through (12) according to the purpose of the liquid crystal composition.

Among the compounds represented by general formulas (2) through (4), compounds represented by the following general formulas (2-1) through (4-24) are particularly preferred, where $R^2$ and $Y^2$ have the same meanings as described above:

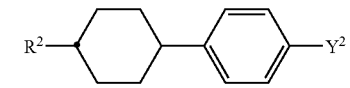
(2-1)

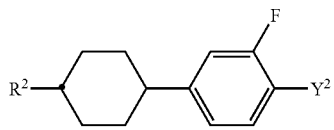
(2-2)

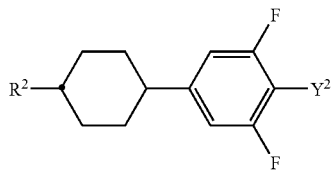
(2-3)

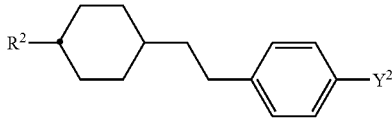
(2-4)

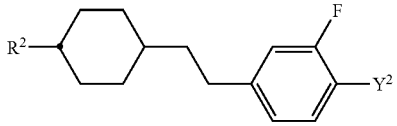
(2-5)

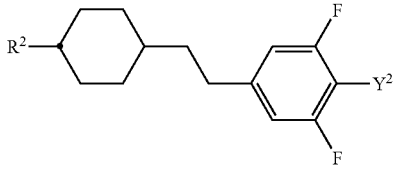
(2-6)

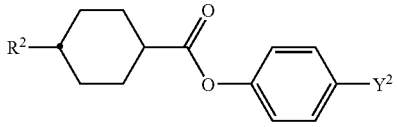
(2-7)

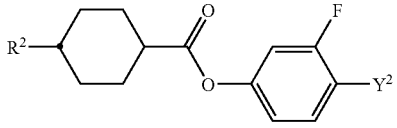
(2-8)

-continued

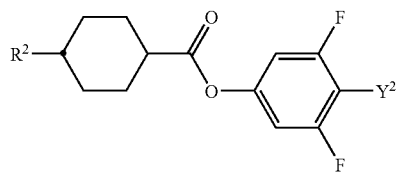
(2-9)

(3-1)

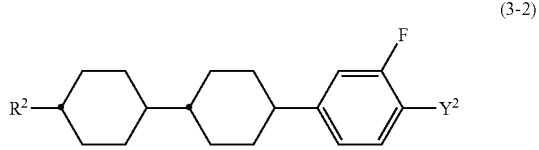
(3-2)

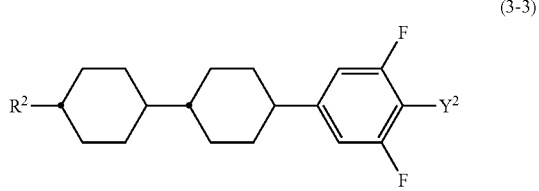
(3-3)

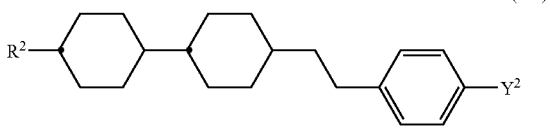
(3-4)

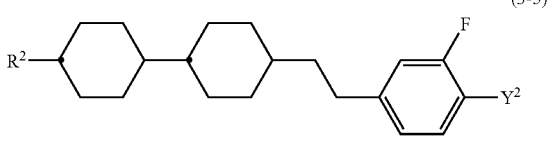
(3-5)

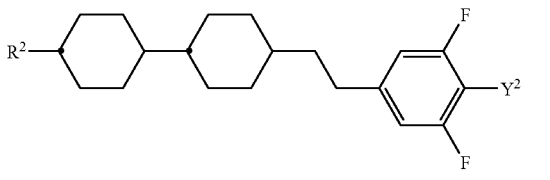
(3-6)

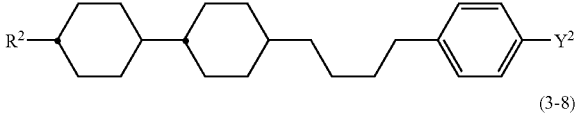
(3-7)

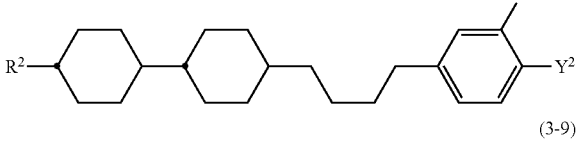
(3-8)

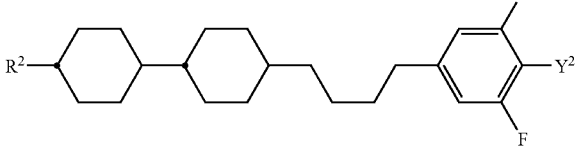
(3-9)

-continued
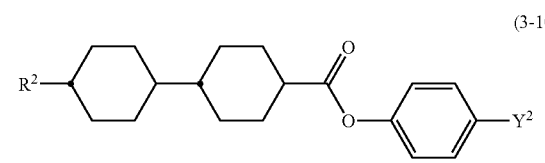 (3-10)
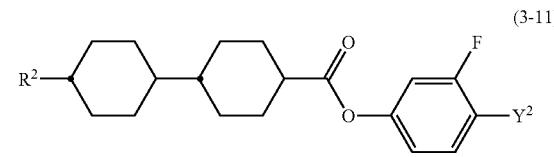 (3-11)
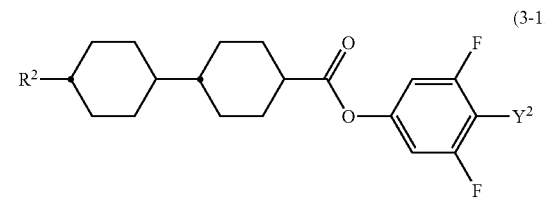 (3-12)
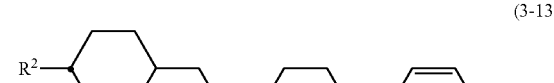 (3-13)
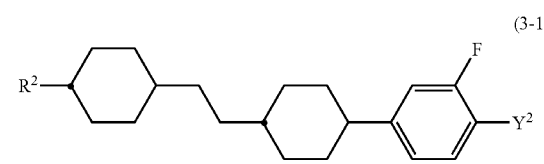 (3-14)
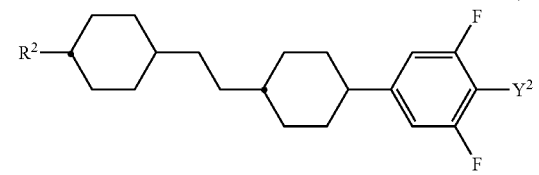 (3-15)
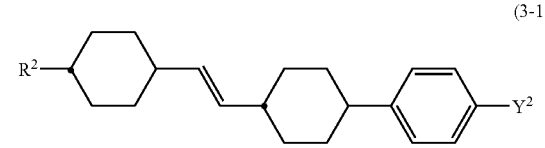 (3-16)
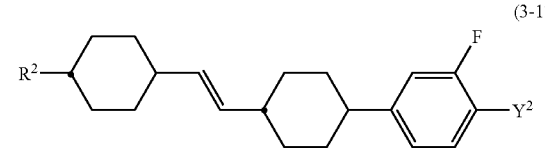 (3-17)
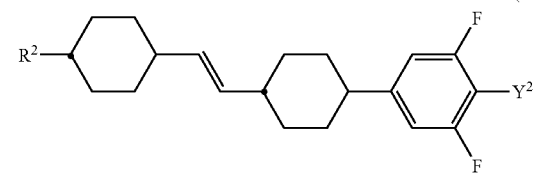 (3-18)
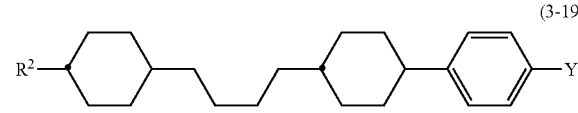 (3-19)
-continued
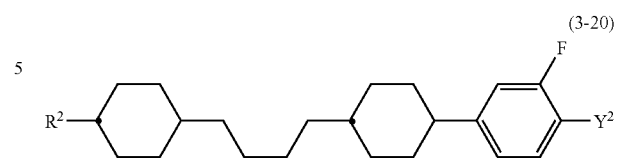 (3-20)
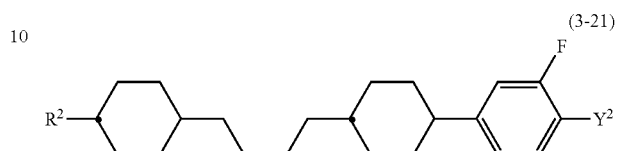 (3-21)
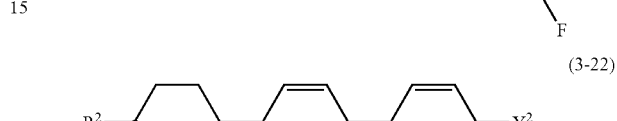 (3-22)
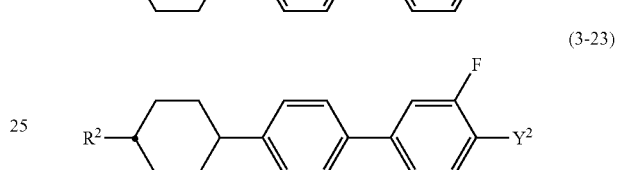 (3-23)
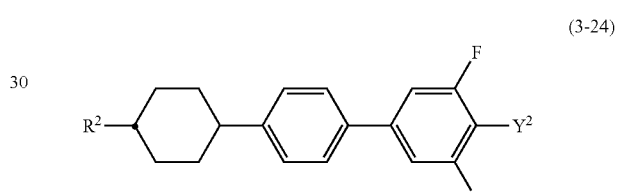 (3-24)
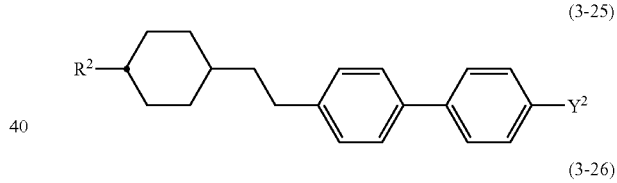 (3-25)
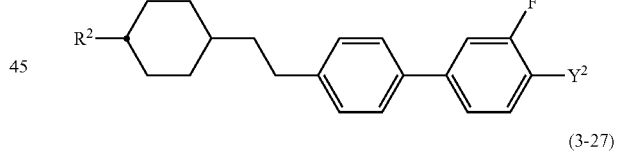 (3-26)
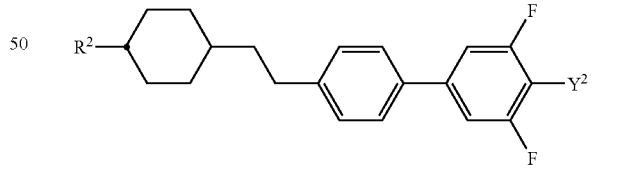 (3-27)
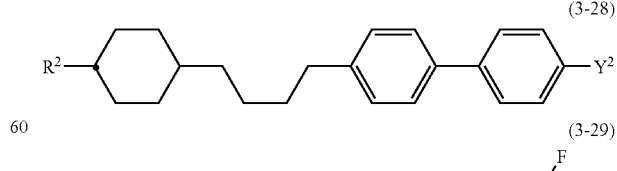 (3-28)
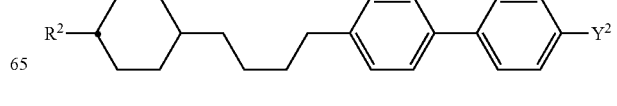 (3-29)

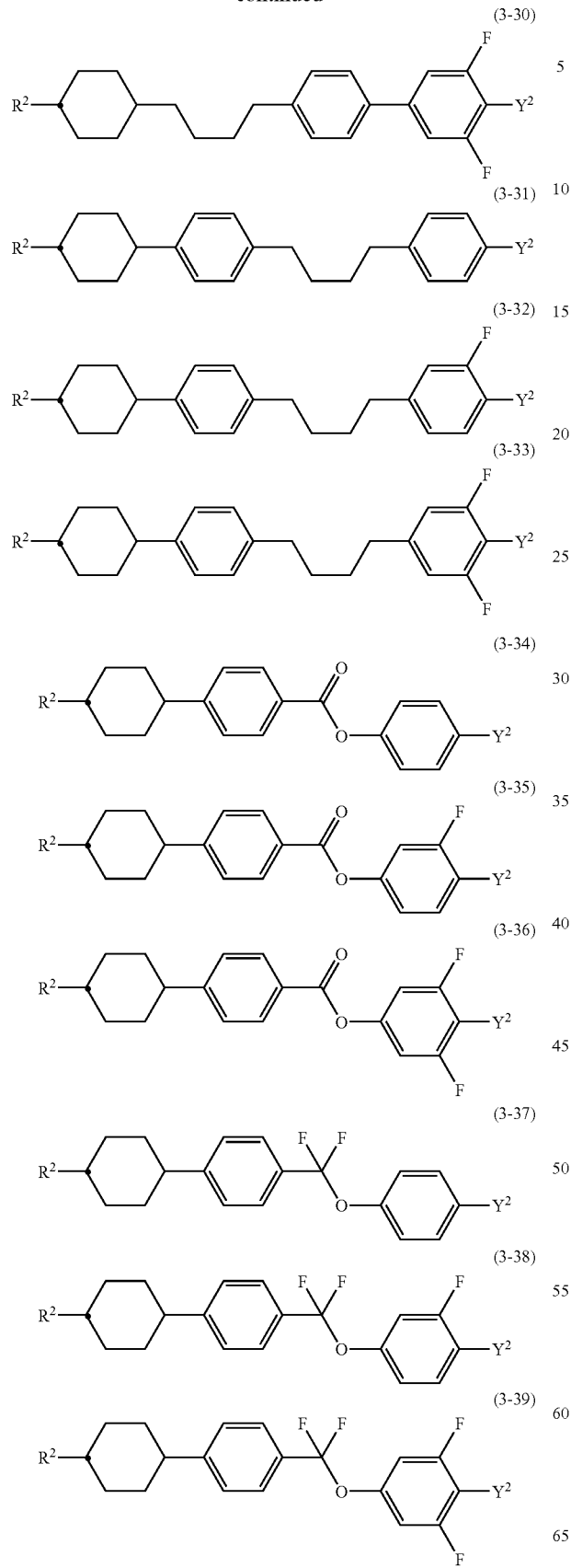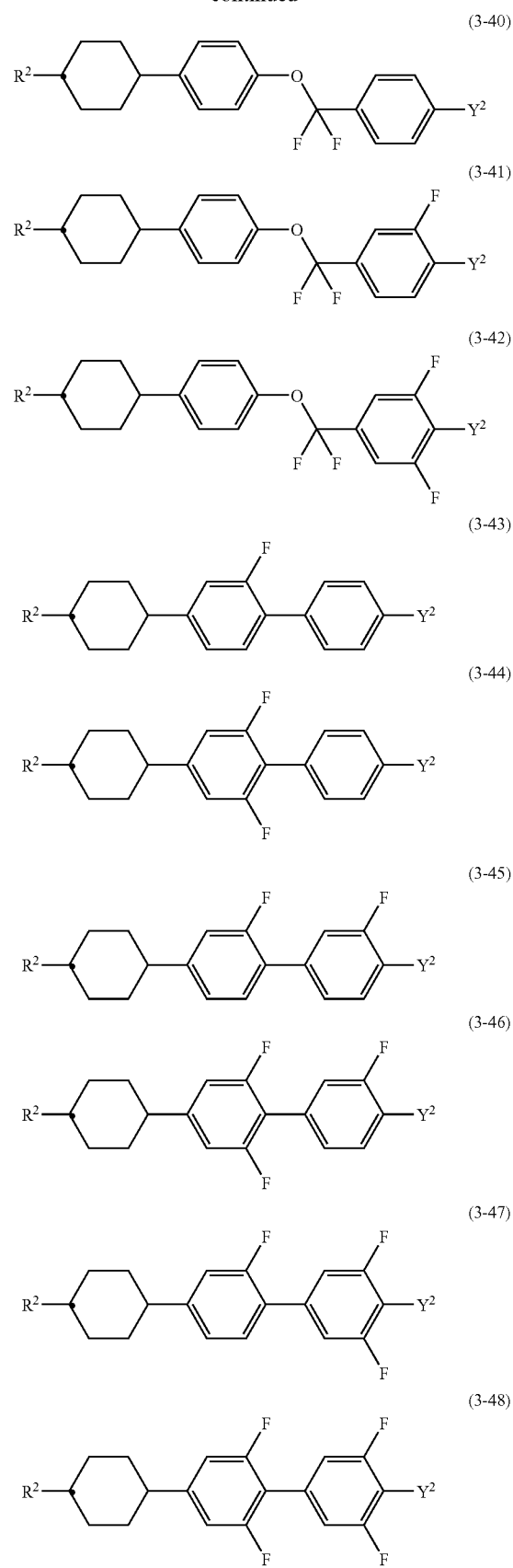

-continued
(3-49)
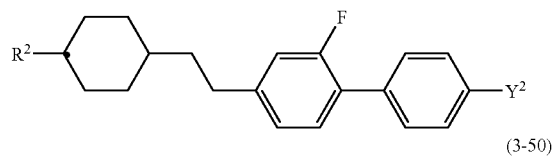
(3-50)
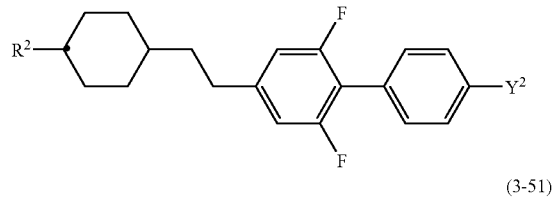
(3-51)
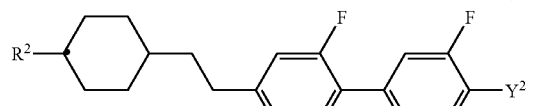
(3-52)
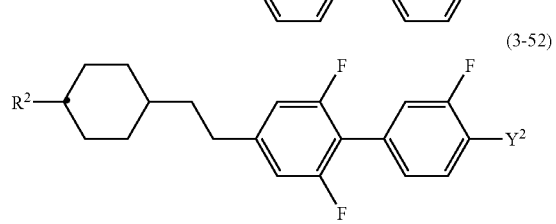
(3-53)
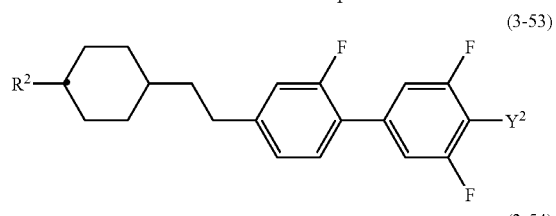
(3-54)
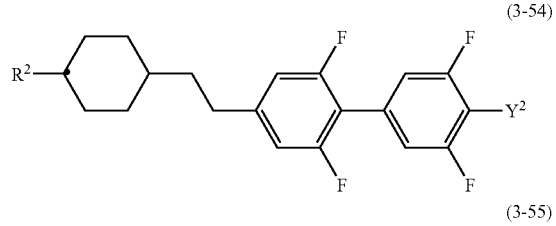
(3-55)
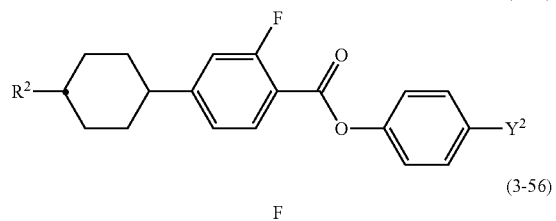
(3-56)
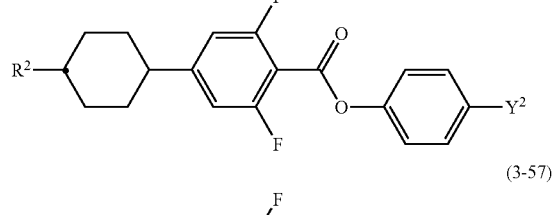
(3-57)
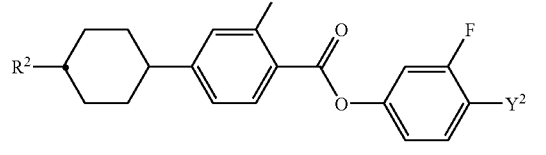
-continued
(3-58)
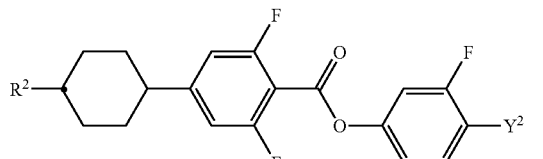
(3-59)
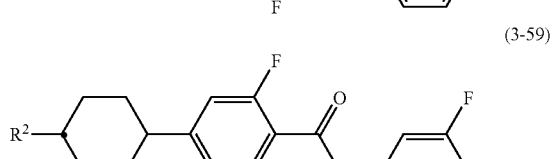
(3-60)
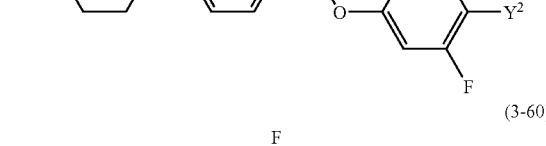
(3-61)
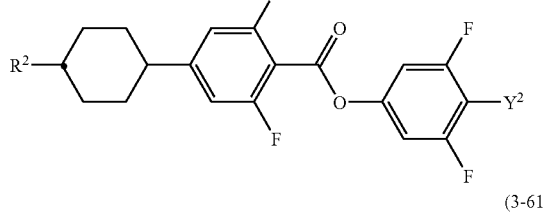
(3-62)
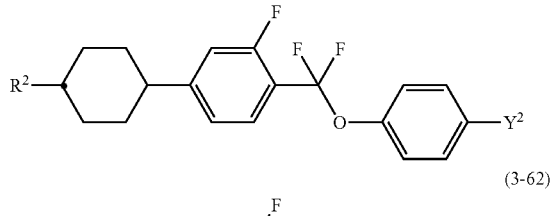
(3-63)
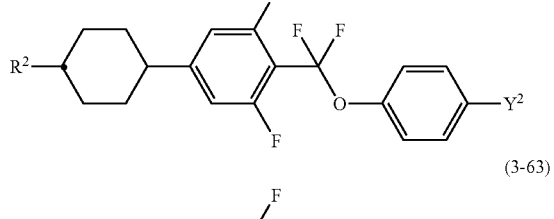
(3-64)
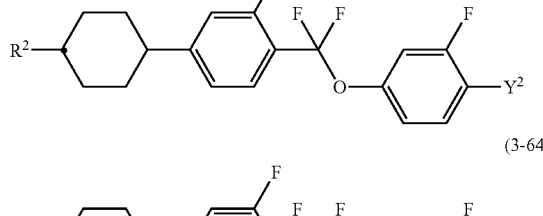
(3-65)
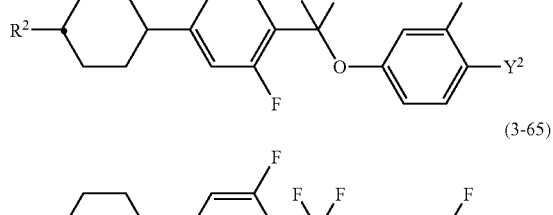

-continued
(3-66)
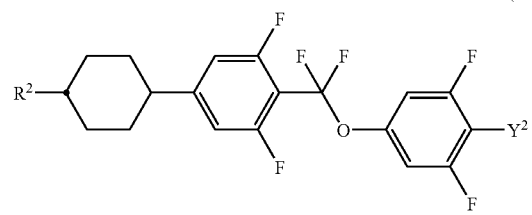
(3-67)
(3-68)
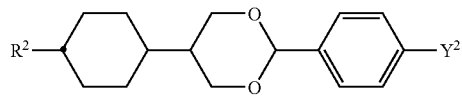
(3-69)
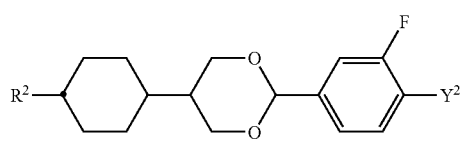
(4-1)
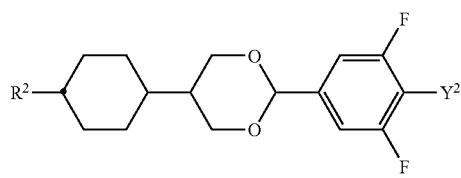
(4-2)
(4-3)
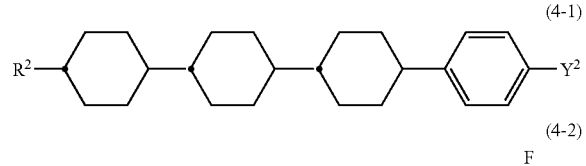
(4-4)
(4-5)
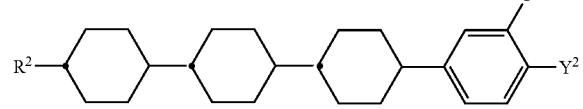
(4-6)
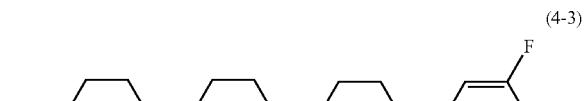
-continued
(4-7)
(4-8)
(4-9)
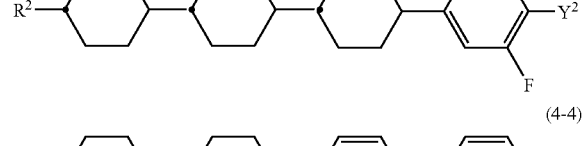
(4-10)
(4-11)
(4-12)
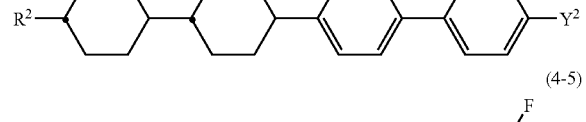
(4-13)
(4-14)
(4-15)
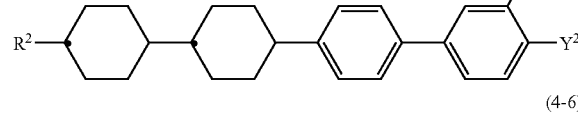

-continued

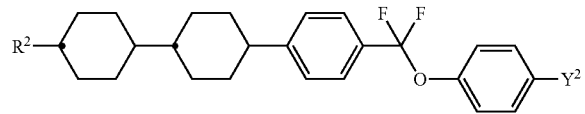
(4-16)

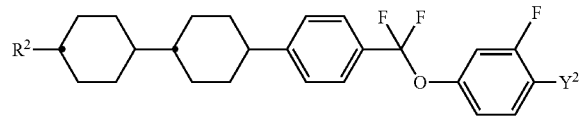
(4-17)

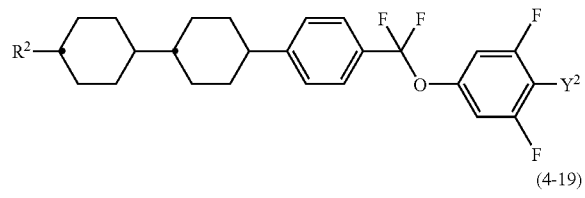
(4-18)

(4-19)

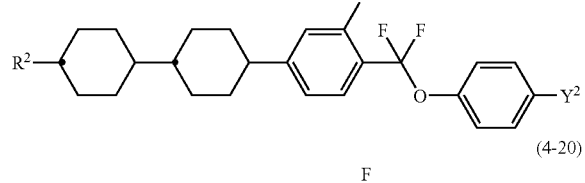
(4-20)

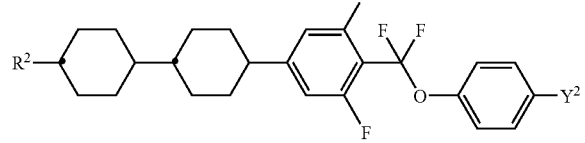
(4-21)

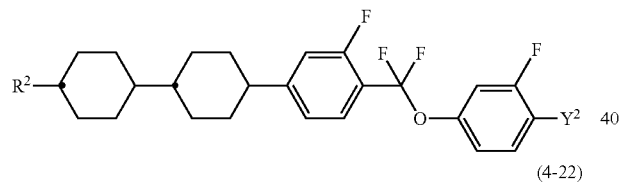
(4-22)

(4-23)

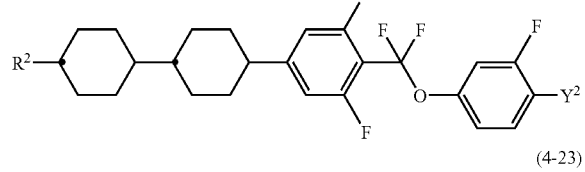
(4-24)

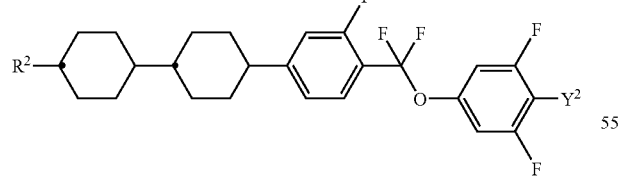

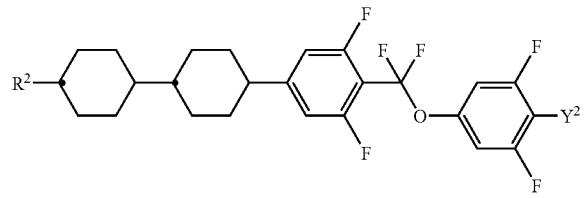

The compounds represented by general formulas (2) through (4) are compounds having positive values of dielectric anisotropy, and excellent thermal and chemical stability, and are particularly useful for preparing liquid crystal compositions for TFT (AM-LCD) displays which require high reliability; for example, a high voltage holding ratio or high specific resistance.

In preparing a liquid crystal composition for TFT displays, the compounds represented by general formulas (2) through (4) may be contained in a total amount of 0.1 to 99.9% by weight, preferably 10 to 97% by weight, and more preferably 40 to 95% by weight. In this case, compounds represented by general formulas (7) through (9) maybe further added for the adjustment of viscosity.

In preparing a liquid crystal composition for STN or TN displays, the compounds represented by general formulas (2) through (4) can also be used. Since the compounds represented by general formulas (2) through (4) have a weaker effect in lowering the threshold voltage of the liquid crystal composition than do the compounds represented by general formulas (5) and (6), the compounds represented by general formulas (2) through (4) are preferably contained in a total amount of 50% by weight or less.

Among the compounds represented by general formulas (5) and (6) are compounds represented by the following general formulas (5-1) through (6-3) are particular preferred; where, $R^3$, $R^4$ and $Y^3$ have the same meanings as described above.

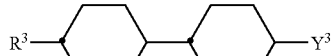
(5-1)

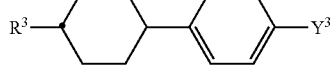
(5-2)

(5-3)

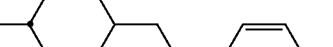
(5-4)

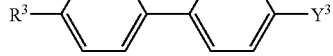
(5-5)

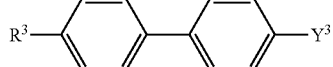
(5-6)

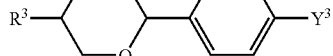
(5-7)

-continued
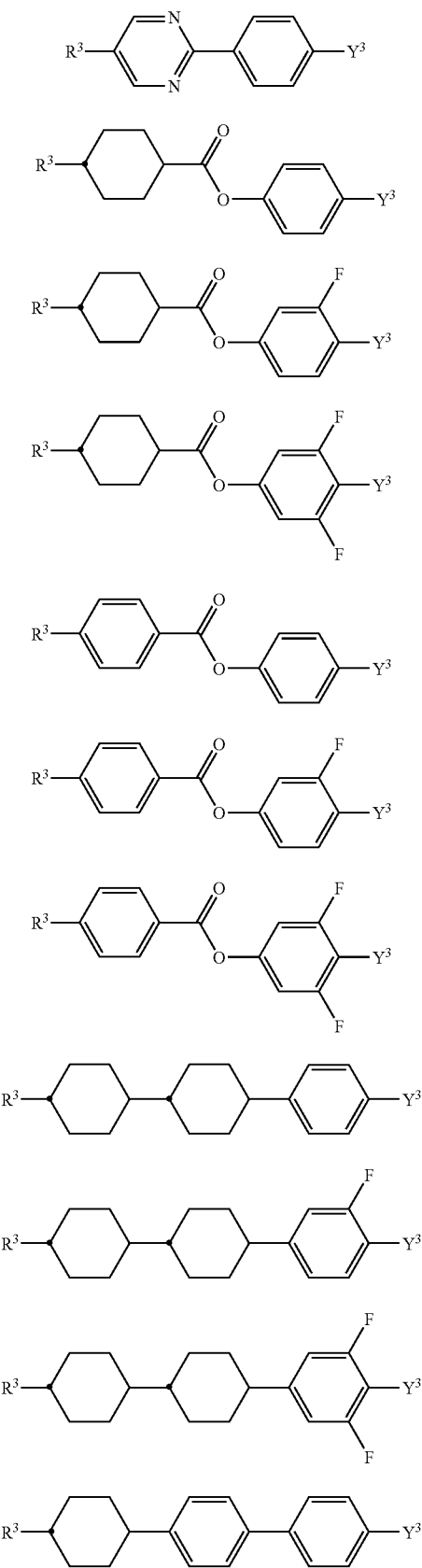
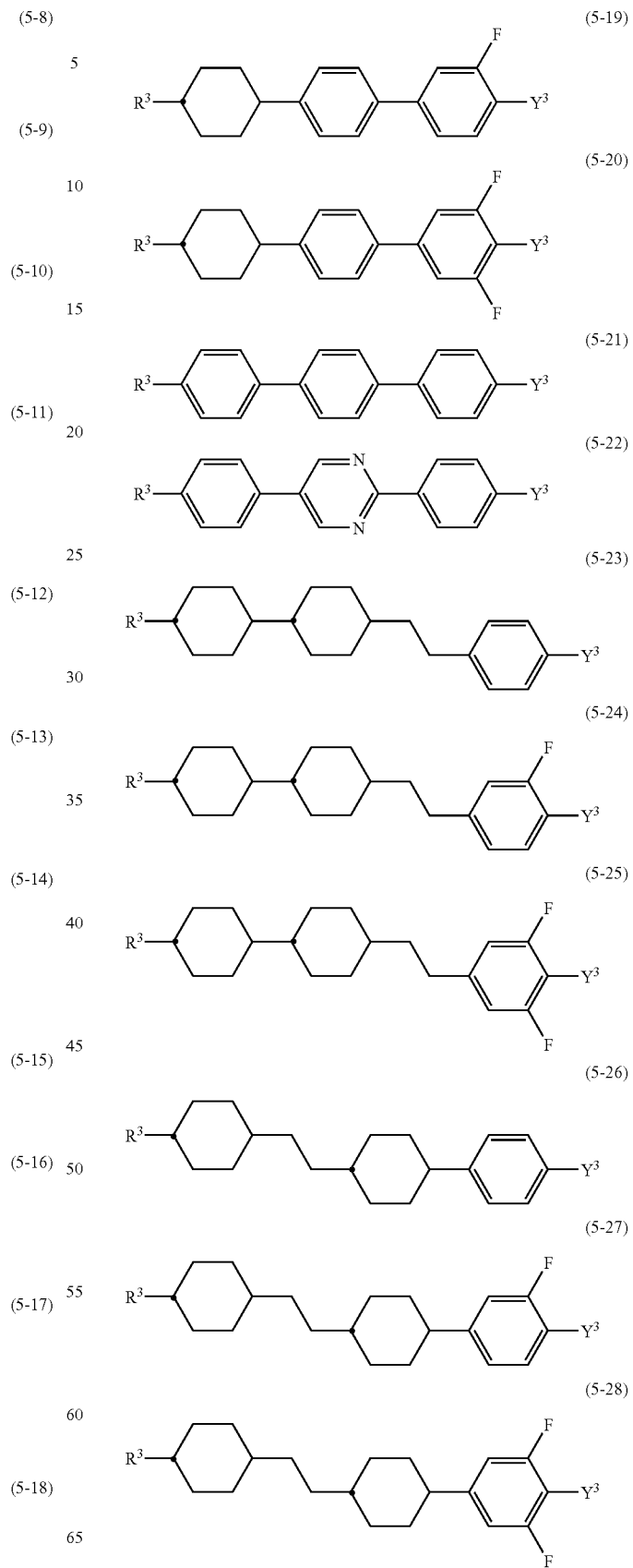

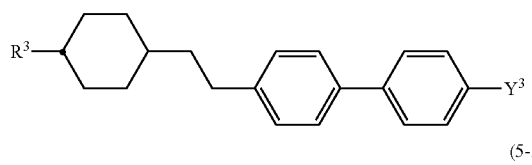
(5-29)

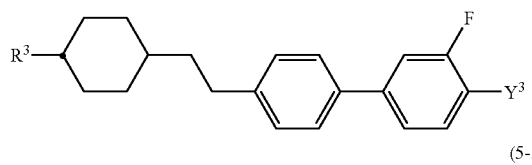
(5-30)

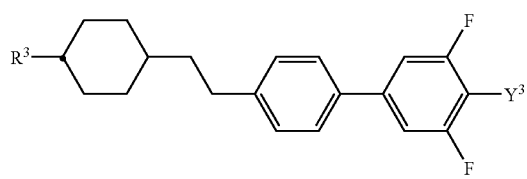
(5-31)

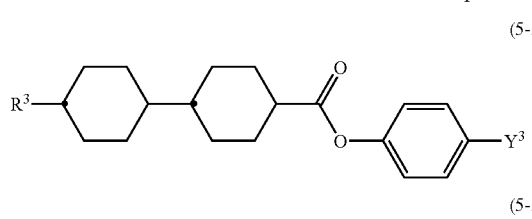
(5-32)

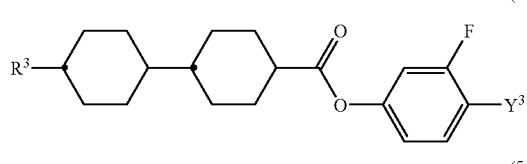
(5-33)

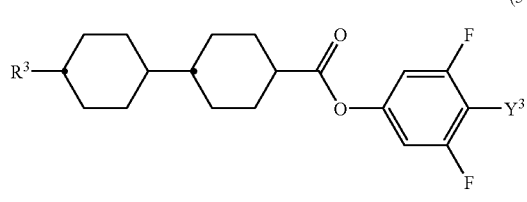
(5-34)

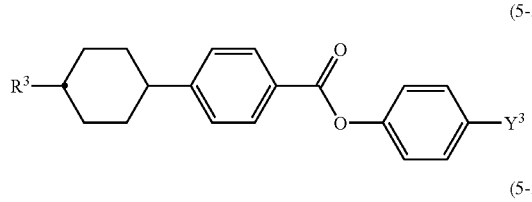
(5-35)

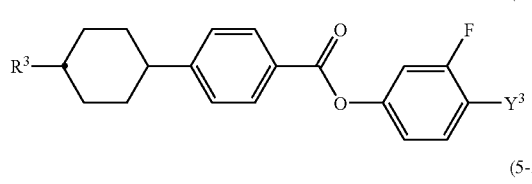
(5-36)

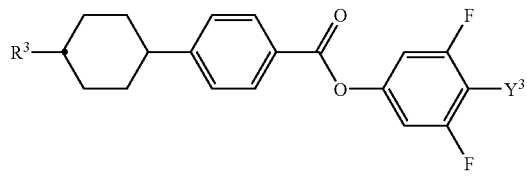
(5-37)

(5-38)

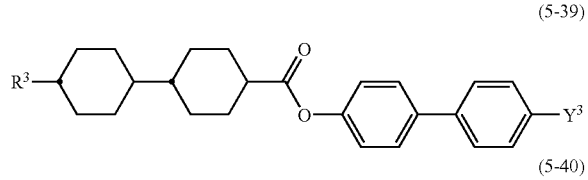
(5-39)

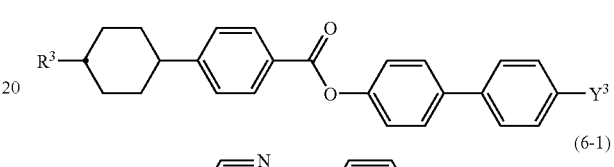
(5-40)

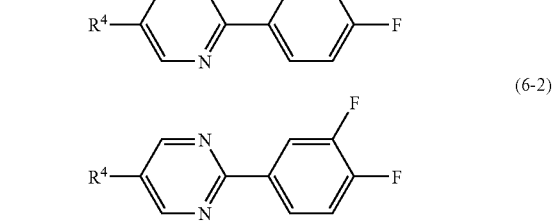
(6-1), (6-2), (6-3)

The compounds represented by general formulas (5) and (6) have large positive values of dielectric anisotropy, and are particularly useful for lowering the threshold voltage of liquid crystal compositions. These compounds are also used for expanding the nematic range such as for adjusting values of refractive index anisotropy and elevating clearing points. Furthermore, these compounds are used for improving the steepness of the V-T (voltage-transmissivity) curve of liquid crystal compositions for STN or TN displays.

The compounds represented by general formulas (5) and (6) are particularly useful for preparing liquid crystal compositions for STN or TN displays.

Increasing the quantity of the compounds represented by general formulas (5) and (6) has the effect of lowering the threshold voltage of the liquid crystal composition and increasing its viscosity. Therefore, use of a large amount of these compounds is advantageous for producing display element having low driving voltage, so long as the viscosity of the liquid crystal composition satisfies requirements. In preparing liquid crystal compositions for STN or TN displays, the total content of the compounds represented by general formulas (5) and (6) may be 0.1 and 99.9% by weight, preferably 10 to 97% by weight, and more preferably 40 to 95% by weight.

Among the compounds represented by general formulas (7) through (9), compounds represented by the following general formulas (7-1) through (9-6) are particularly preferred: where, $R^5$ and $R^6$ have the same meanings as described above.

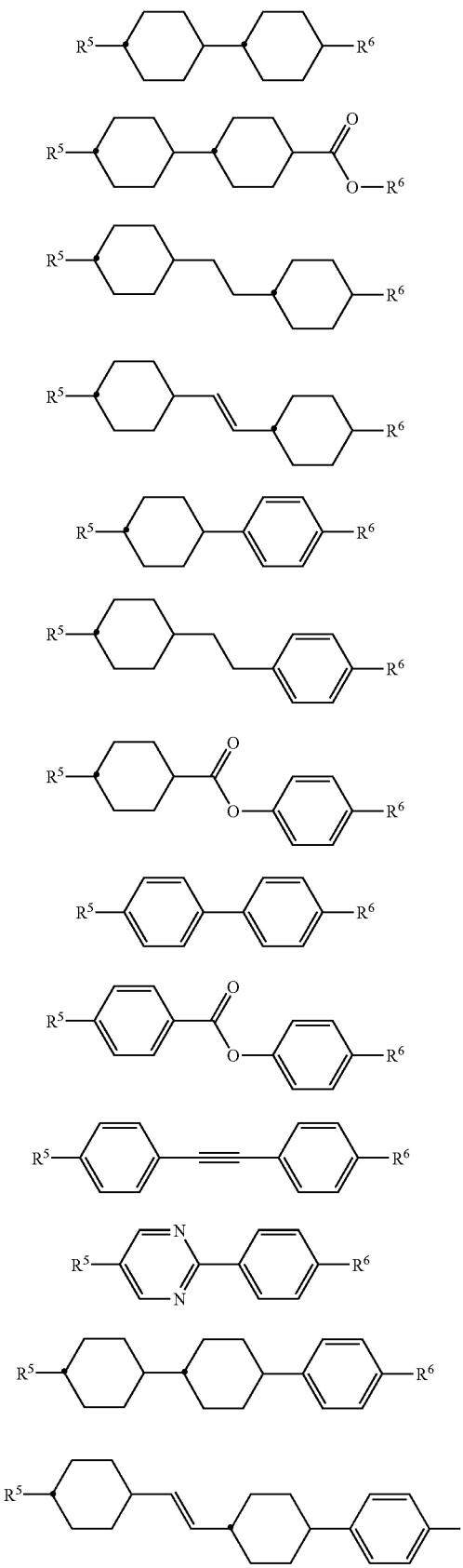
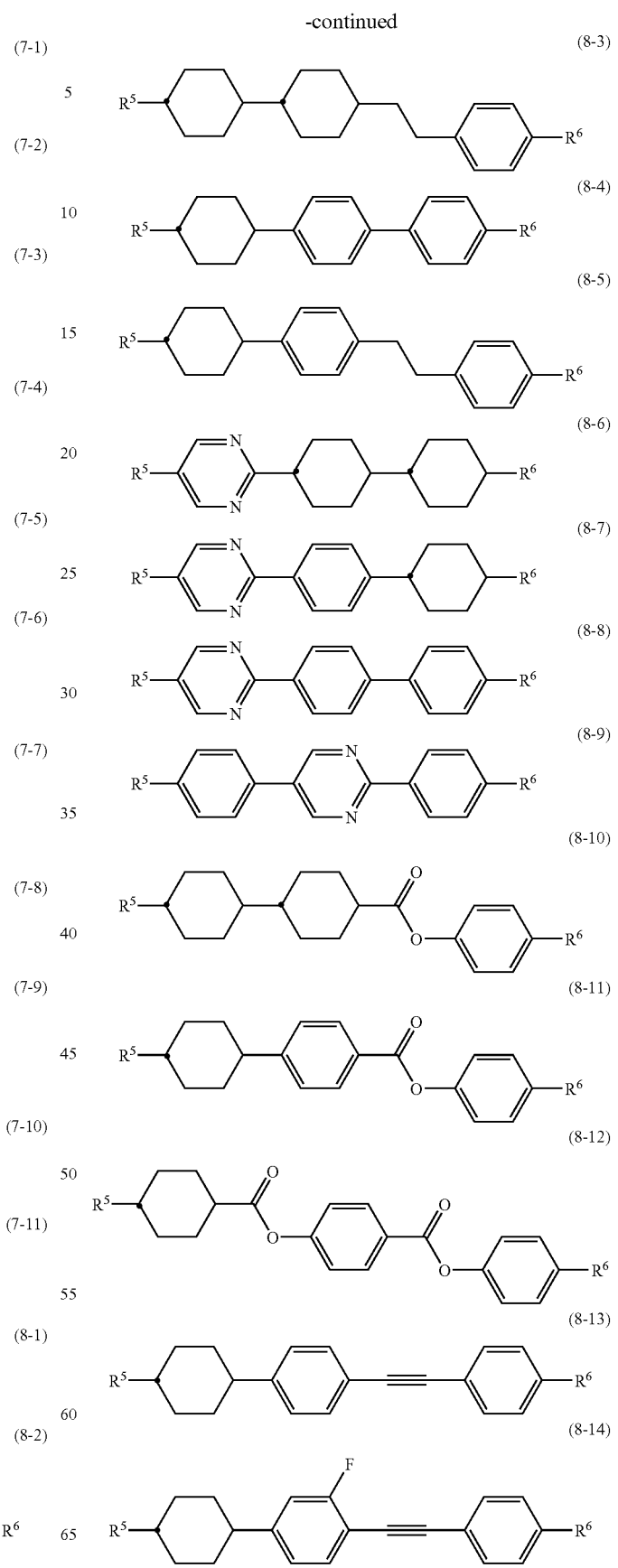

-continued

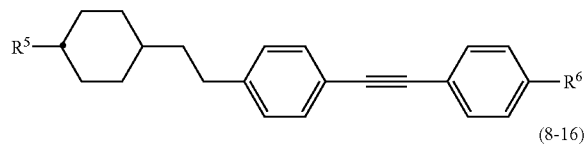
(8-15)

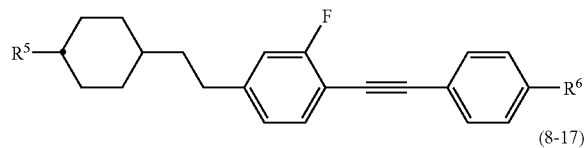
(8-16)

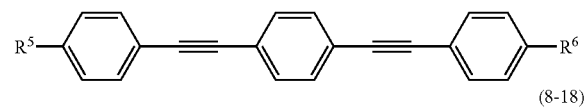
(8-17)

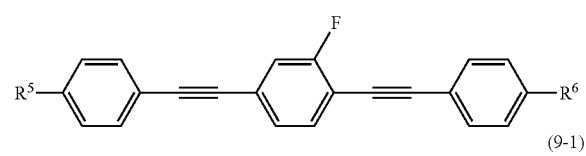
(8-18)

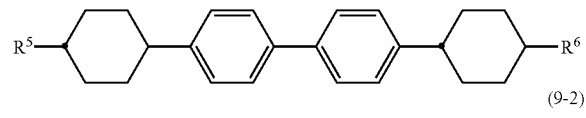
(9-1)

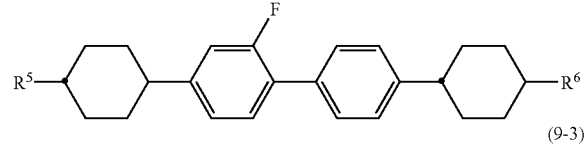
(9-2)

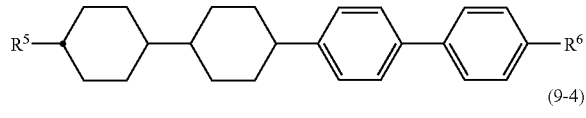
(9-3)

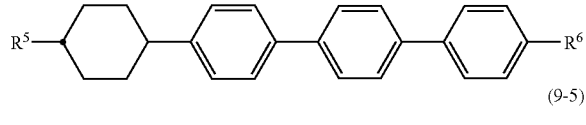
(9-4)

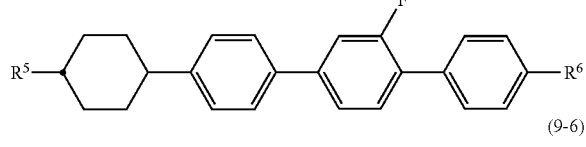
(9-5)

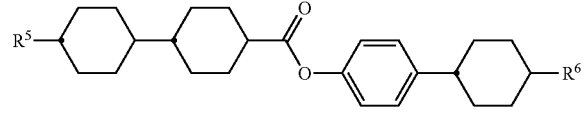
(9-6)

The compounds represented by general formulas (7) through (9) have small absolute values of dielectric anisotropy, and are nearly neutral. The compounds represented by the general formula (7) are mainly used for adjusting the viscosity or refractive index of anisotropy of liquid crystal compositions. The compounds represented by the general formulas (8) and (9) are used for expanding the nematic range by, for example, elevating the clearing point of liquid crystal composition, or for adjusting the refractive index of anisotropy.

Increase in the content of the compounds represented by general formulas (7) through (9) has the effects of increasing the threshold voltage and decreasing the viscosity of liquid crystal compositions. Therefore, these compounds are preferably used in a large amount, so long as the threshold voltage of liquid crystal compositions satisfy requirements.

When a liquid crystal composition for TFT displays is prepared, the content of the compounds represented by general formulas (7) through (9) is preferably 40% by weight or less, more preferably 35% by weight or less with respect to the liquid crystal composition. When a liquid crystal composition for STN or TN displays is prepared, the content of the compounds represented by general formulas (7) through (9) is preferably 70% by weight or less, more preferably 60% by weight or less with respect to the entirety of the liquid crystal composition.

Among the compounds represented by general formulas (10) through (12), compounds represented by the following general formulas (10-1) through (12-3) are particularly preferred; where, $R^7$ and $R^8$ have the same meanings as described above.

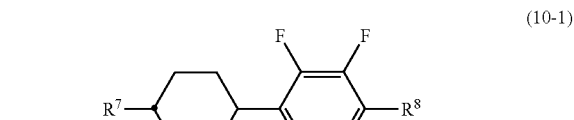
(10-1)

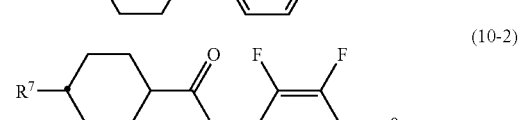
(10-2)

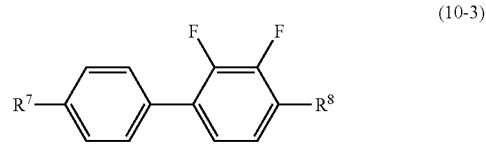
(10-3)

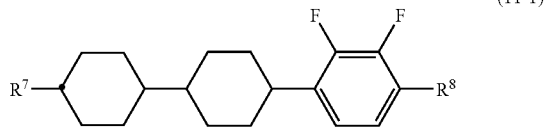
(11-1)

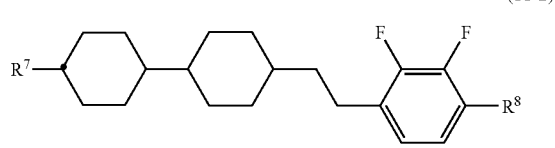
(11-2)

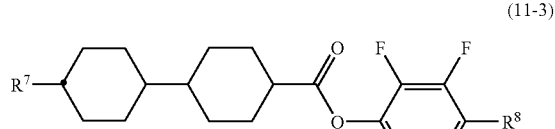
(11-3)

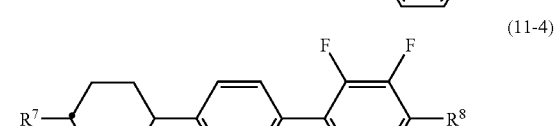
(11-4)

-continued

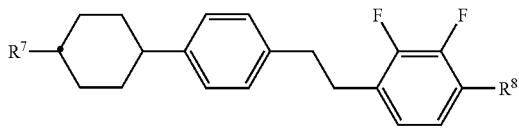
(11-5)

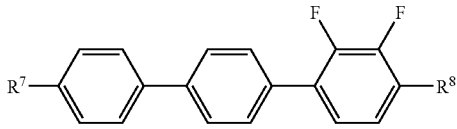
(12-1)

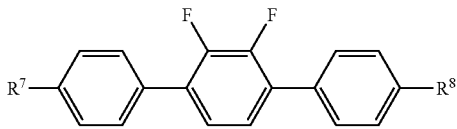
(12-2)

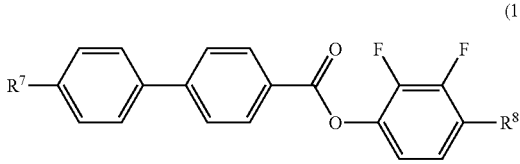
(12-3)

The compounds represented by general formulas (10) through (12) have negative values of dielectric anisotropy. The compounds represented by the general formula (10) are two-ring compounds, and are mainly used for adjusting threshold voltage, viscosity, and refractive index of anisotropy. The compounds represented by general formula (11) are used for expanding the nematic range; for example, for raising the clearing point, or for adjusting refractive index of anisotropy. The compounds represented by general formula (12) are used for expanding the nematic range, as well as for lowering threshold voltage and increasing refractive index of anisotropy.

Although the compounds represented by general formulas (10) through (12) are used in N-type compositions (i.e., composition having a negative value of dielectric anisotropy $\Delta\epsilon$), increase in their content has the effect of lowering the threshold voltage of the composition and increasing viscosity. Therefore, these compounds are preferably used in small amounts, so long as the threshold voltage of the liquid crystal composition satisfies requirements. However, since these compounds have absolute values of dielectric anisotropy of 5 or smaller, attaining a low driving voltage may become impossible if the content is less than 40% by weight.

When an N-type liquid crystal composition for TFT displays is prepared, the total content of the compounds represented by general formulas (10) through (12) is preferably 40% by weight or more, more preferably 50 to 95% by weight.

The compounds represented by general formulas (10) through (12) may also be added to a P-type liquid crystal composition (i.e., a compound having a positive value of dielectric anisotropy $\Delta\epsilon$) for controlling the elastic modulus of the liquid crystal composition, and for controlling the voltage-transmissivity curve (V-T curve). In such a case, the total content of the compounds represented by general formulas (10) through (12) is preferably 30% by weight or less.

In the liquid crystal composition of the present invention, an optically active compound is added so as to induce the helical structure of the liquid crystal composition for adjustment of twist angle and prevention of reverse twist, except for special cases such as liquid crystal compositions for OCB (optically compensated birefringence) mode displays. Although the optically active compounds added to the liquid crystal compositions of the present invention may be any known optically active compounds used for such a purpose, preferred examples include the following optically active compounds:

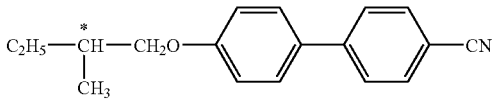
(mark:C15)

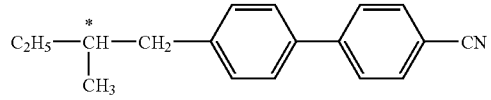
(mark:CB15)

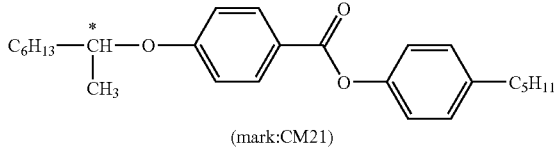
(mark:CM21)

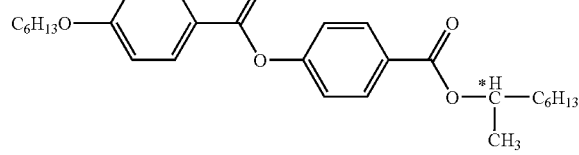
(mark:CM33)

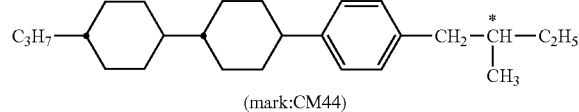
(mark:CM44)

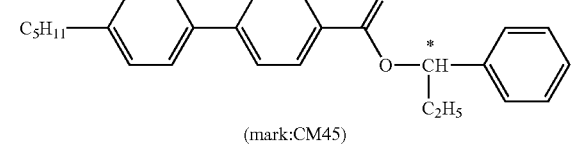
(mark:CM45)

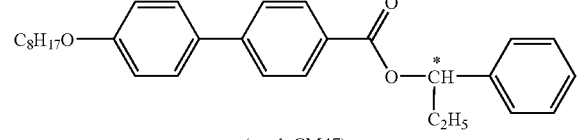
(mark:CM47)

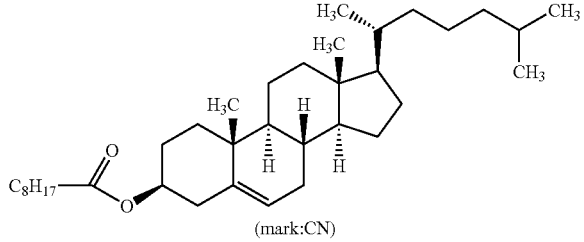
(mark:CN)

These optically active compounds are usually added to the liquid crystal composition of the present invention so as to adjust the pitch of the twist. The pitch of the twist is preferably adjusted within a range of 40 to 200 μm for liquid crystal compositions for TFT and TN displays, and within a range of 6 to 20 μm for liquid crystal compositions for STN displays. In the case of bistable TN-mode displays, the pitch of the twist is preferably adjusted within a range of 1.5 to 4 μm. Two or more optically active compounds may be added for adjustment of the temperature dependence of the pitch.

The liquid crystal composition of the present invention itself is prepared by conventional methods. In a typically adopted method, various components are mutually dissolved at high temperature.

The liquid crystal composition used according to the present invention can also be used as a liquid crystal composition for Guest-Host-mode (GH) displays by addition of merocyanine-, styryl-, azo-, azomethine-, azoxy-, quinophthalone-, anthraquinone-, or tetrazine-based dichroic colorants. It can also be used as the liquid crystal composition for NCAP produced by the micro-encapsulation of nematic liquid crystals, or for a Polymer Dispersed Liquid Crystal Display device (PDLCD) in which a three-dimensional polymer matrix is formed in liquid crystals. In addition, it can also be used as liquid crystal compositions for Electrically Controlled Birefringence mode (ECB) or Dynamic Scattering mode (DS) liquid crystal displays.

Method for Preparation of the Compounds

The compounds represented by the general formula (1) can be prepared easily by using of typical methods for synthesizing organic chemicals. For example, the compounds can be synthesized by selection and combination of well-known reactions described in literatures or magazines such as Organic Synthesis, Organic Reactions and Shin Zikken Kagaku Koza. Typical routes of synthesis will be described with reference to the following reaction formulas.

In the following reaction formulas, each of MSG1 through MSG5 independently represents a residual group of an organic compound; Hal represents Cl, Br or I; ring A represents trans-1,4-cyclohexylene group, 1,4-phenylene group in which one or more hydrogen on the six-member ring may be substituted by halogen, pyrimidine-2,5-diyl group, pyridine-2,5-diyl group, 1,3-dioxane-2,5-diyl group, tetrahydropyrane-2,5-diyl group, 1,3-dithiane-2,5-diyl group or tetrahydrothiopyrane-2,5-diyl group; $Q^1$ represents hydrogen, an alkyl group having 1 to 13 carbon atoms in which each of optional nonadjacent methylene groups may be substituted by oxygen or an alkenyl group having 2 to 13 carbon atoms; and p represents 0 or 1.

In order to introduce an alkenyl group into a molecule, the following method can be used. That is, Wittig's reagent (12) is allowed to react with a ketone derivative or an aldehyde derivative (11) in the presence of a base such as sodium methylate, potassium-t-butoxide (t-BuOK), and butyl lithium, in an ether-based solvent such as tetrahydrofuran (abbreviated as THF) or diethyl ether to form a compound (13). When $Q^1$ is an alkyl group or an alkenyl group described above, a trans-type isomer (14) can be formed by isomerizing the compound (13) with a benzenesulfinate or p-toluenesulfinate.

In order to introduce an alkenyl group of a desired chain length in a molecule, the following method can be used. In the same manner as described above, Wittig's reagent (16) is allowed to react with a ketone derivative (15) in an ether-based solvent in the presence of a base to form a compound (17). Next, the compound (17) is allowed to react with a mineral acid such as hydrochloric acid or sulfuric acid, or an organic acid such as formic acid or p-toluene sulfonic acid to form an aldehyde derivative (18).

Furthermore, in the same manner as described above, Wittig's reagent (20) is allowed to react with a ketone derivative (19) in the presence of a base to form a compound (21). Next, the compound (21) is subjected to hydrogen reduction in a toluene/Solmix mixed solvent in the presence of a metallic catalyst such as palladium/carbon or Raney nickel, and is allowed to react with a mineral acid such as hydrochloric acid or sulfuric acid, or an organic acid such as formic acid or p-toluene sulfonic acid to form an aldehyde derivative (22) These processes may be repeated as required.

The thus-obtained aldehyde derivative (18) or aldehyde derivative (22) is subjected to the same procedures for obtaining the compound (14) from the aldehyde derivative (11) to form a compound having an alkenyl group of a desired chain length.

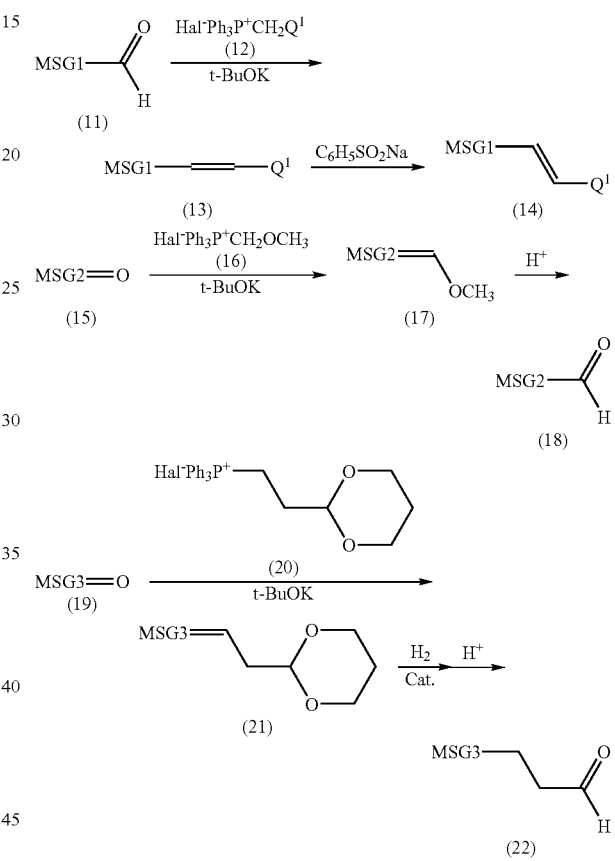

Hal = Cl, Br, I
$Q^1$ = H, alkyl, alkenyl

In order to introduce 2,3-difluoro-1,4-phenylene group in a molecule, the following reactions can be utilized.

When 2,3-difluoro-1,4-phenylene group is introduced into a benzene derivative MSG4 at the 4-position, a difluorobenzene derivative (31) is sequentially allowed to react with n-butyl lithium or sec-butyl lithium, then with zinc chloride, in an ether-based solvent such as THF and diethyl ether, and further subjected to a coupling reaction with 2,3-difluoro-1-bromobenzene in the presence of a metallic catalyst of palladium (0) to form a compound (32).

When a 2,3-difluoro-1,4-phenylene group is introduced into the ketone site of a cyclohexanone derivative having MSG4 at the 4-position, the cyclohexanone derivative (33) is allowed to react with a Grignard reagent (34) to cause a Grignard reaction, dehydrated in the presence of an acid catalyst, and subjected to hydrogen reduction to form a compound (35).

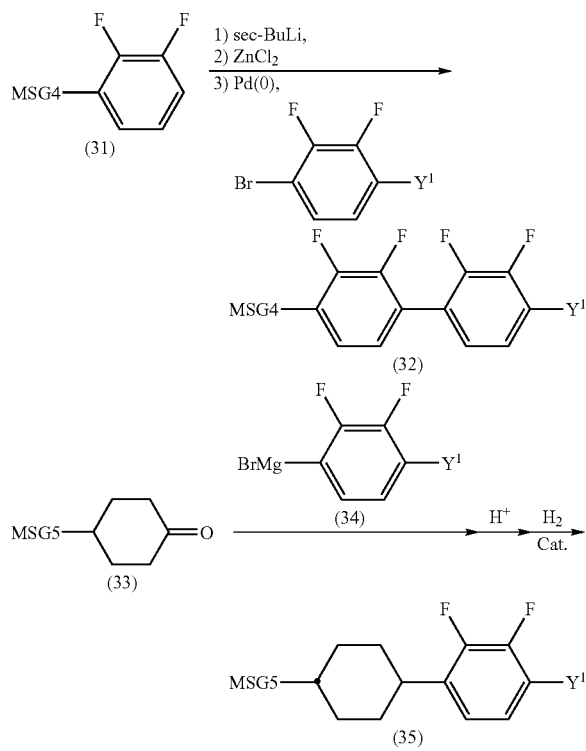

Compounds represented by general formula (1) in which rings $A^1$, $A^2$ and $A^3$ are silacyclohexane rings can be prepared by methods disclosed in Japanese Patent Application Laid Open Nos. 7-70148, 7-112990, and 7-149770; that is, a method in which a silacyclohexane compound is subjected to a coupling reaction with a corresponding organic metal reagent, or a method in which a metal is allowed to react with a compound having both a corresponding silane site and a halogen site to cause reaction in which a silicon-carbon bond is formed within the molecule.

The compound (1) described in the present application can be formed by appropriate selection of the above reactions.

EXAMPLES

The present invention will be described in further detail referring to examples; however, the present invention is by no means limited by these examples. The structures of compounds were identified by nuclear magnetic resonance spectrometry or mass spectrometry (abbreviated as MS). In these examples, $M^+$ in MS represents the molecular ion peak, C represents the crystal phase, $S_A$ the smectic A phase, $S_B$ the smectic B phase, N the nematic phase, Iso the isotropic liquid phase, and ( ) indicate the monotropic liquid crystal phase. All phase transition temperatures are expressed in terms of ° C.

Example 1

Synthesis of 2,3-difluoro-1-ethoxy-4-(trans-4-(3-butenyl)-cyclohexyl) benzene (compound (No. 8) represented by general formula (1) in which each of $R^1$ and $X^1$ is hydrogen, ring $A^1$ is trans-1,4-cyclohexylene group, $Y^1$ is ethoxy group, 1 is 2, and each of m and n is 0)

Step 1
Under a nitrogen flow, 141 mmol of 1-ethoxy-2,3-difluorobenzen was dissolved in 200 ml of THF, and the resultant solution was cooled to −70° C. While the same temperature was maintained, 130 ml of sec-butyl lithium (1.3 M, cyclohexane solution) was added dropwise, and the resultant solution was stirred for 1 hour at the same temperature. A solution of 128 mmol of 1,4-cyclohexanedione monoethylene acetal dissolved in 200 ml of THF was added dropwise while the same temperature was maintained, and the resultant solution was further stirred for 1 hour at the same temperature. The reaction temperature was then gradually elevated to room temperature, after which the solution was stirred for 2 hours at room temperature. The reaction was terminated by gradual addition of the reaction mixture into 500 ml of water. The water layer was extracted by 500 ml of toluene, and the organic layer was washed with 500 ml of water three times and dried over anhydrous magnesium sulfate. The solvent was distilled off under reduced pressure, the residue was dissolved in 300 ml of toluene, 1.5 g of p-toluenesulfonic acid monohydride was added, and the solution was heated to reflux for 1 hour. The organic layer was washed three times with 300 ml of water, and dried over anhydrous magnesium sulfate. The solvent was distilled off under reduced pressure, the residue was subjected to silica gel column chromatography (eluent: a mixed solvent of ethyl acetate/toluene=3/7), and the solvent was distilled off under reduced pressure. The residue was dissolved in 200 ml of a mixed solvent of toluene/ethanol (1/1), 4.0 g of 5-wt %-palladium/carbon catalyst, and the solution was stirred for 6 hours at room temperature under a hydrogen pressure of 1–2 kg/cm$^2$. After the catalyst was filtered off, the solvent was distilled off from the filtrate under reduced pressure, the residue was subjected to silica gel column chromatography (eluent: ethyl acetate/toluene=3/7), and the solvent was distilled off under reduced pressure, to form crude 4-(2,3-difluoro-4-ethoxyphenyl)-cyclohexane monoethylene acetal.

Step 2
Crude 4-(2,3-difluoro-4-ethoxyphenyl)-cyclohexanone monoethylene acetal (50.3 mmol) obtained in Step 1 was dissolved in 200 ml of toluene, 87% formic acid (503 mmol) was added, and the solution was heated to reflux for 4 hours. The reaction solution was washed twice with 100 ml of a saturated aqueous solution of sodium hydrogen carbonate, then three times with 100 ml of water, and dried over anhydrous magnesium sulfate. The solvent was distilled off under reduced pressure, to form crude 4-(2,3-difluoro-4-ethoxyphenyl)-cyclohexanone (50.3 mmol).

Step 3
A mixture of 2-(1,3-dioxane-2-yl)-ethyltriphenyl phosphonium bromide (60.4 mmol) and 30 ml of THF was cooled down to −30° C. by use of a refrigerant under a nitrogen flow. To this mixture, t-BuOK (60.4 mmol) was added, and the mixture was stirred for one hour. A solution of the crude 4-(2,3-difluoro-4-ethoxyphenyl)-cyclohexanone (50.3 mmol) dissolved in 100 ml of THF was added dropwise to this mixture while temperature was maintained at −30° C. or below. After completion of the addition, the reaction temperature was gradually elevated to room temperature, and the mixture was stirred for 2 hours. The reaction mixture was filtered with celite, the solvent was distilled off under reduced pressure, the residue was subjected to silica gel column chromatography (eluent: a mixed solvent of ethyl acetate/toluene=3/7), the solvent was distilled off under reduced pressure, and the product was re-crystallized from heptane to form 2-(2-(4-(2,3-difluoro-4-ethoxyphenyl)cyclohexylidene)-ethyl)-1,3-dioxane (36.9 mmol).

Step 4

The 2-(2-(4-(2,3-difluoro-4-ethoxyphenyl)cyclohexylidene)-ethyl)-1,3-dioxane (36.9 mmol) obtained by the reaction of Step 3 was dissolved in 100 ml of a mixed solvent of toluene/ethanol (1/1), 4.0 g of 5-wt %-palladium/carbon catalyst was added, and the solution was stirred for 7 hours at room temperature under a hydrogen pressure of 1–2 kg/cm$^2$. After the catalyst was filtered off, the solvent was distilled off from the filtrate under reduced pressure, the residue was subjected to silica gel column chromatography (eluent: a mixed solvent of ethyl acetate/toluene=3/7), the solvent was distilled off under reduced pressure, and the product was re-crystallized from ethanol to form 2-(2-(trans-4-(2,3-difluoro-4-ethoxyphenyl)-cyclohexyl)-ethyl)-1,3-dioxane (36.9 mmol).

Step 5

The 2-(2-(trans-4-(2,3-difluoro-4-ethoxyphenyl)-cyclohexyl)-ethyl)-1,3-dioxane (19.8 mmol) obtained by the reaction of Step 4 was dissolved in 100 ml of toluene, 87% formic acid (198 mmol) was added, and the solution was heated to reflux for 4 hours. The reaction solution was twice washed with 50 ml of a saturated aqueous solution of sodium hydrogen carbonate, then three times with 50 ml of water, and dried over anhydrous magnesium sulfate. The solvent was distilled off under reduced pressure, to form crude 3-(trans-4-(2,3-difluoro-4-ethoxyphenyl)-cyclohexyl)-propanal (19.8 mmol).

Step 6

A mixture of methyltriphenyl phosphonium bromide (23.8 mmol) and 50 ml of THF was cooled to −30° C. by use of a refrigerant under a nitrogen flow. To this mixture, t-BuOK (23.8 mmol) was added and the mixture was stirred for one hour. A solution of the crude 3-(trans-4-(2,3-difluoro-4-ethoxyphenyl)-cyclohexyl)-propanal (19.8 mmol) and dissolved in 50 ml of THF was added dropwise to this mixture while temperature was maintained at −30° C. or below. After the addition was completed, the reaction temperature was gradually elevated to room temperature, and the mixture was stirred for 2 additional hours. The reaction mixture was filtered with celite, the solvent was distilled off under reduced pressure, the residue was subjected to silica gel column chromatography (eluent: a mixed solvent of ethyl acetate/heptane=1/1), the solvent was distilled off under reduced pressure, and the product was re-crystallized from ethanol to form the target compound (9.51 mmol).

Various spectra confirmed the structure of this product.

MS:m/e=294 (M$^+$)

Phase transition temperature: C 39.4 Iso

In the similar processes as with Example 1, the following compounds can be prepared.

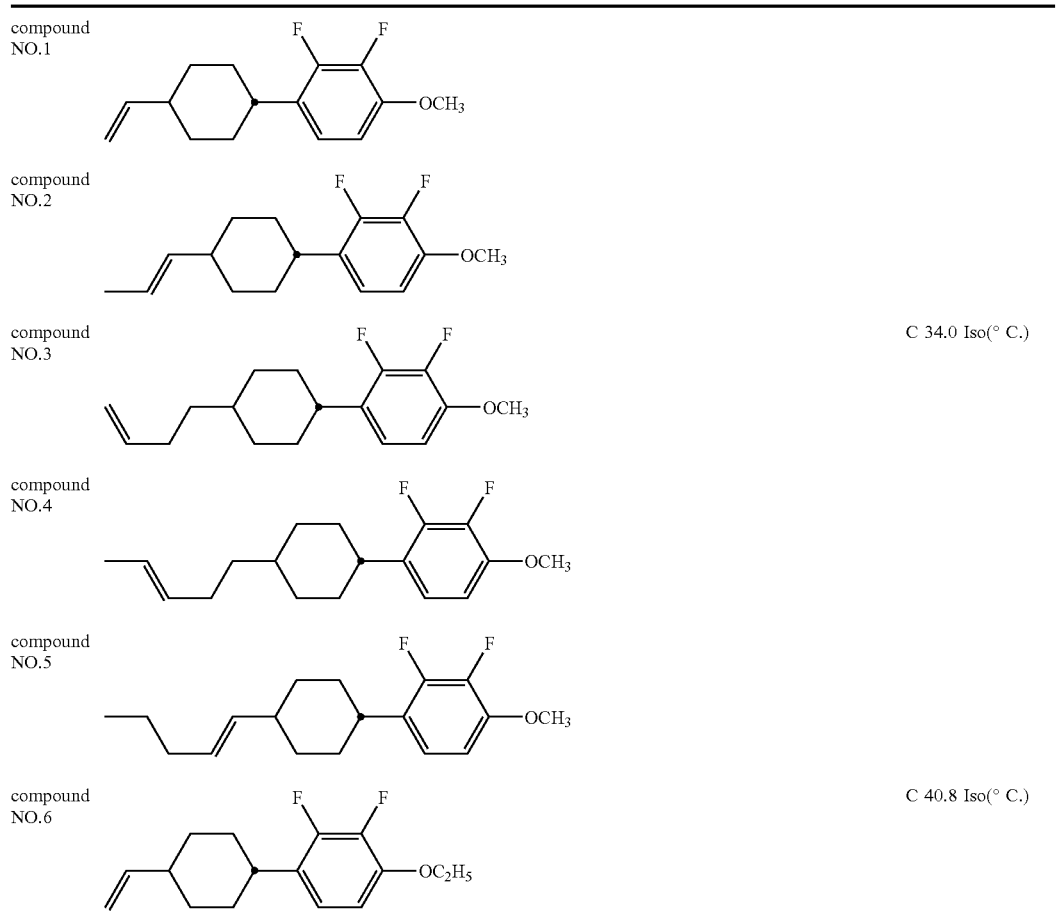

-continued
compound NO.7
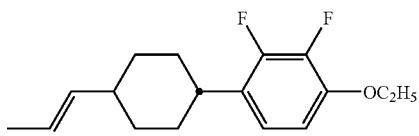
compound NO.8
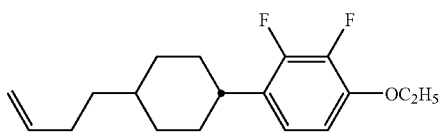
C 39.4 Iso(° C.)
compound NO.9
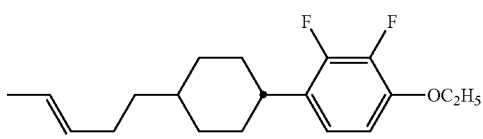
compound NO.10
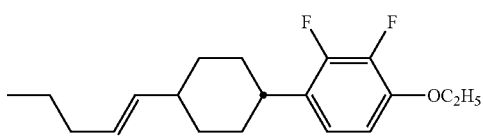
compound NO.11
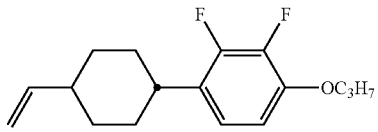
C 27.1 Iso(° C.)
compound NO.12
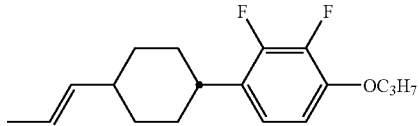
compound NO.13
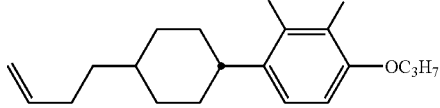
C 22.7 Iso(° C.)
compound NO.14
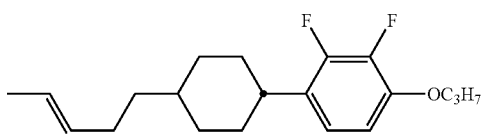
compound NO.15
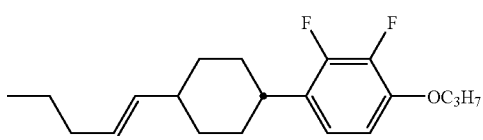
compound NO.16
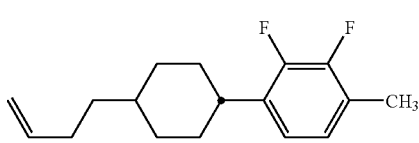
compound NO.17
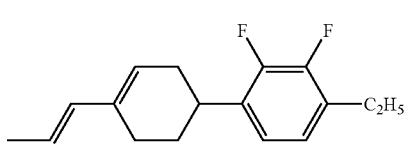

-continued
compound NO.18
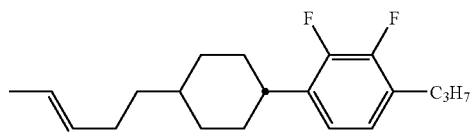
compound NO.19
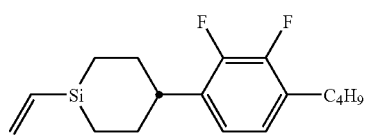
compound NO.20
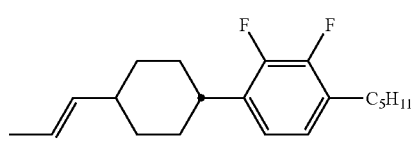
compound NO.21
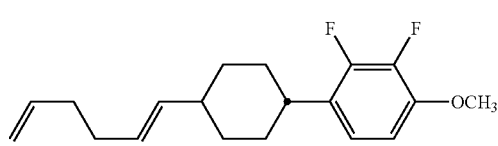
compound NO.22
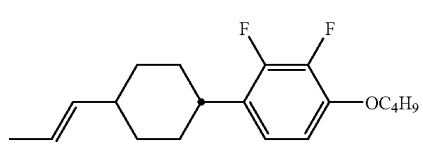
compound NO.23
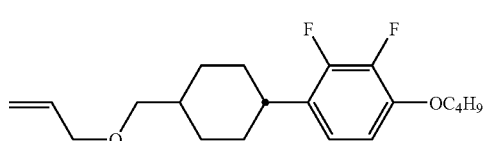
compound NO.24
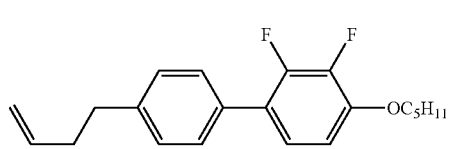
compound NO.25
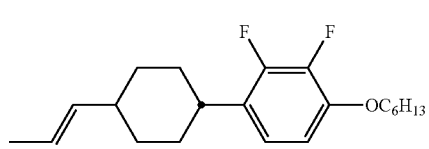
compound NO.26
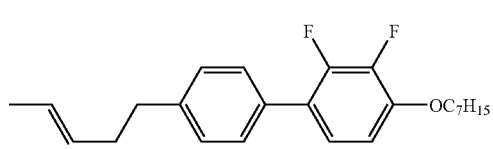
compound NO.27
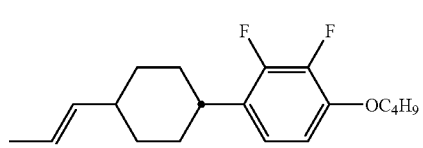
compound NO.28
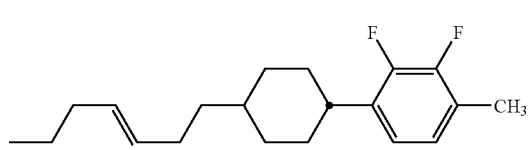

| | | |
|---|---|---|
| compound NO.29 | 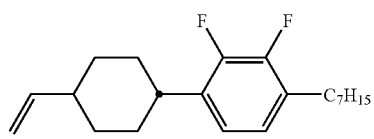 | |
| compound NO.30 | 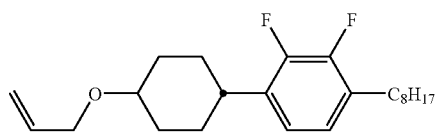 | |
| compound NO.31 | 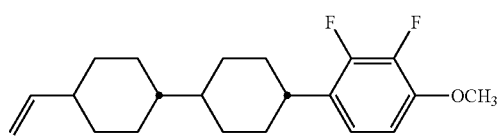 | C 86.7 N 162.8 Iso(° C.) |
| compound NO.32 | 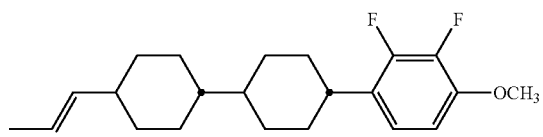 | |
| compound NO.33 | 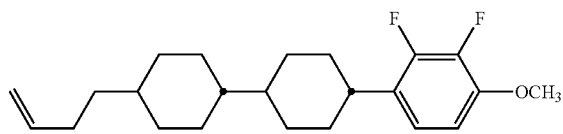 | C 76.8 ($S_B$ 62.0) N 172.0 Iso(° C.) |
| compound NO.34 | 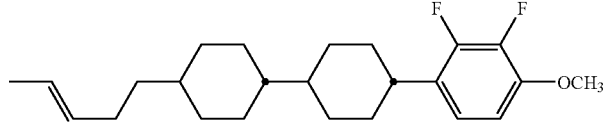 | |
| compound NO.35 | 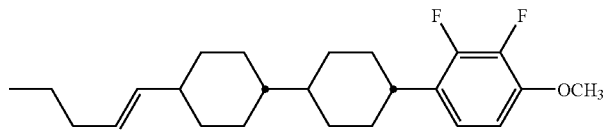 | |
| compound NO.36 | 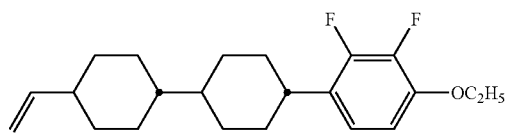 | C 80.6 N 169.2 Iso(° C.) |
| compound NO.37 | 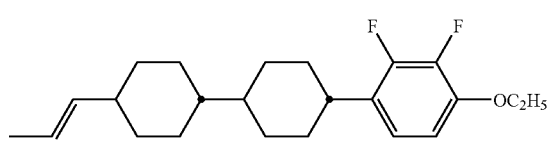 | |
| compound NO.38 | 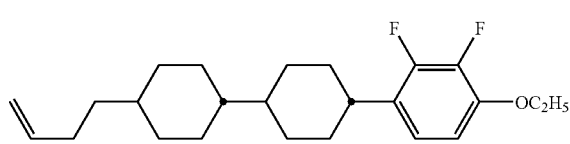 | C 80.0 ($S_B$ 71.8) N 184.8 Iso(° C.) |
| compound NO.39 | 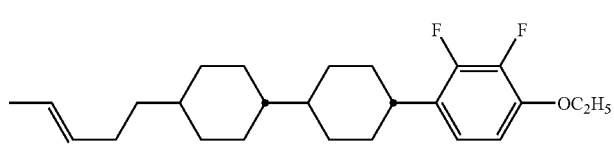 | |

-continued
compound NO.40
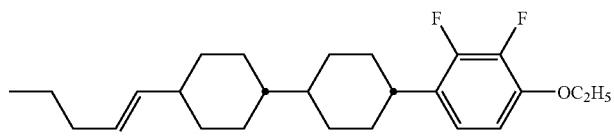
compound NO.41
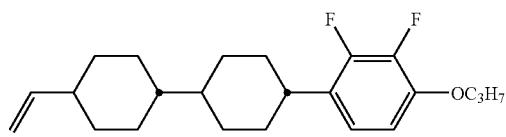
compound NO.42
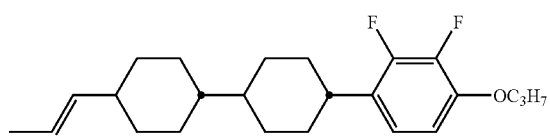
compound NO.43
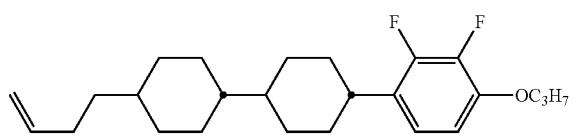
C 55.7 $S_B$ 98.3 N 172.5 Iso(° C.)
compound NO.44
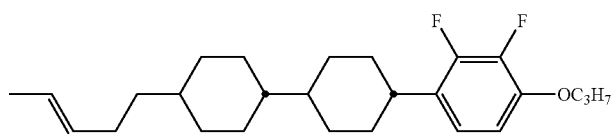
compound NO.45
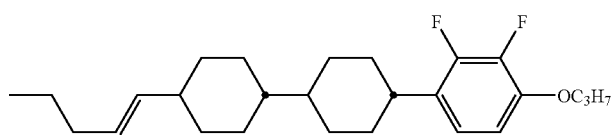
compound NO.46
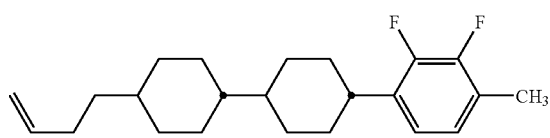
C 42.6 N 145.5 Iso(° C.)
compound NO.47
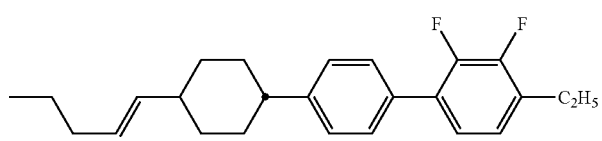
compound NO.48
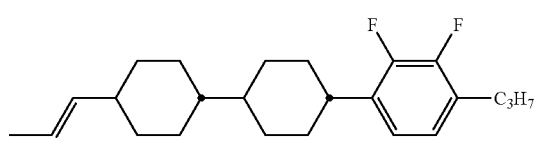
compound NO.49
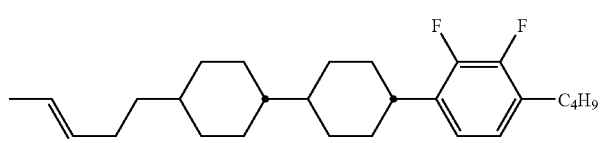
compound NO.50
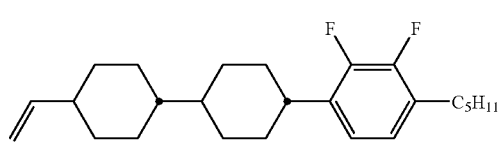

-continued
compound NO.51
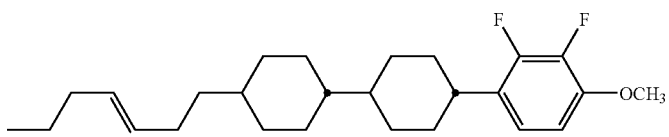
compound NO.52
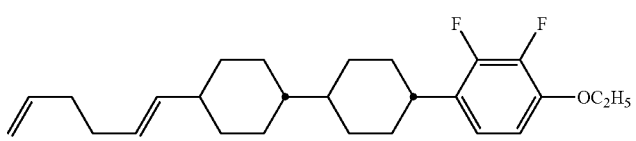
compound NO.53
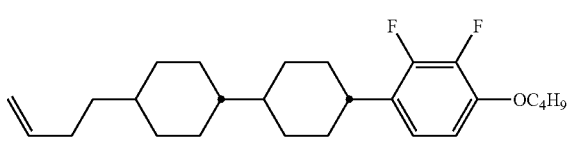
compound NO.54
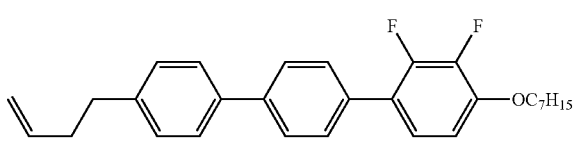
compound NO.55
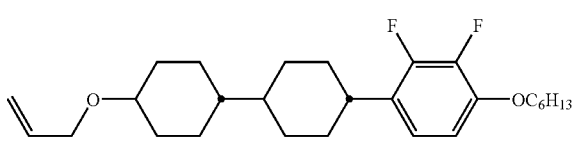
compound NO.56
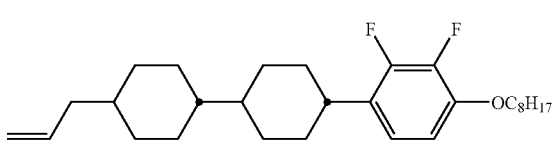
compound NO.57
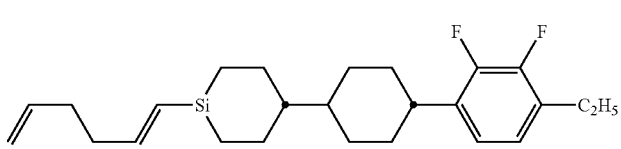
compound NO.58
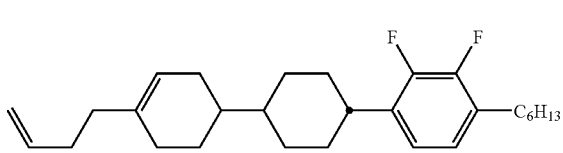
compound NO.59
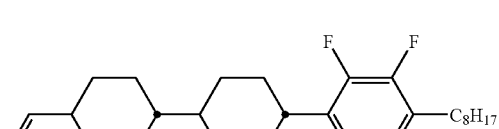
compound NO.60
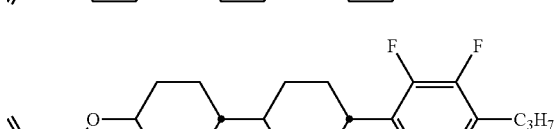
compound NO.61
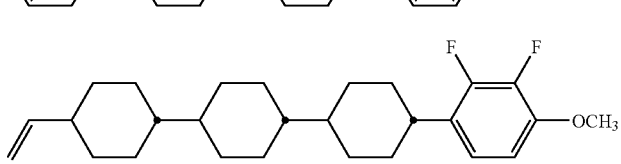

-continued
compound NO.62
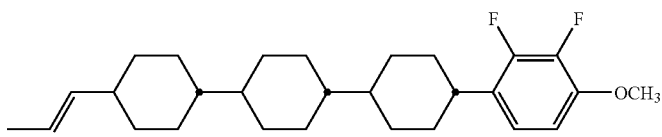
compound NO.63
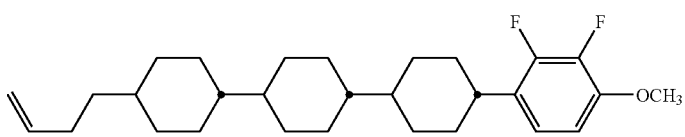
compound NO.64
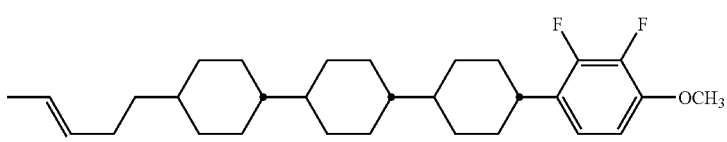
compound NO.65
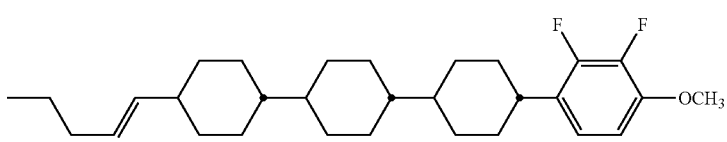
compound NO.66
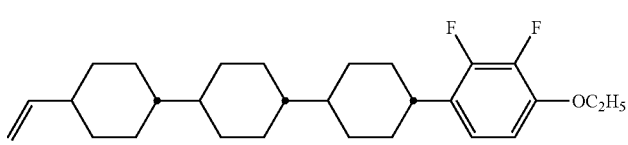
compound NO.67
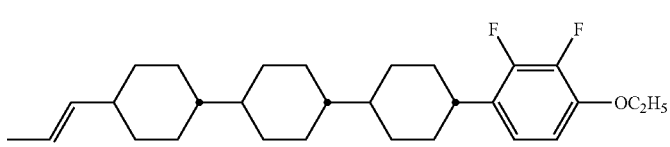
compound NO.68
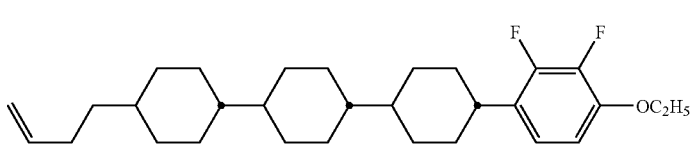
compound NO.69
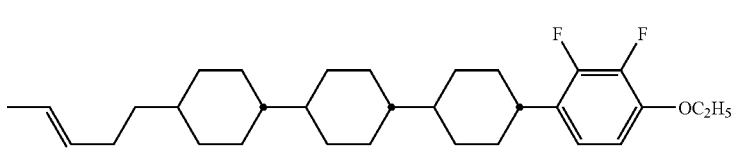
compound NO.70
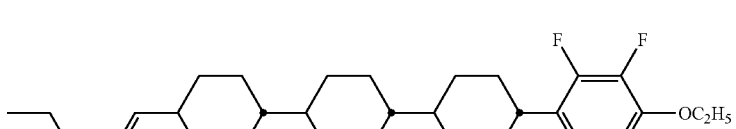
compound NO.71
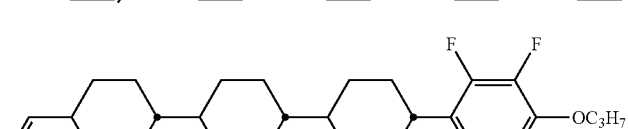
compound NO.72
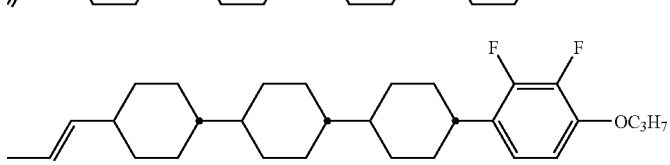

-continued
compound NO.73
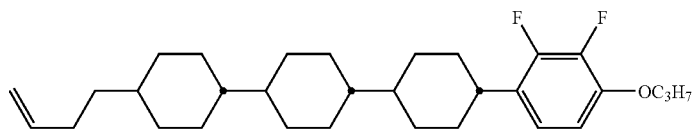
compound NO.74
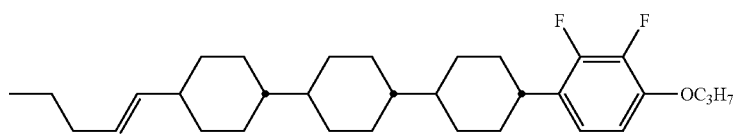
compound NO.75
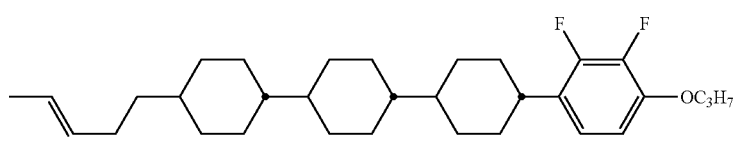
compound NO.76
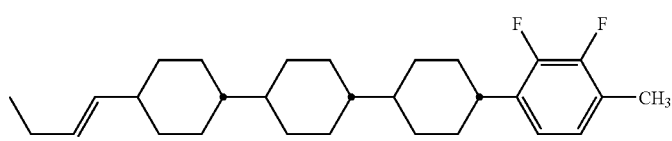
compound NO.77
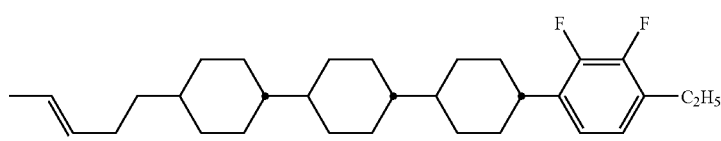
compound NO.78
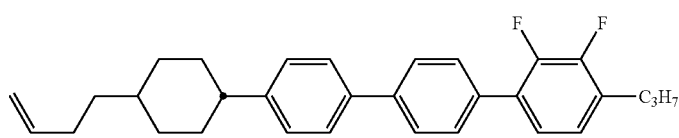
compound NO.79
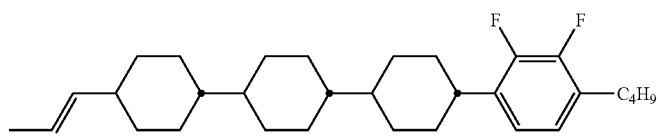
compound NO.80
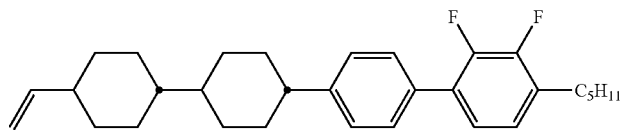
compound NO.81
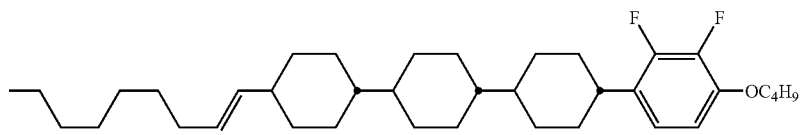
compound NO.82
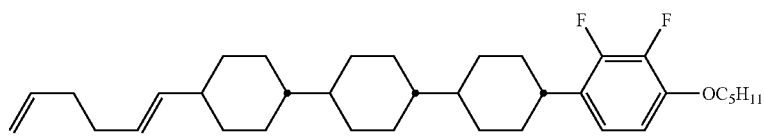
compound NO.83
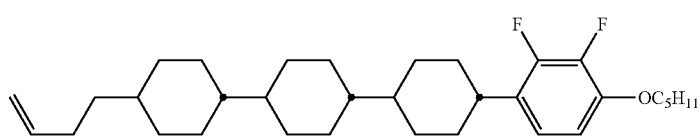

-continued
compound NO.84
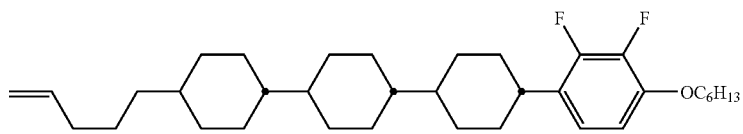
compound NO.85
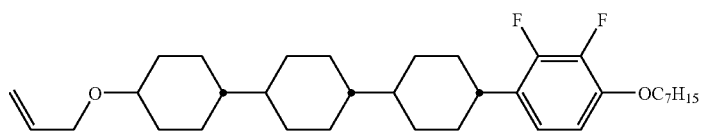
compound NO.86
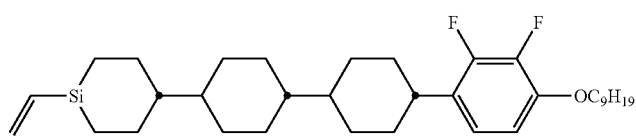
compound NO.87
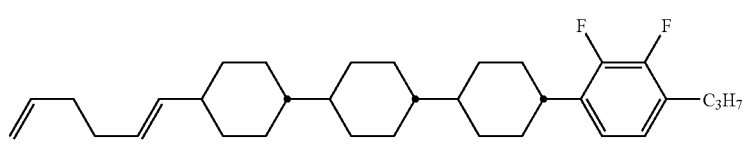
compound NO.88
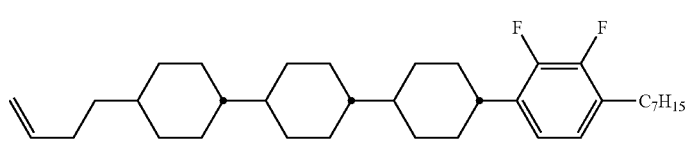
compound NO.89
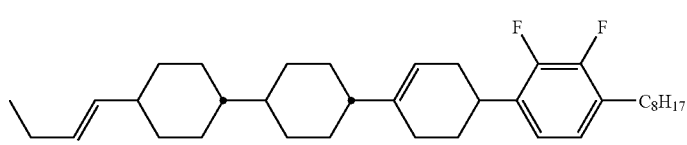
compound NO.90
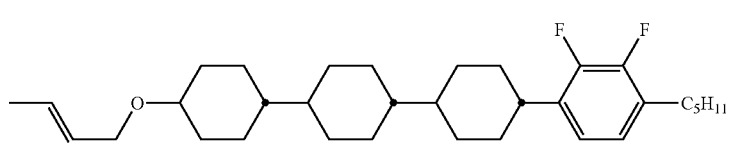
compound NO.91
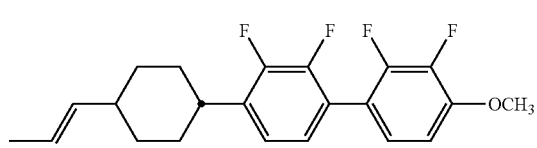
compound NO.92
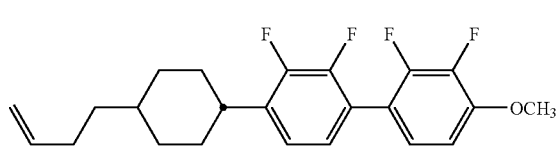
compound NO.93
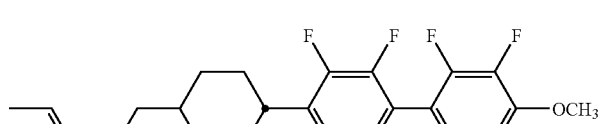
compound NO.94
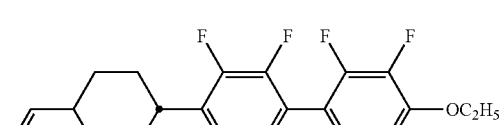

-continued
compound NO.95
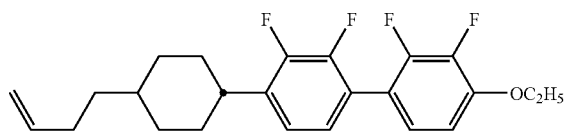
compound NO.96
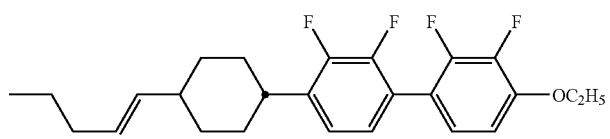
compound NO.97
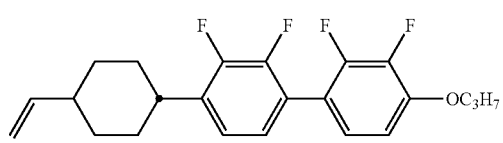
compound NO.98
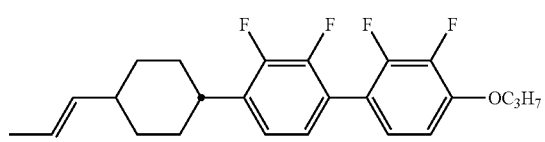
compound NO.99
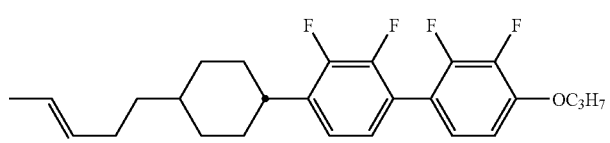
compound NO.100
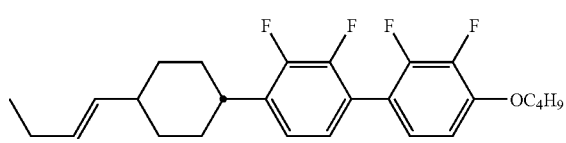
compound NO.101
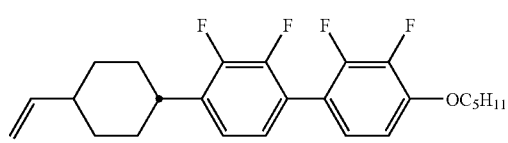
compound NO.102
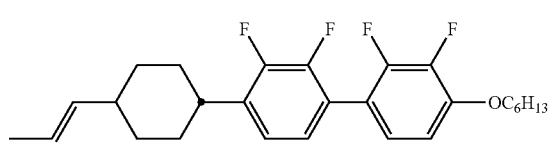
compound NO.103
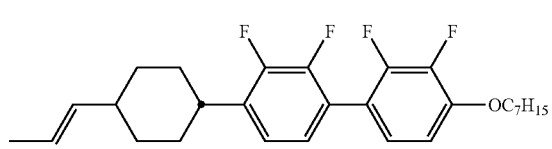
compound NO.104
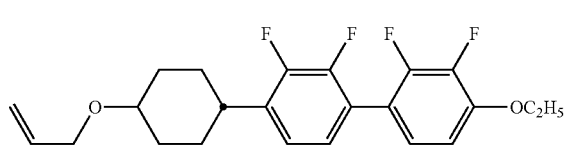
compound NO.105
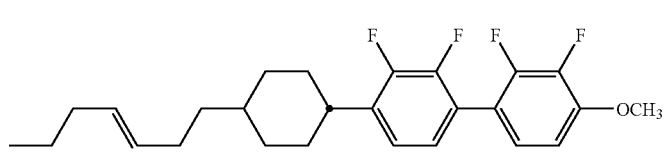

-continued
compound NO.106
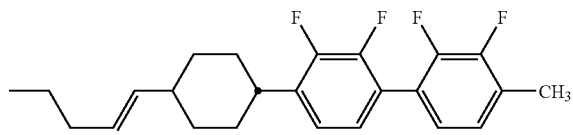
compound NO.107
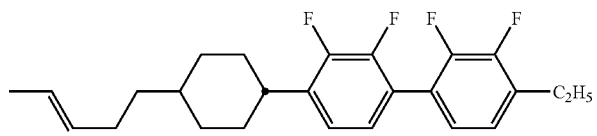
compound NO.108
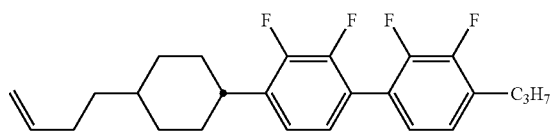
compound NO.109
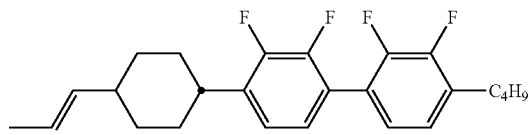
compound NO.110
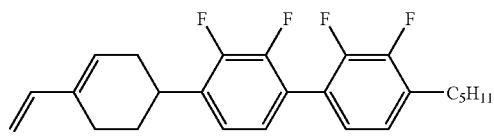
compound NO.111
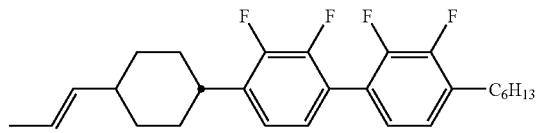
compound NO.112
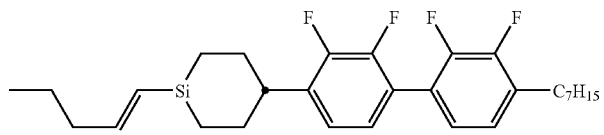
compound NO.113
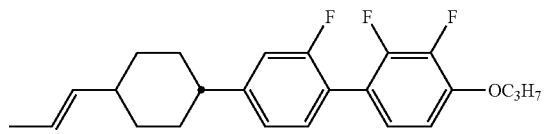
compound NO.114
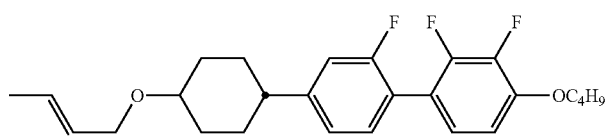
compound NO.115
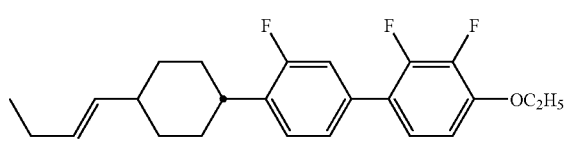
compound NO.116
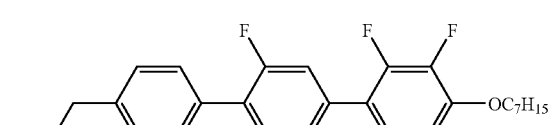

-continued
compound NO.117
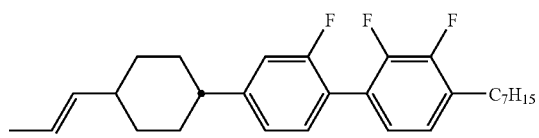
compound NO.118
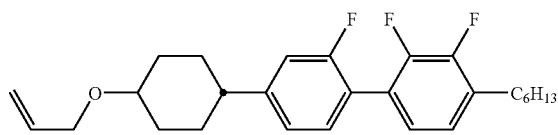
compound NO.119
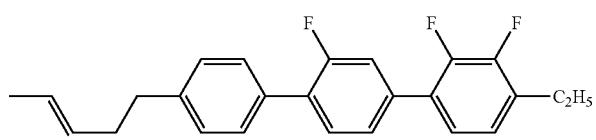
compound NO.120
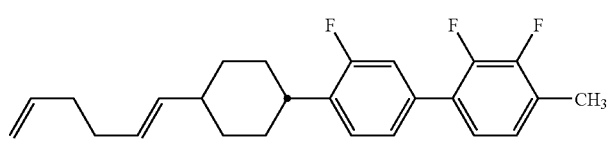
compound NO.121
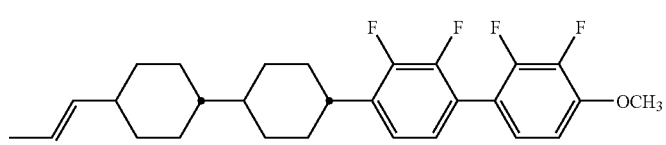
compound NO.122
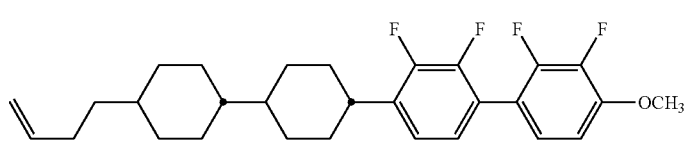
compound NO.123
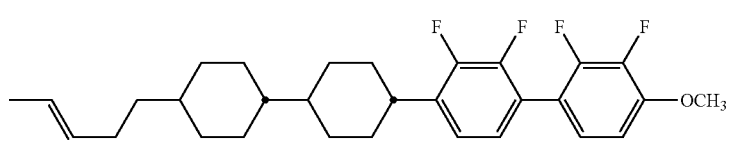
compound NO.124
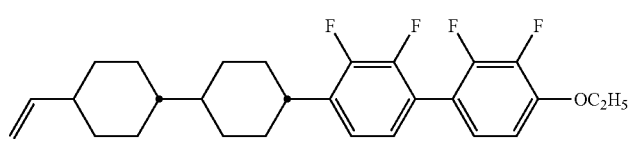
compound NO.125
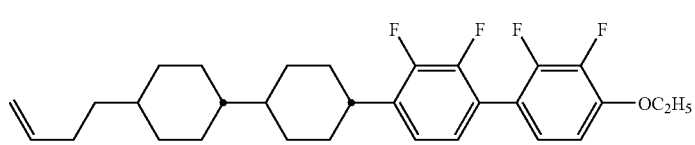
compound NO.126
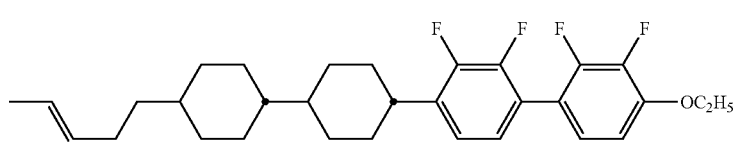
compound NO.127
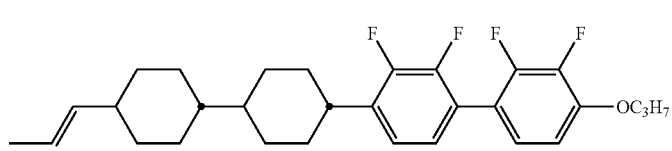

-continued
compound NO.128
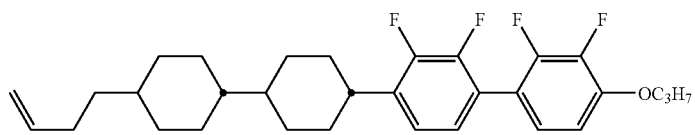
compound NO.129
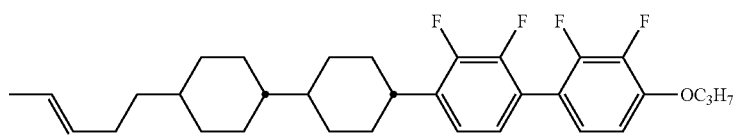
compound NO.130
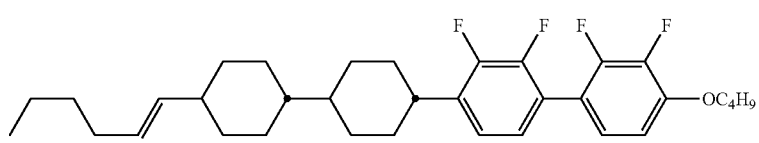
compound NO.131
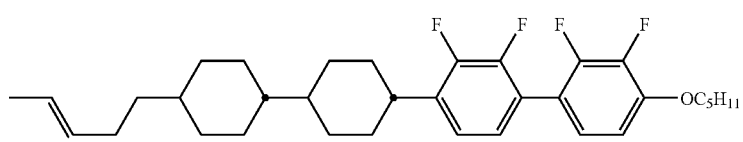
compound NO.132
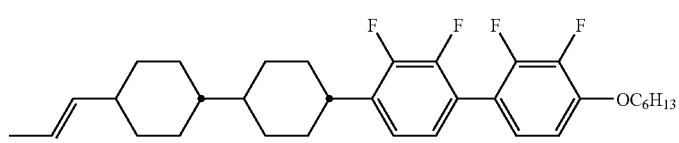
compound NO.133
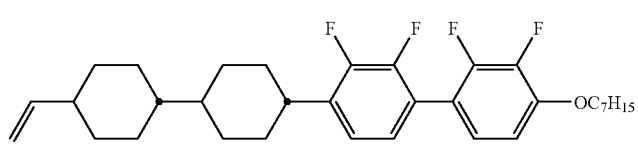
compound NO.134
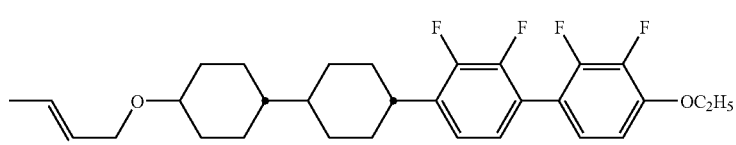
compound NO.135
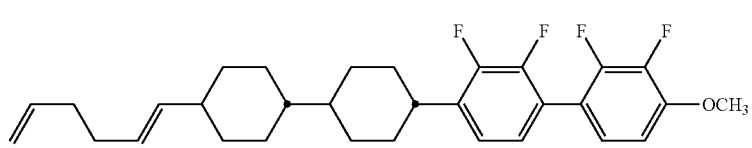
compound NO.136
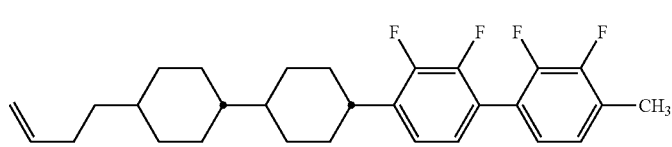
compound NO.137
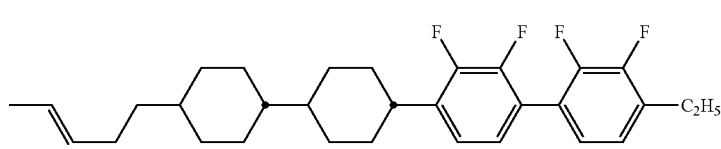
compound NO.138
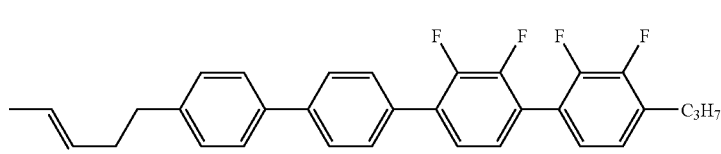

-continued
compound NO.139
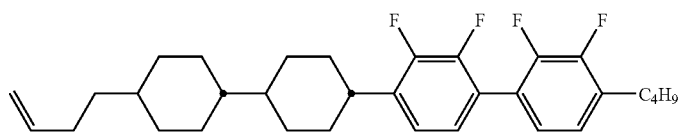
compound NO.140
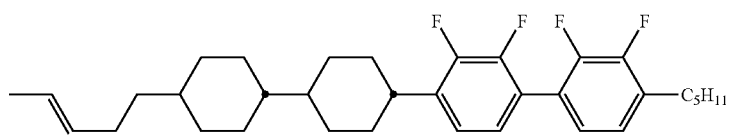
compound NO.141
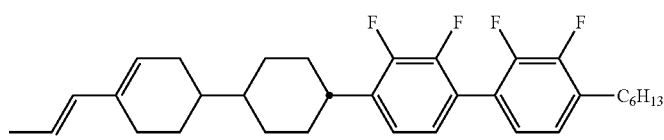
compound NO.142
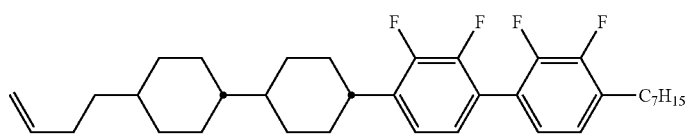
compound NO.143
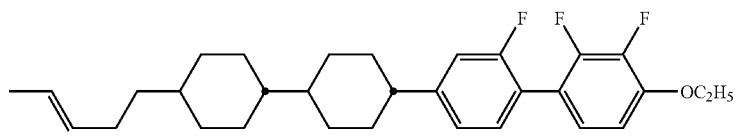
compound NO.144
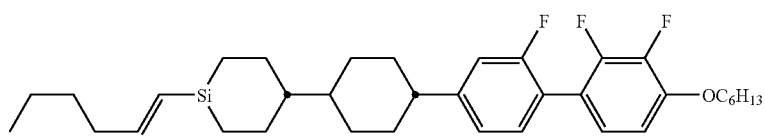
compound NO.145
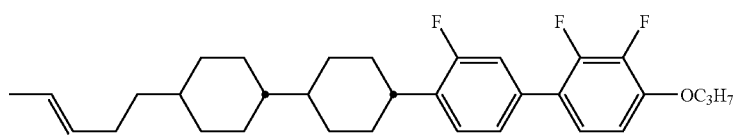
compound NO.146
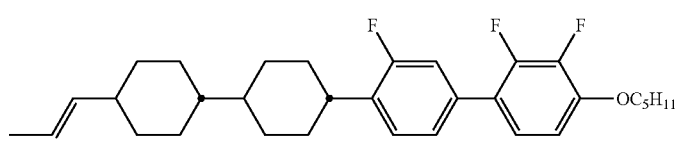
compound NO.147
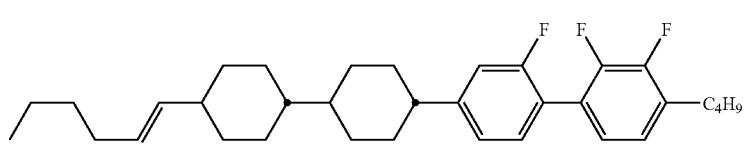
compound NO.148
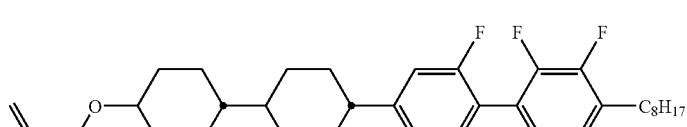
compound NO.149
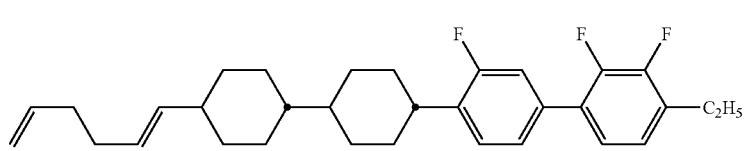

-continued
compound NO.150 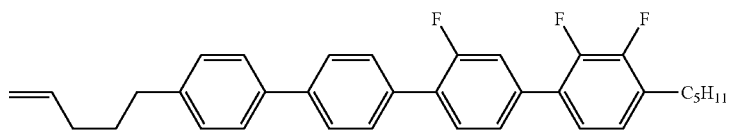
compound NO.151 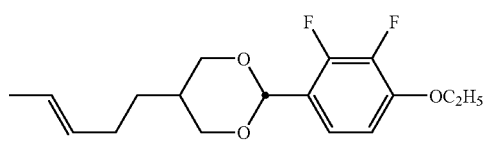
compound NO.152 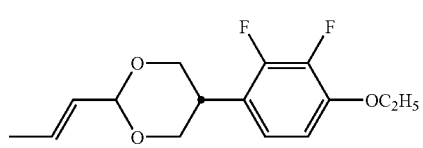
compound NO.153 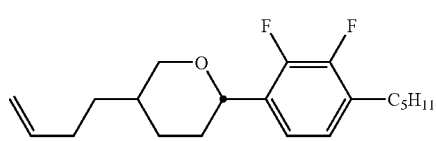
compound NO.154 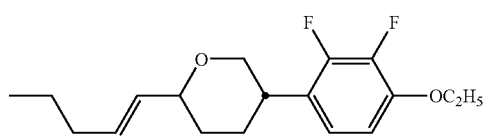
Compound NO.155 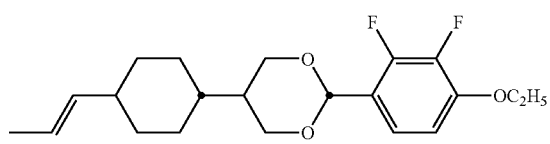
compound NO.156 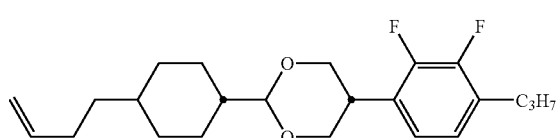
compound NO.157 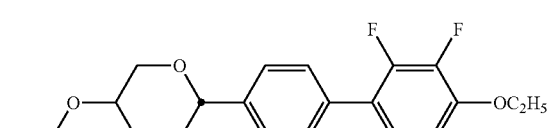
compound NO.158 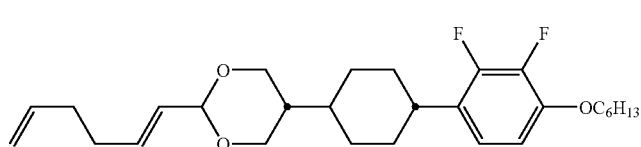
compound NO.159 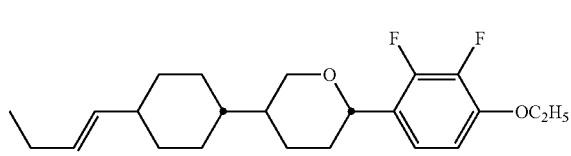
compound NO.160 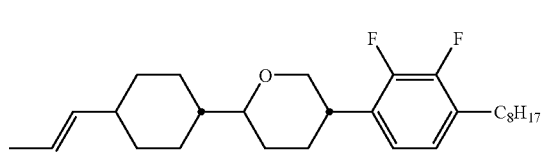

compound NO.161 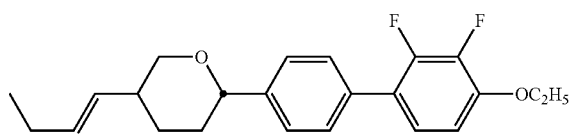
compound NO.162 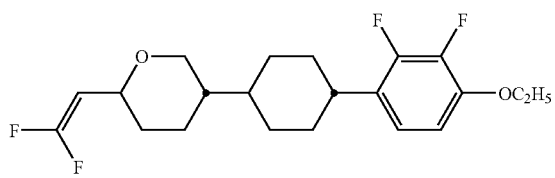
compound NO.163 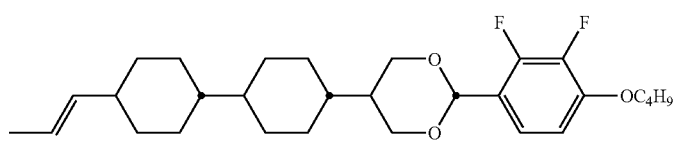
compound NO.164 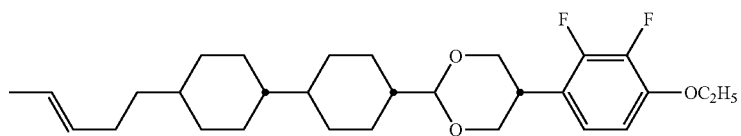
compound NO.165 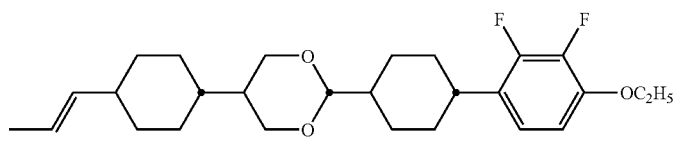
compound NO.166 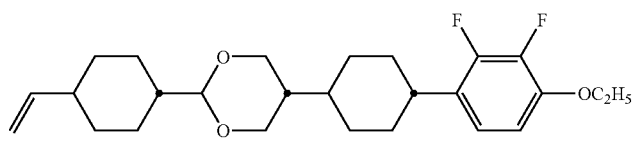
compound NO.167 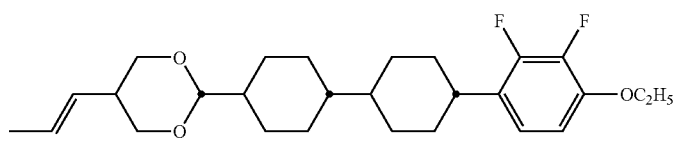
compound NO.168 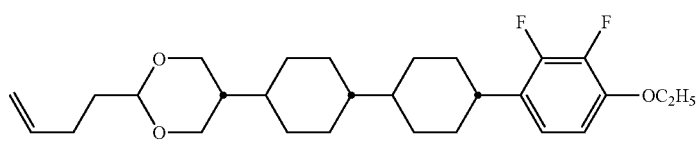
compound NO.169 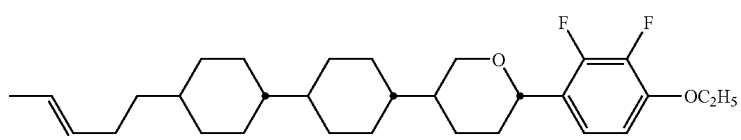
compound NO.170 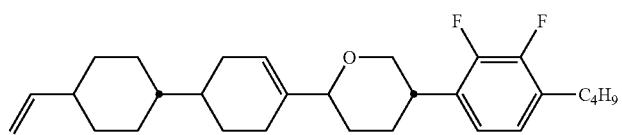

-continued
compound NO.171 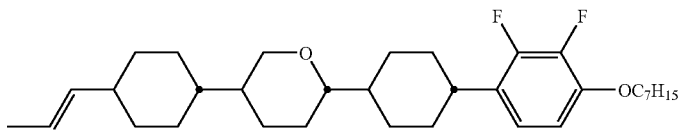
compound NO.172 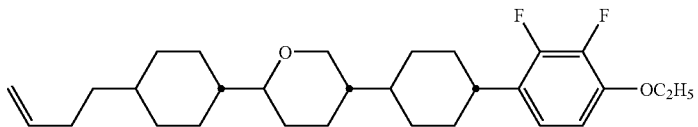
compound NO.173 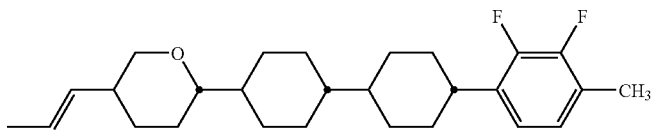
compound NO.174 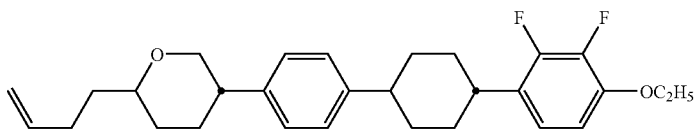
compound NO.175 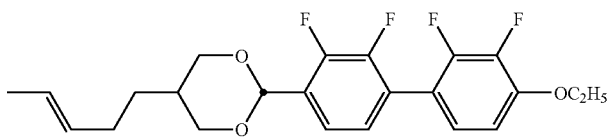
compound NO.176 
compound NO.177 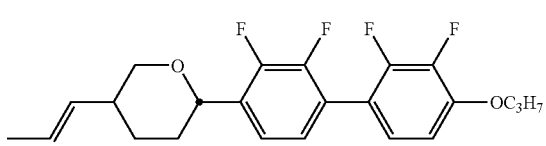
compound NO.178 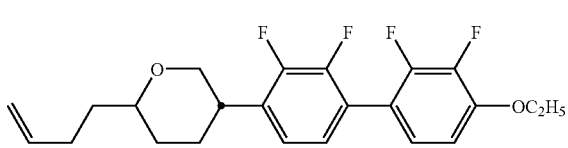
compound NO.179 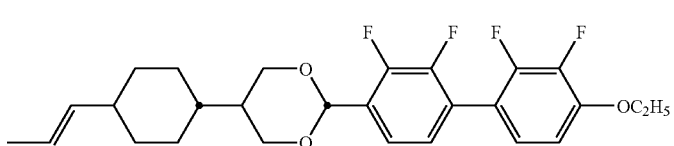
compound NO.180 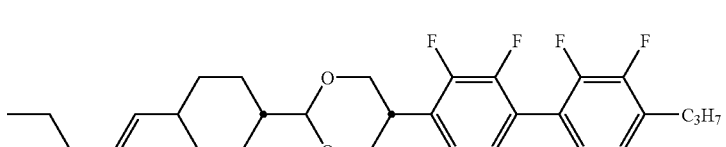
compound NO.181 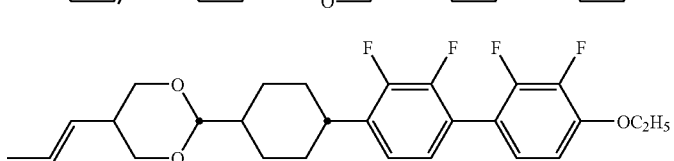

compound NO.182
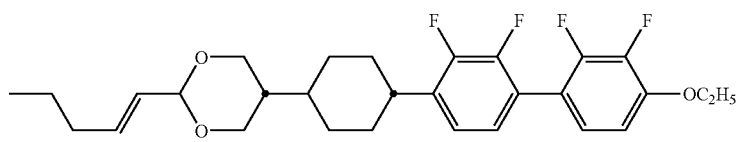
compound NO.183
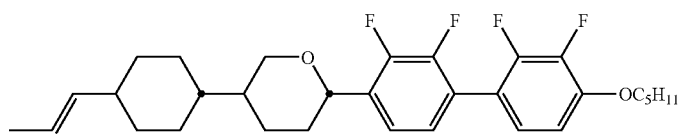
compound NO.184
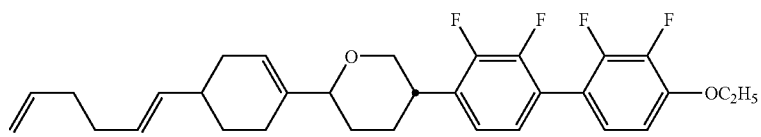
compound NO.185
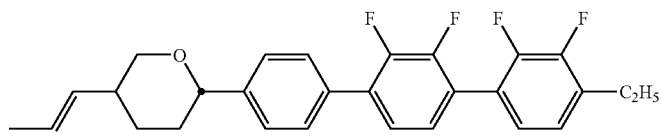
compound NO.186
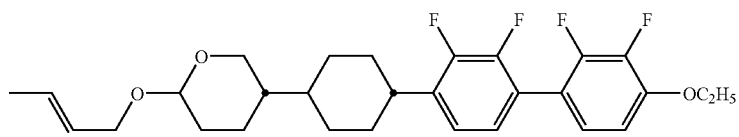
compound NO.187
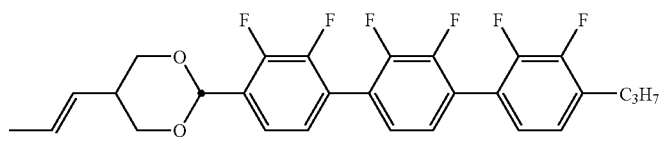
compound NO.188
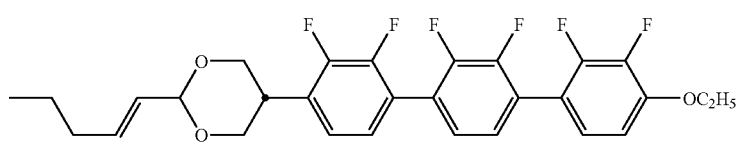
compound NO.189
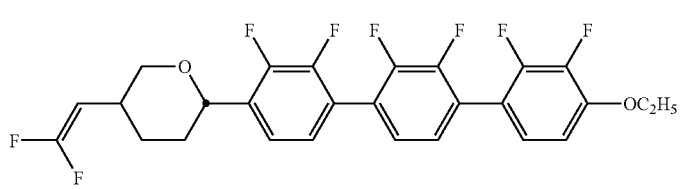
compound NO.190
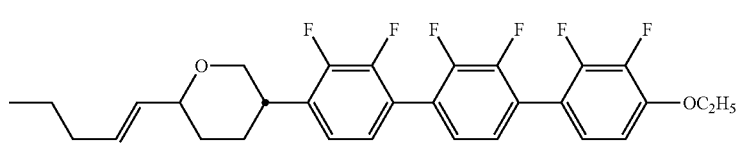
compound NO.191
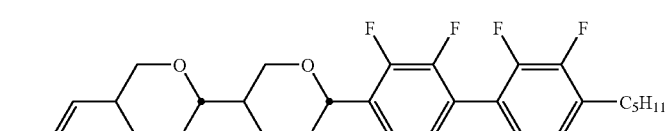

-continued
compound NO.192
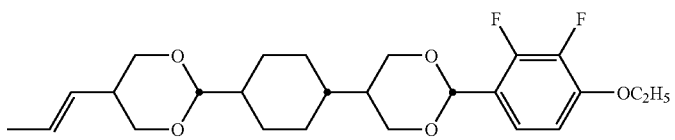
compound NO.193
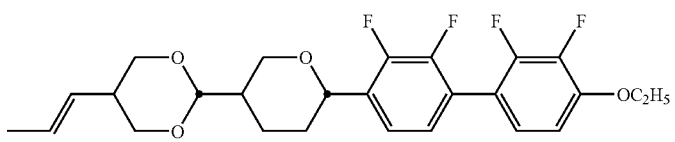
compound NO.194
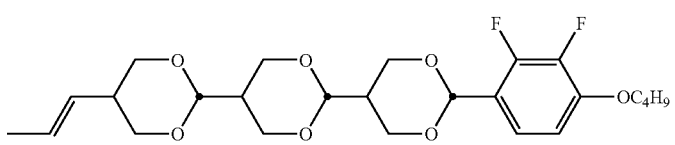
compound NO.195
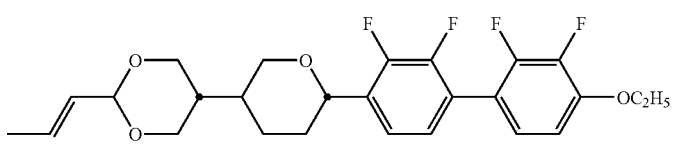
compound NO.196
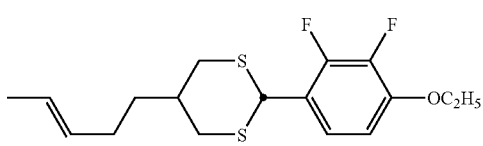
compound NO.197
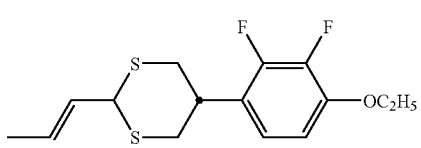
compound NO.198
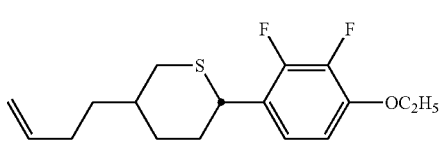
compound NO.199
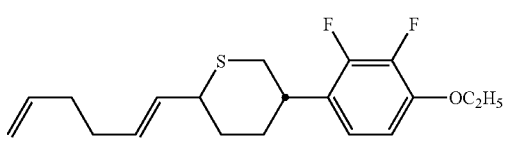
compound NO.200
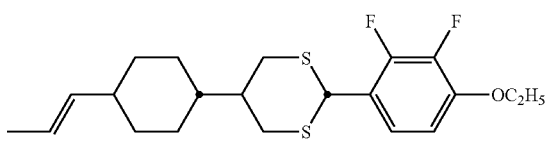
compound NO.201
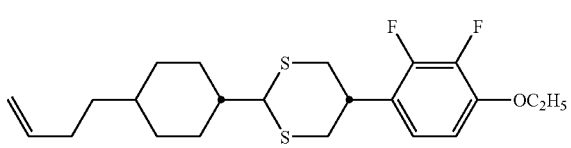
compound NO.202
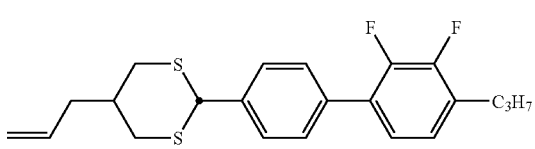

-continued
compound NO.203
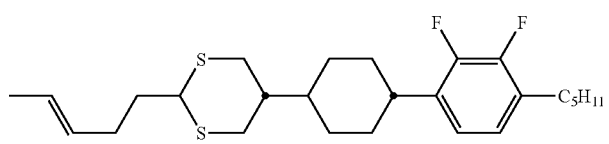
compound NO.204
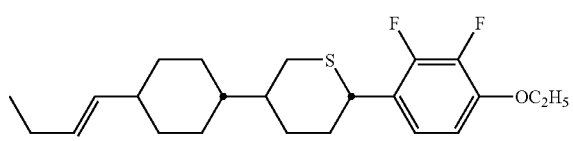
compound NO.205
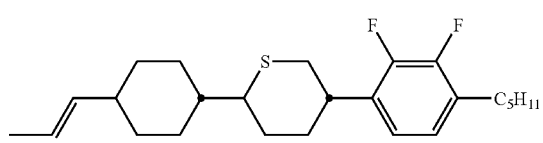
compound NO.206
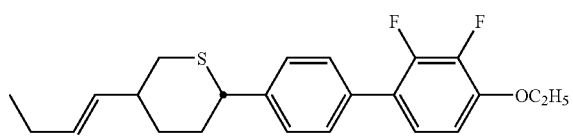
compound NO.207
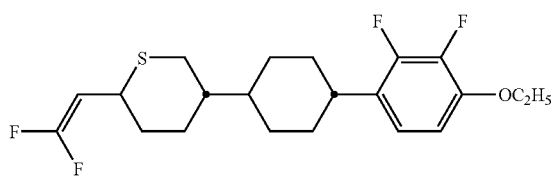
compound NO.208
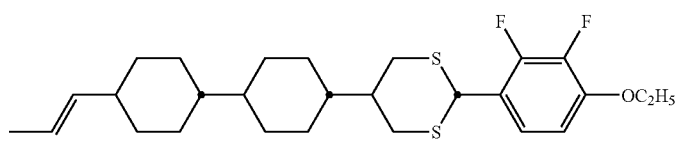
compound NO.209
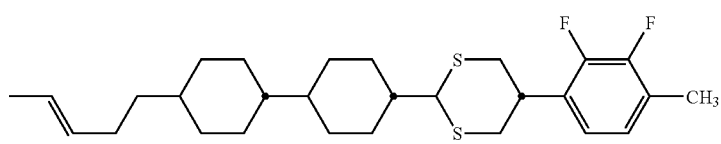
compound NO.210
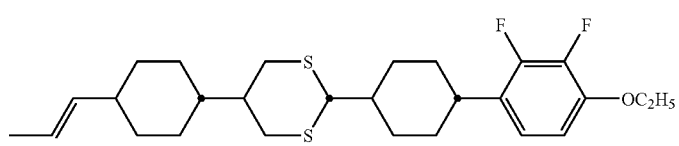
compound NO.211
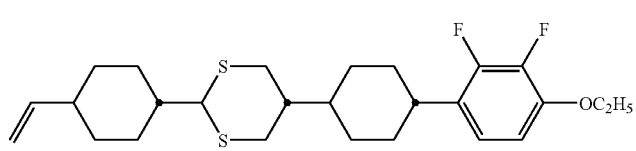
compound NO.212
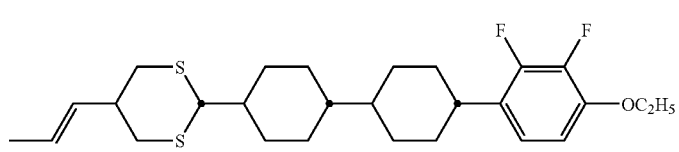

-continued
compound NO.213
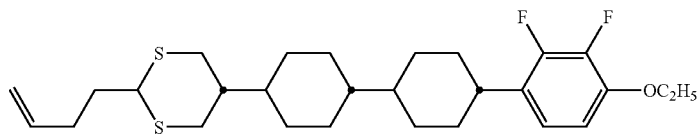
compound NO.214
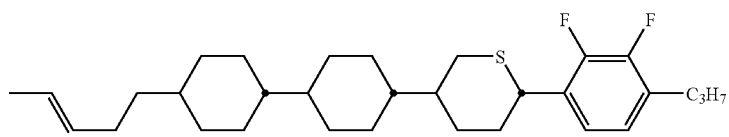
compound NO.215
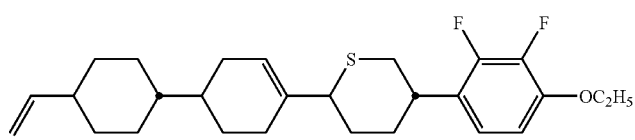
compound NO.216
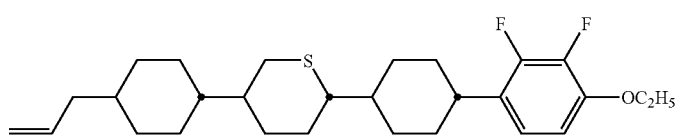
compound NO.217
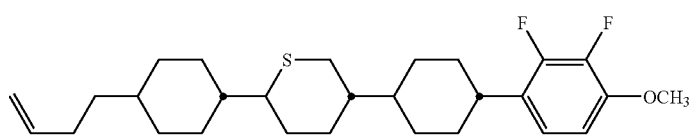
compound NO.218
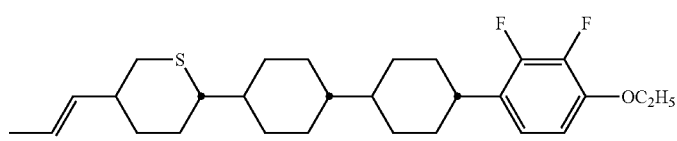
compound NO.219
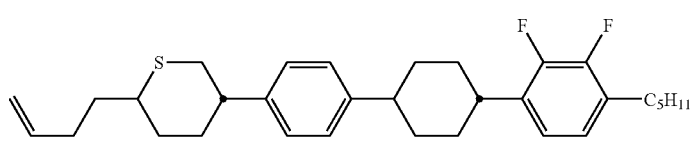
compound NO.220
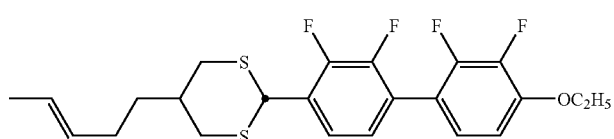
compound NO.221
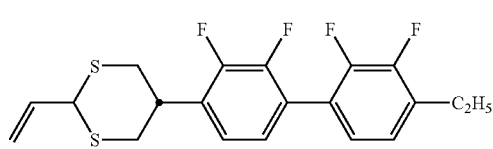
compound NO.222
compound NO.223
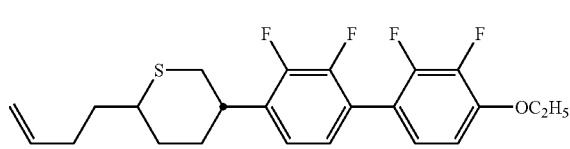

compound NO.224
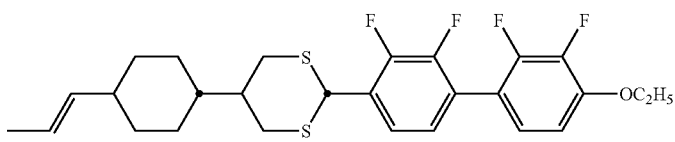
compound NO.225
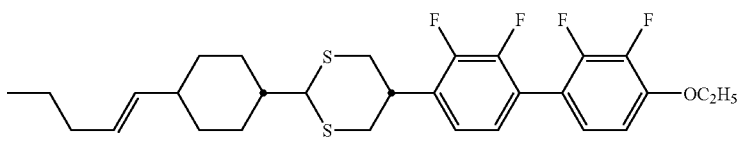
compound NO.226
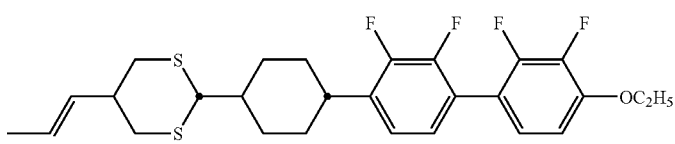
compound NO.227
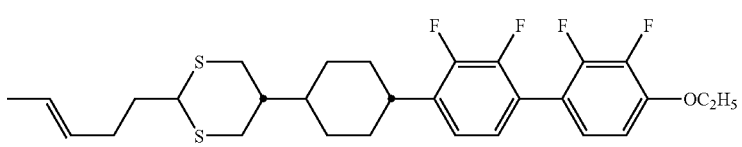
compound NO.228
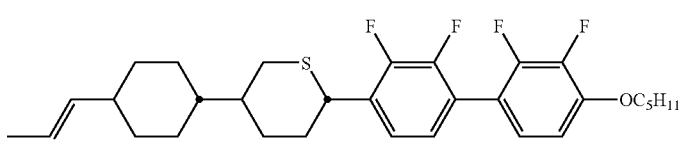
compound NO.229
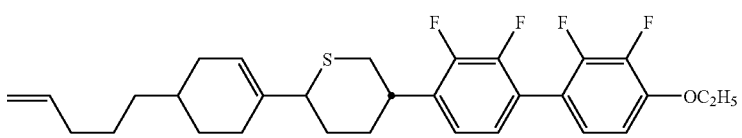
compound NO.230
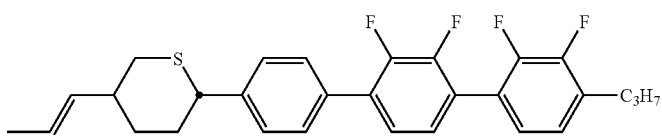
compound NO.231
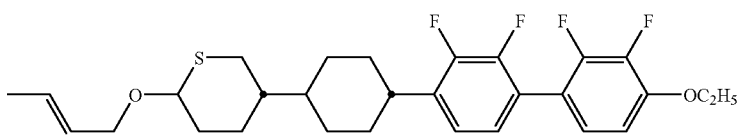
compound NO.232
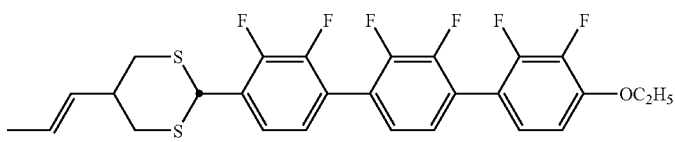
compound NO.233
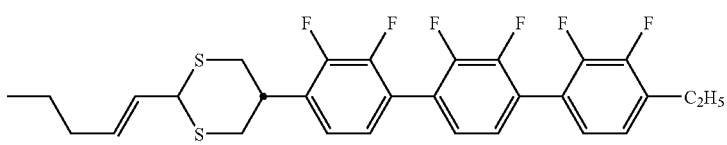

| | |
|---|---|
| compound NO.234 | 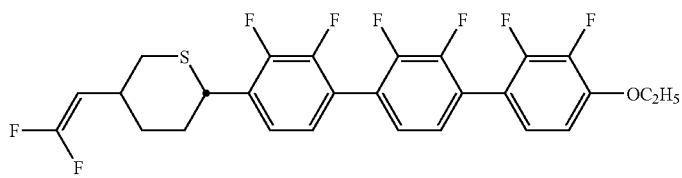 |
| compound NO.235 | 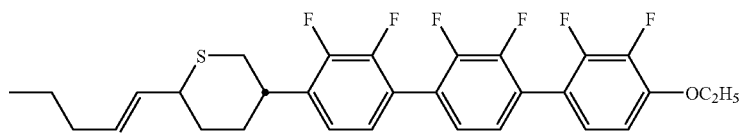 |
| compound NO.236 | 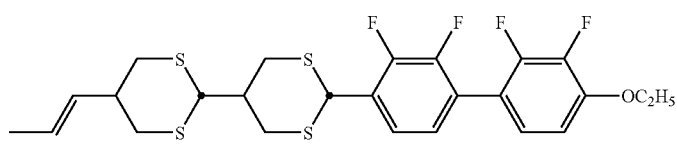 |
| compound NO.237 | 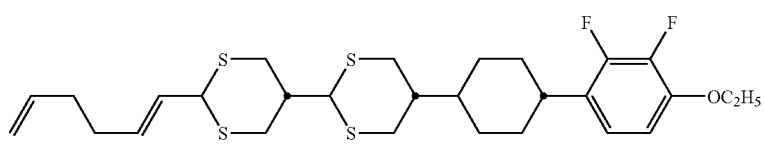 |
| compound NO.238 | 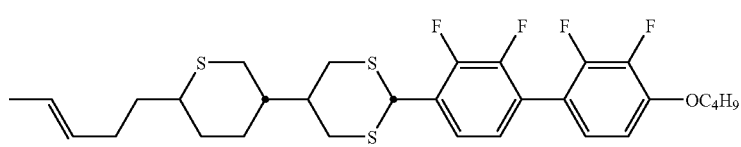 |
| compound NO.239 | 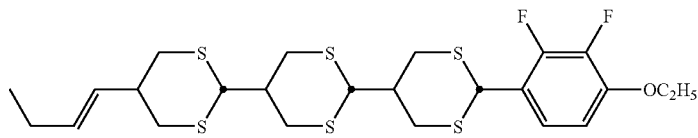 |
| compound NO.240 | 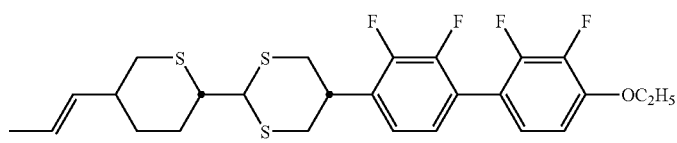 |
| compound NO.241 | 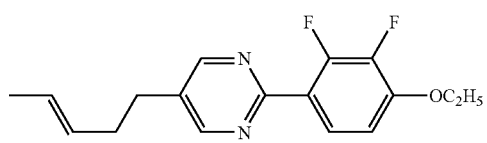 |
| compound NO.242 | 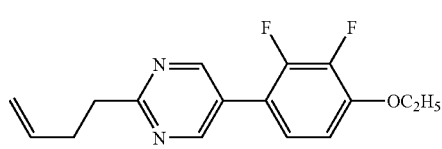 |
| compound NO.243 |  | compound NO.244 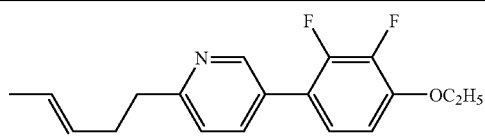
compound NO.245 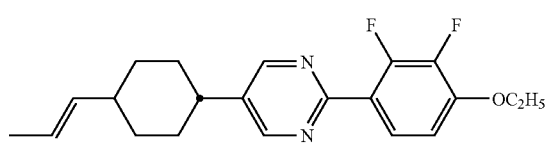
compound NO.246 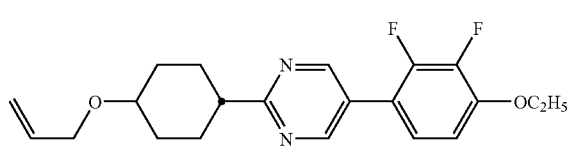
compound NO.247 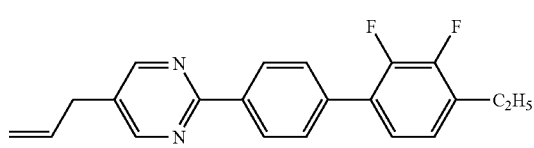
compound NO.248 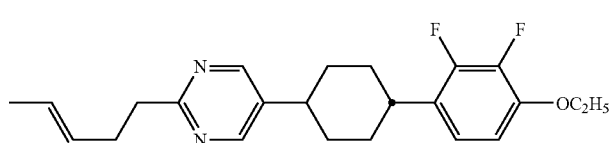
compound NO.249 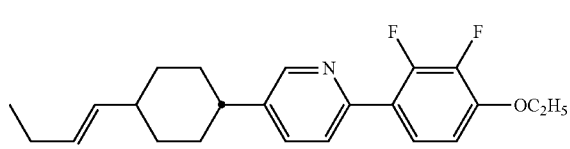
compound NO.250 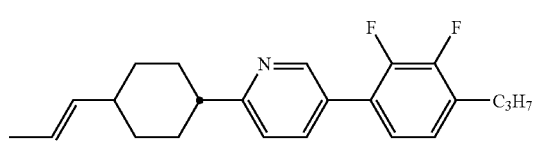
compound NO.251 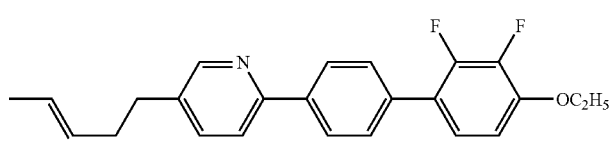
compound NO.252 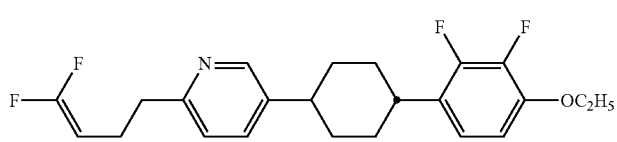
compound NO.253 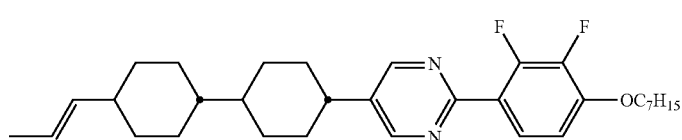
compound NO.254 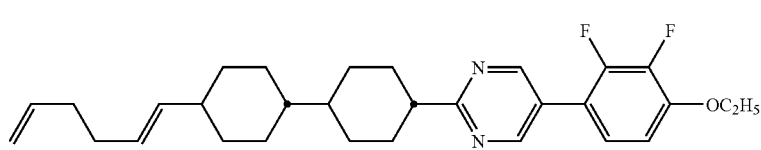

compound NO.255 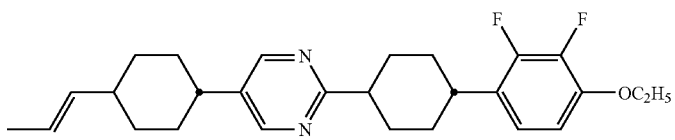
compound NO.256 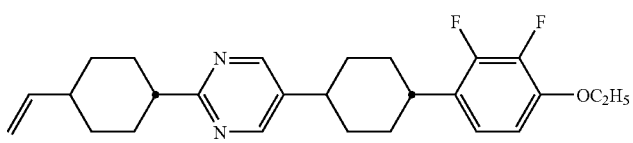
compound NO.257 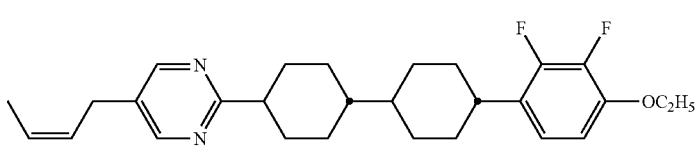
compound NO.258 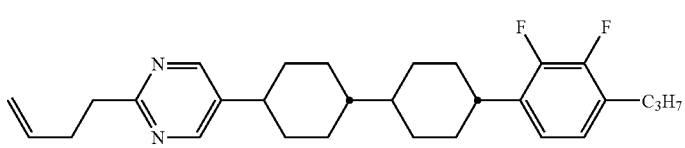
compound NO.259 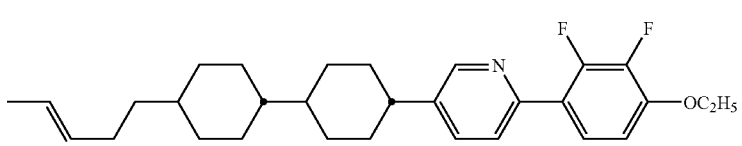
compound NO.260 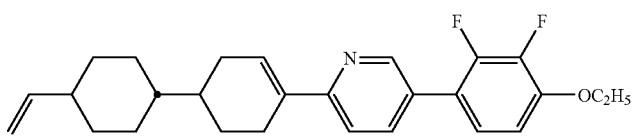
compound NO.261 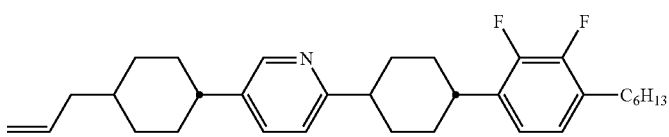
compound NO.262 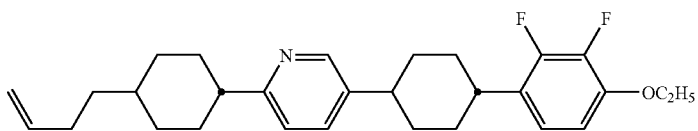
compound NO.263 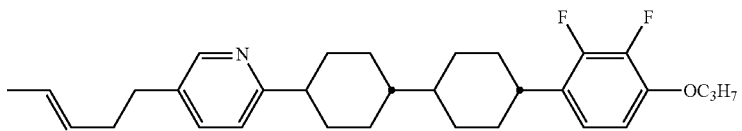
compound NO.264 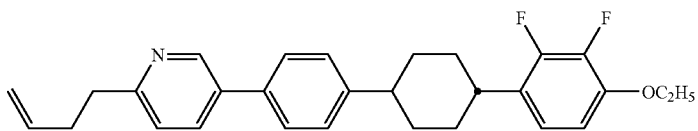
compound NO.265 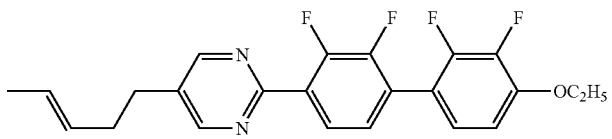

compound NO.266
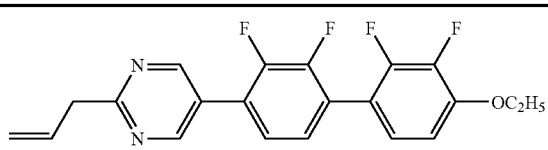
compound NO.267
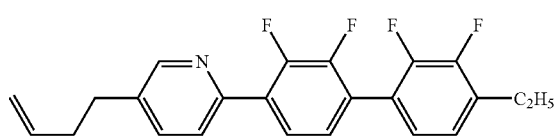
compound NO.268
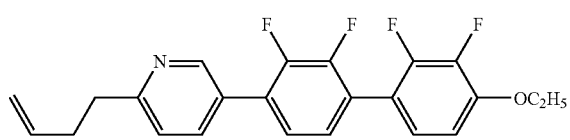
compound NO.269
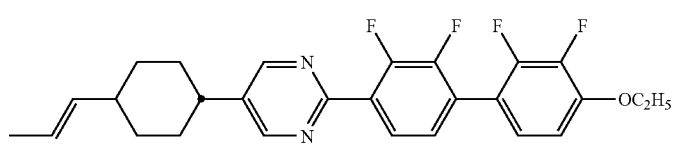
compound NO.270
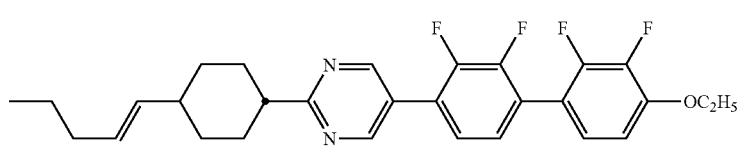
compound NO.271
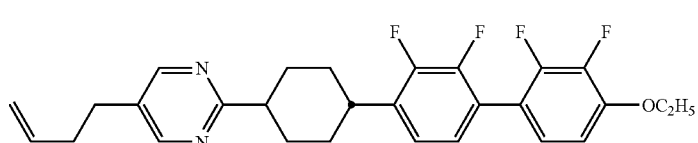
compound NO.272
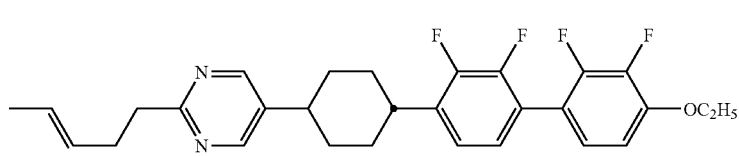
compound NO.273
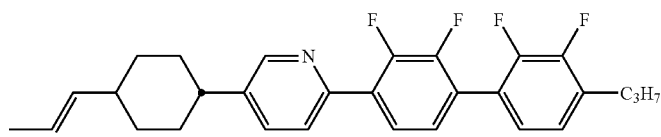
compound NO.274
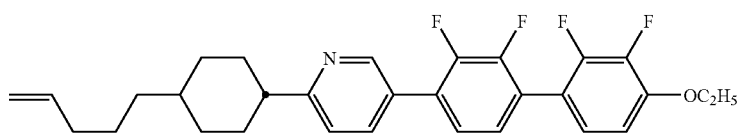
compound NO.275
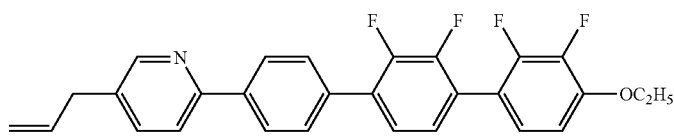
compound NO.276
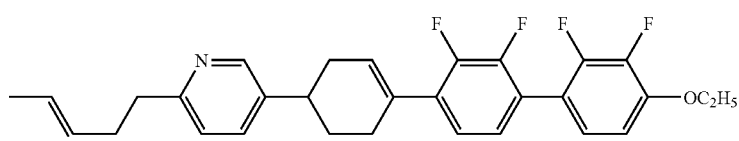

compound NO.277 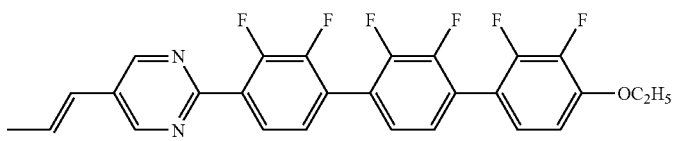
compound NO.278 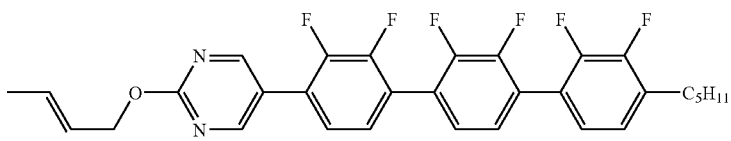
compound NO.279 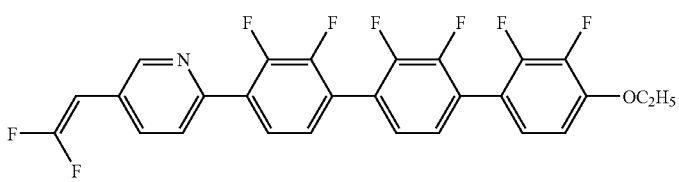
compound NO.280 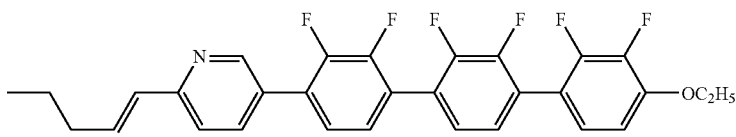
compound NO.281 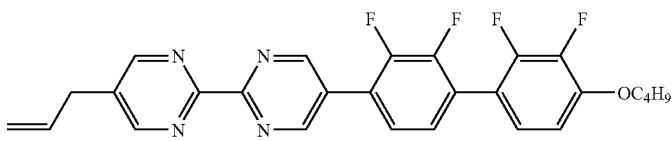
compound NO.282 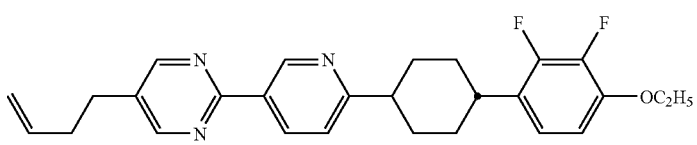
compound NO.283 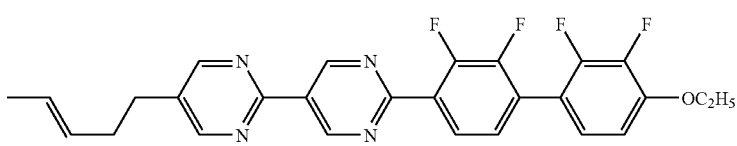
compound NO.284 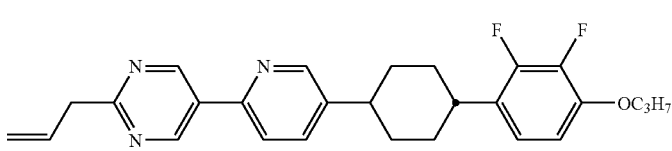
compound NO.285 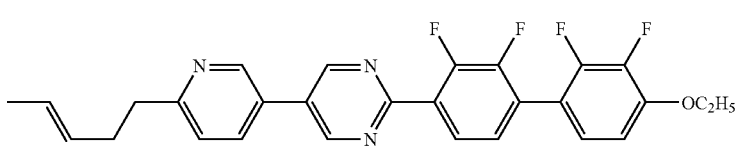
compound NO.286 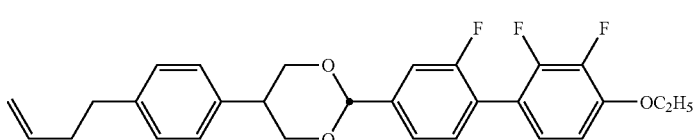

-continued
compound NO.287
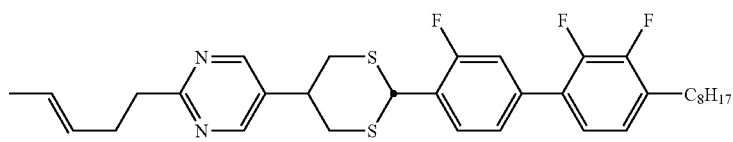
compound NO.288
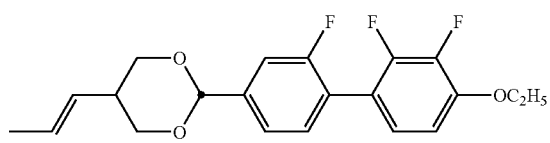
compound NO.289
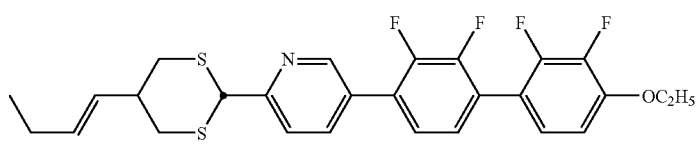
compound NO.290
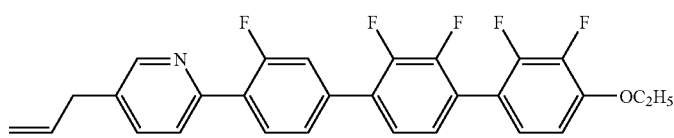
compound NO.291
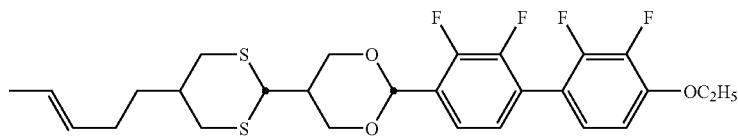
compound NO.292
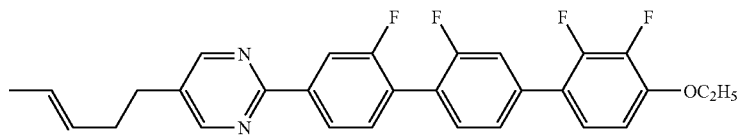
compound NO.293
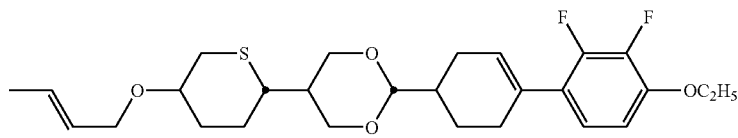
compound NO.294
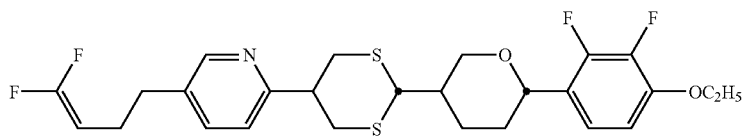
compound NO.295
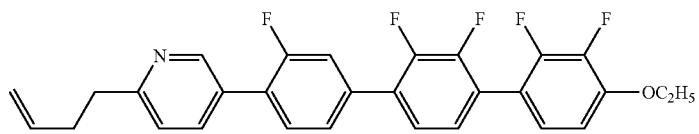
compound NO.296
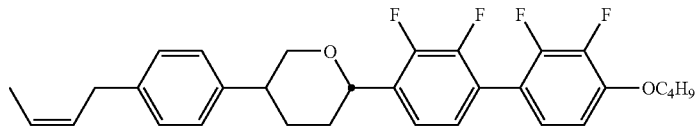
compound NO.297
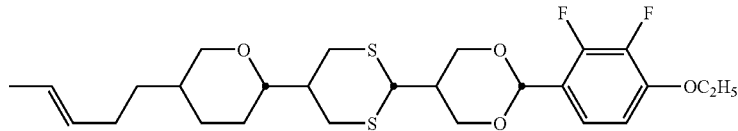

-continued
compound NO.298
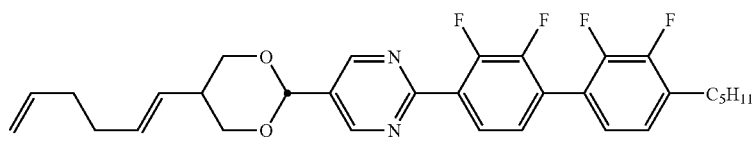
compound NO.299
compound NO.300
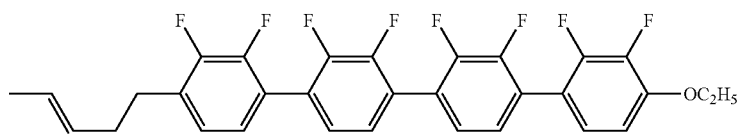
compound NO.301
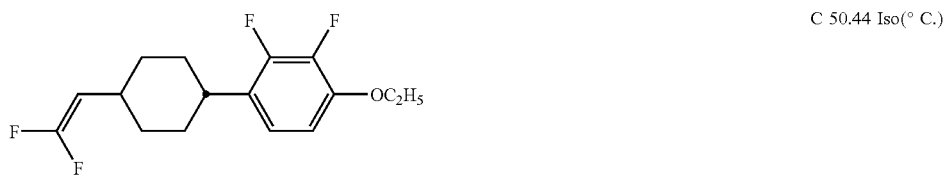
C 50.44 Iso(° C.)
compound NO.302
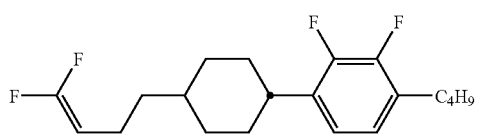
compound NO.303
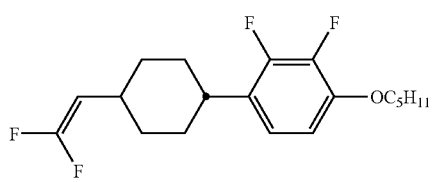
compound NO.304
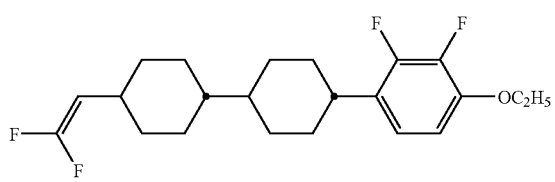
compound NO.305
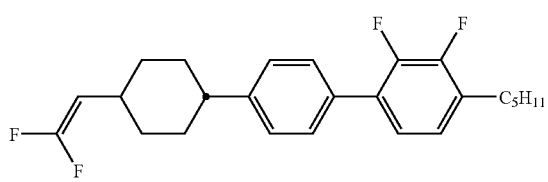
compound NO.306
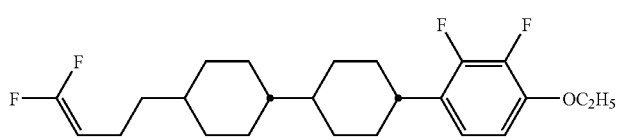

-continued
compound NO.307
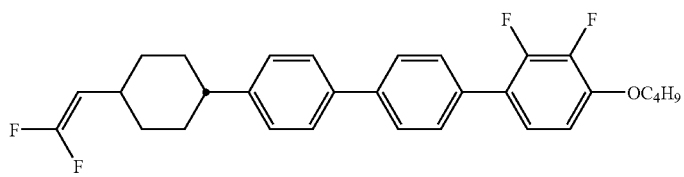
compound NO.308
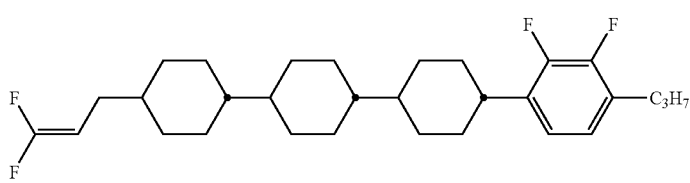
compound NO.309
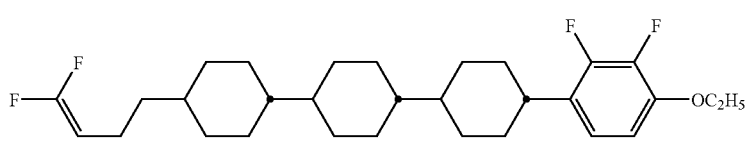
compound NO.310
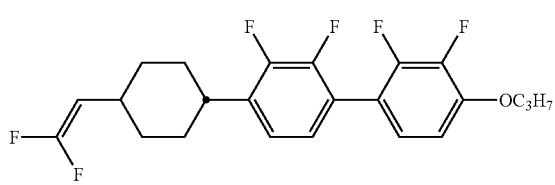
compound NO.311
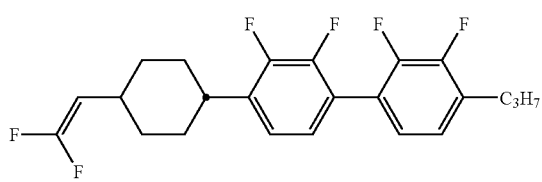
compound NO.312
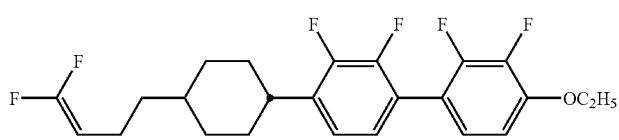
compound NO.313
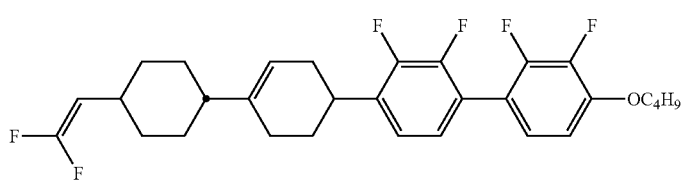
compound NO.314
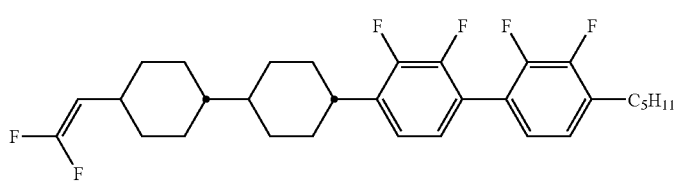
compound NO.315
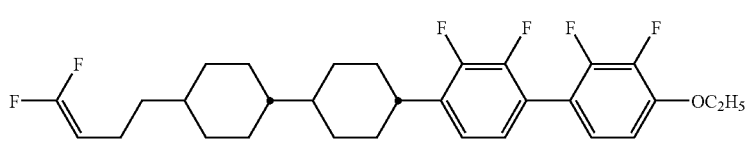

Examples of nematic liquid crystal compositions containing Examples of nematic liquid crystal compositions containing the liquid crystalline compounds of the present invention are shown below. In these example compositions, the notations of the compounds follow the definitions shown in Table 1, and their proportions are shown in terms of percent by weight.

Viscosity (η) was measured at 20.0° C., and refraction index of anisotropy (Δn), value of dielectric anisotropy (Δε), threshold voltage (Vth), and twist pitch (P) were measured at 25.0° C.

Neither appearance of the smectic phase nor precipitation of crystals was observed in any of the following compounds, even after the compounds were allowed to stand for 40 days in a freezer at a temperature of −20° C.

TABLE 1

Description method of compounds using marks.
R—(A$_1$)—Z$_1$— - - - —Z$_n$—(A$_n$)—X

| 1) Left end groups R— | Marks |
|---|---|
| C$_n$H$_{2n+1}$— | n- |
| C$_n$H$_{2n+1}$O— | nO— |
| C$_n$H$_{2n+1}$OC$_m$H$_{2m}$— | nOm- |
| CH$_2$=CH— | V- |
| CH$_2$=CHC$_n$H$_{2n}$— | Vn- |
| C$_n$H$_{2n+1}$CH=CHC$_m$H$_{2m}$— | nVm- |
| C$_n$H$_{2n+1}$CH=CHC$_m$H$_{2m}$CH=CHC$_k$H$_{2k}$— | nVmVk- |
| CF$_2$=CH— | VFF- |

| 2) Ring structures —(A$_1$)—, —(A$_n$)— | Marks |
|---|---|
|  | B |
| 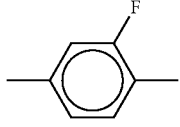 | B(F) |
| 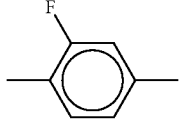 | B(2F) |
| 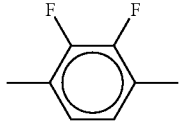 | B(2F,3F) |
| 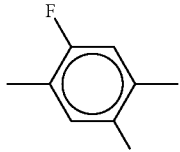 | B(2F,5F) |
| 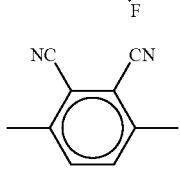 | B(2CN,3CN) |

TABLE 1-continued

Description method of compounds using marks.
R—(A$_1$)—Z$_1$— - - - —Z$_n$—(A$_n$)—X

| | |
|---|---|
| 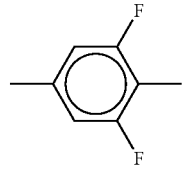 | B(F,F) |
| 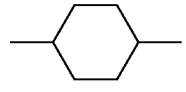 | H |
| 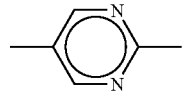 | Py |
| 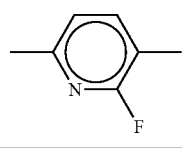 | Pr(F) |

| 3) Bonding groups —Z$_1$—, —Z$_n$— | Marks |
|---|---|
| —C$_2$H$_4$— | 2 |
| —C$_4$H$_8$— | 4 |
| —COO— | E |
| —C≡C— | T |
| —CH=CH— | V |
| —CF$_2$O— | CF2O |
| —OCF$_2$— | OCF2 |

| 4) Right end groups —X— | Marks |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —C$_n$H$_{2n+1}$ | -n |
| —OC$_n$H$_{2n+1}$ | —On |
| —COOCH$_3$ | —EMe |
| —C$_n$H$_{2n}$CH=CH$_2$ | -n V |
| —C$_m$H$_{2m}$CH=CHC$_n$H$_{2n+1}$ | -mVn |
| —C$_m$H$_{2m}$CH=CHC$_n$H$_{2n}$F | -mVnF |
| —CH=CF$_2$ | -VFF |
| —C$_n$H$_{2n}$CH=CF$_2$ | -nVFF |

5) Examples of description

Example 1 3-H2B(F,F)B(F)-F

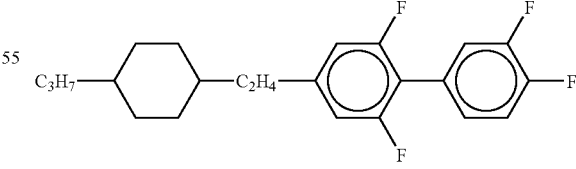

Example 2 3-HB(F)TB-2

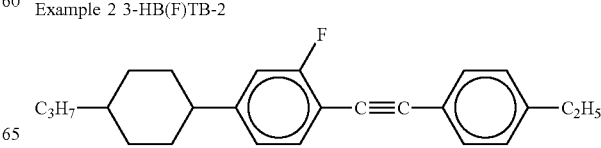

TABLE 1-continued

Description method of compounds using marks.
R—(A₁)—Z₁— - - - —Zₙ—(Aₙ)—X

Example 3  1V2-BEB(F,F)-C

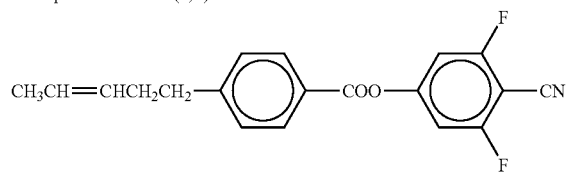

Example 2

Composition Example 1

| | | |
|---|---|---|
| V-HB(2F,3F)-O2 | (No. 6) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 60.0$ (° C.)
$\eta = 20.0$ (mPa · C.)
$\Delta n = 0.085$
$\Delta \epsilon = -2.0$

Example 3

Composition Example 2

| | | |
|---|---|---|
| V2-HB(2F,3F)-O2 | (No. 8) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 64.0$ (° C.)
$\eta = 20.1$ (mPa · s)
$\Delta n = 0.086$
$\Delta \epsilon = -2.1$

Example 4

Composition Example 3

| | | |
|---|---|---|
| V-HB(2F,3F)-O3 | (No. 11) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 58.6$ (° C.)
$\eta = 20.1$ (mPa · s)
$\Delta n = 0.082$
$\Delta \epsilon = -2.0$

Example 5

Composition Example 4

| | | |
|---|---|---|
| V-HHB(2F,3F)-O1 | (No. 31) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 82.1$ (° C.)
$\eta = 22.4$ (mPa · s)
$\Delta n = 0.090$
$\Delta \epsilon = -2.1$

Example 6

Composition Example 5

| | | |
|---|---|---|
| V2-HHB(2F,3F)-O1 | (No. 33) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 83.3$ (° C.)
$\eta = 22.0$ (mpa · s)
$\Delta n = 0.089$
$\Delta \epsilon = -2.0$

Example 7

Composition Example 6

| | | |
|---|---|---|
| V-HHB(2F,3F)-O2 | (No. 36) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 84.7$ (° C.)
$\eta = 21.7$ (mPa · s)
$\Delta n = 0.092$
$\Delta \epsilon = -2.0$

Example 8

Composition Example 7

| | | |
|---|---|---|
| V2-HHB(2F,3F)-O2 | (No. 38) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |

$T_{NI} = 87.1$ (° C.)
$\eta = 21.4$ (mPa · s)
$\Delta n = 0.092$
$\Delta \epsilon = -1.7$

Example 9

Composition Example 8

| | | |
|---|---|---|
| VFF-HB(2F,3F)-O2 | (No. 301) | 15.0% |
| 3-HEB-O2 | | 12.9% |
| 3-HEB-O4 | | 20.7% |
| 4-HEB-O2 | | 15.5% |
| 5-HEB-O1 | | 15.5% |
| 3-HEB-O2 | | 10.4% |
| $T_{NI}$ = 62.0 (° C.) | | |
| $\eta$ = 21.3 (mpa · s) | | |
| $\Delta n$ = 0.084 | | |
| $\Delta \epsilon$ = −1.9 | | |

Example 10

Composition Example 9

| | | |
|---|---|---|
| V2-HB(2F,3F)-O2 | (No. 8) | 14.0% |
| V2-HHB (2F, 3F)-O1 | (No. 33) | 14.0% |
| 4-HEB-O2 | | 20.0% |
| 5-HEB-O1 | | 20.0% |
| 3-HEB-O2 | | 18.0% |
| 5-HEB-O2 | | 14.0% |
| $T_{NI}$ = 79.7 (° C.) | | |
| $\eta$ = 22.7 (mPa · s) | | |
| $\Delta n$ = 0.097 | | |
| $\Delta \epsilon$ = −2.5 | | |

Example 11

Composition Example 10

| | | |
|---|---|---|
| V-HB(2F,3F)-O3 | (No. 11) | 8.0% |
| V2-HB(2F,3F)-O2 | (No. 8) | 8.0% |
| V2-HHB(2F,3F)-O2 | (No. 38) | 8.0% |
| 3-HH-2 | | 5.0% |
| 3-HH-4 | | 6.0% |
| 3-HH-O1 | | 4.0% |
| 3-HH-O3 | | 5.0% |
| 5-HH-O1 | | 4.0% |
| 3-HB(2F,3F)-O2 | | 12.0% |
| 5-HB(2F,3F)-O2 | | 11.0% |
| 3-HHB(2F,3F)-O2 | | 14.0% |
| 5-HHB(2F,3F)-O2 | | 15.0% |
| $T_{NI}$ = 71.7 (° C.) | | |
| $\Delta n$ = 0.079 | | |
| $\Delta \epsilon$ = −4.4 | | |

Example 12

Composition Example 11

| | | |
|---|---|---|
| V-HHB(2F,3F)-O1 | (No. 31) | 4.0% |
| V-HHB(2F,3F)-O2 | (No. 36) | 4.0% |
| 3-HH-4 | | 5.0% |
| 3-HH-5 | | 5.0% |
| 3-HH-O1 | | 6.0% |
| 3-HH-O3 | | 6.0% |
| 3-HB-O1 | | 5.0% |
| 3-HB-O2 | | 5.0% |
| 3-HB(2F,3F)-O2 | | 10.0% |
| 5-HB(2F,3F)-O2 | | 10.0% |
| 3-HHB(2F,3F)-O2 | | 12.0% |
| 5-HHB(2F,3F)-O2 | | 13.0% |
| 3-HHEH-3 | | 5.0% |
| 3-HHEH-5 | | 5.0% |
| 4-HHEH-3 | | 5.0% |
| $T_{NI}$ = 89.1 (° C). | | |
| $\Delta n$ = 0.079 | | |
| $\Delta \epsilon$ = −3.3 | | |

Example 13

Composition Example 12

| | | |
|---|---|---|
| V-HHB(2F,3F)-O1 | (No. 31) | 4.0% |
| 3-BB(2F,3F)-O2 | | 12.0% |
| 3-BB(2F,3F)-O4 | | 10.0% |
| 5-BB(2F,3F)-O4 | | 10.0% |
| 2-BB(2F,3F)B-3 | | 25.0% |
| 3-BB(2F,3F)B-5 | | 13.0% |
| 5-BB(2F,3F)B-5 | | 14.0% |
| 5-BB(2F,3F)B-7 | | 12.0% |
| $T_{NI}$ = 73.9 (° C.) | | |
| $\Delta n$ = 0.194 | | |
| $\Delta \epsilon$ = −3.5 | | |

Example 14

Composition Example 13

| | | |
|---|---|---|
| V-HB(2F,3F)-O2 | (No. 6) | 6.0% |
| 3-BB(2F,3F)-O2 | | 10.0% |
| 5-BB-5 | | 9.0% |
| 5-BB-O6 | | 9.0% |
| 5-BB-O8 | | 8.0% |
| 3-BEB-5 | | 6.0% |
| 5-BEB-5 | | 3.0% |
| 3-HEB-O2 | | 20.0% |
| 5-BBB(2F,3F)-7 | | 9.0% |
| 3-H2BB(2F)-5 | | 20.0% |
| $T_{NI}$ = 71.6 (° C.) | | |
| $\Delta n$ = 0.146 | | |
| $\Delta \epsilon$ = −3.3 | | |

Example 15

Composition Example 14

| | | |
|---|---|---|
| V-HB(2F,3F)-O3 | (No. 11) | 5.0% |
| V2-HB(2F,3F)-O2 | (No. 8) | 5.0% |
| V-HHB(2F,3F)-O2 | (No. 36) | 5.0% |
| 3-HB-O2 | | 6.0% |

-continued

| | | |
|---|---|---|
| 3-HEB(2F,3F)-O2 | | 9.0% |
| 4-HEB(2F,3F)-O2 | | 9.0% |
| 5-HEB(2F,3F)-O2 | | 9.0% |
| 2-BB2B-O2 | | 6.0% |
| 3-BB2B-O2 | | 6.0% |
| 5-BB2B-O1 | | 6.0% |
| 5-BB2B-O2 | | 6.0% |
| 1-B2BB(2F)-5 | | 7.0% |
| 3-B2BB(2F)-5 | | 7.0% |
| 5-B(F)BB-O2 | | 7.0% |
| 3-BB(2F,3F)B-3 | | 7.0% |

$T_{NI} = 81.6$ (° C.)
$\eta = 29.0$ (mPa · s)
$\Delta n = 0.162$
$\Delta \epsilon = -2.7$

Example 16

Composition Example 15

| | | |
|---|---|---|
| V2-HB(2F,3F)-O2 | (No. 8) | 9.0% |
| V-HHB(2F,3F)-O2 | (No. 36) | 9.0% |
| 3-HB-O2 | | 9.0% |
| 2-BTB-O1 | | 5.0% |
| 1-BTB-O2 | | 5.0% |
| 3-BTB(2F,3F)-O2 | | 13.0% |
| 5-BTB(2F,3F)-O2 | | 13.0% |
| 3-B(2F,3F)TB(2F,3F)-O4 | | 4.0% |
| 5-B(2F,3F)TB(2F,3F)-O4 | | 4.0% |
| 3-HBTB-O1 | | 5.0% |
| 3-HBTB-O2 | | 5.0% |
| 3-HBTB-O3 | | 5.0% |
| 3-HHB(2F,3F)-O2 | | 6.0% |
| 5-HBB(2F,3F)-O2 | | 5.0% |
| 5-BPr(F)-O2 | | 3.0% |

$T_{NI} = 95.0$ (° C.)
$\eta = 30.2$ (mpa · s)
$\Delta n = 0.223$

Example 17

Composition Example 16

| | | |
|---|---|---|
| V-HB(2F,3F)-O3 | (No. 11) | 10.0% |
| V2-HB(2F,3F)-O2 | (No. 8) | 6.0% |
| V-HHB(2F,3F)-O1 | (No. 31) | 5.0% |
| V2-HHB(2F,3F)-O1 | (No. 33) | 6.0% |
| V2-HHB(2F,3F)-O2 | (No. 38) | 6.0% |
| 3-HB-O2 | | 4.0% |
| 5-HB-3 | | 8.0% |
| 5-BB(2F,3F)-O2 | | 10.0% |
| 5-HB(2F,3F)-O2 | | 8.0% |
| 5-HHB(2F,3F)-O2 | | 4.0% |
| 5-HHB(2F,3F)-1O1 | | 4.0% |
| 3-HHB(2F,3F)-1 | | 5.0% |
| 3-HBB-2 | | 6.0% |
| 3-BB(2F,3F)B-3 | | 8.0% |
| 5-B2BB(2F,3F)-O2 | | 10.0% |

$T_{NI} = 72.3$ (° C.)
$\Delta n = 0.128$
$\Delta \epsilon = -4.2$

Example 18

Composition Example 17

| | | |
|---|---|---|
| V-HB(2F,3F)-O2 | (No. 6) | 9.0% |
| V-HHB(2F,3F)-O2 | (No. 36) | 3.0% |
| V2-HHB(2F,3F)-O1 | (No. 33) | 3.0% |
| V2-HHB(2F,3F)-O2 | (No. 38) | 7.0% |
| 3-HB-O2 | | 20.0% |
| 1O1-HH-3 | | 6.0% |
| 1O1-HH-5 | | 5.0% |
| 3-HH-EMe | | 12.0% |
| 5-HEB-O1 | | 8.0% |
| 3-HHB-1 | | 6.0% |
| 3-HHB-3 | | 6.0% |
| 3-HEB(2CN,3CN)-O5 | | 4.0% |
| 4-HEB(2CN,3CN)-O5 | | 3.0% |
| 5-HEB(2CN,3CN)-O5 | | 2.0% |
| 2-HBEB(2CN,3CN)-O2 | | 2.0% |
| 4-HBEB(2CN,3CN)-O4 | | 4.0% |

$T_{NI} = 75.8$ (° C.)
$\eta = 33.2$ (mPa · s)
$\Delta n = 0.087$
$\Delta \epsilon = -6.3$

Example 19

Composition Example 18

| | | |
|---|---|---|
| V-HB(2F,3F)-O2 | (No. 6) | 5.0% |
| V2-HHB(2F,3F)-O2 | (No. 38) | 3.0% |
| 1V2-BEB(F,F)-C | | 5.0% |
| 3-HB-C | | 20.0% |
| V2-HB-C | | 6.0% |
| 2-BTB-1 | | 10.0% |
| 1O1-HH-3 | | 3.0% |
| 3-HH-4 | | 11.0% |
| 3-HHB-1 | | 11.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 5.0% |
| 3-HHB-C | | 3.0% |

$T_{NI} = 89.0$ (° C.)
$\eta = 17.3$ (mPa · s)
$\Delta n = 0.154$
$\Delta \epsilon = 6.7$
$V_{th} = 2.19$ (V)

The pitch of the composition produced by adding 0.8 part by weight of an optically active compound CM33 to 100 parts by weight of the above composition was, P=11.3 μm.

Example 20

Composition Example 19

| | | |
|---|---|---|
| V-HHB(2F,3F)-O1 | (No. 31) | 3.0% |
| V-HHB(2F,3F)-O2 | (No. 36) | 3.0% |
| 2O1-BEB(F)-C | | 5.0% |
| 3O1-BEB(F)-C | | 12.0% |
| 5O1-BEB(F)-C | | 4.0% |
| 1V2-BEB(F,F)-C | | 10.0% |
| 3-HEB-O4 | | 4.0% |
| 3-HH-EMe | | 6.0% |
| 3-HB-O2 | | 18.0% |

-continued

| | | |
|---|---|---|
| 7-HEB-F | | 2.0% |
| 7-HHEB-F | | 2.0% |
| 5-HHEB-F | | 2.0% |
| 3-HBEB-F | | 4.0% |
| 2O1-HBEB(F)-C | | 2.0% |
| 3-HB(F)EB(F)-C | | 2.0% |
| 3-HBEB(F,F)-C | | 2.0% |
| 3-HHB-F | | 4.0% |
| 3-HHB-O1 | | 4.0% |
| 3-HHB-3 | | 3.0% |
| 3-HEBEB-F | | 2.0% |
| 3-HEBEB-1 | | 2.0% |
| 3-HHB(F)-C | | 4.0% |

$T_{NI} = 76.4$ (° C.)
$\eta = 38.0$ (mPa · s)
$\Delta n = 0.117$
$\Delta \epsilon = 23.9$
$V_{th} = 1.12$ (V)

Example 21

Composition Example 20

| | | |
|---|---|---|
| V-HB(2F,3F)-O2 | (No. 6) | 5.0% |
| V-HB(2F,3F)-O3 | (No. 11) | 5.0% |
| V-HHB(2F,3F)-O1 | (No. 31) | 4.0% |
| V2-HHB(2F,3F)-O1 | (No. 33) | 4.0% |
| 1V2-BEB(F,F)-C | | 6.0% |
| 3-HB-C | | 18.0% |
| 2-BTB-1 | | 10.0% |
| 5-HH-VFF | | 20.0% |
| 1-BHH-VFF | | 8.0% |
| 1-BHH-2VFF | | 11.0% |
| 3-H2BTB-2 | | 5.0% |
| 3-HHB-1 | | 4.0% |

$T_{NI} = 71.8$ (° C.)
$\eta = 16.8$ (mPa · s)
$\Delta n = 0.123$
$\Delta \epsilon = 5.3$
$V_{th} = 2.51$ (V)

Example 22

Composition Example 21

| | | |
|---|---|---|
| V2-HHB(2F,3F)-O2 | (No. 38) | 10.0% |
| 5-HB-F | | 12.0% |
| 6-HB-F | | 9.0% |
| 7-HB-F | | 7.0% |
| 2-HHB-OCF3 | | 7.0% |
| 3-HRB-OCF3 | | 7.0% |
| 4-HHB-OCF3 | | 7.0% |
| 5-HHB-OCF3 | | 5.0% |
| 3-HH2B-OCF3 | | 4.0% |
| 5-HH2B-OCF3 | | 4.0% |
| 3-HHB(F,F)-OCF3 | | 5.0% |
| 3-HBB(F)-F | | 10.0% |
| 3-HH2B(F)-F | | 3.0% |
| 3-HB(F) BH-3 | | 3.0% |
| 5-HBBH-3 | | 3.0% |
| 3-HHB(F,F)-OCF2H | | 4.0% |

$T_{NI} = 92.1$ (° C.)
$\eta = 15.8$ (mPa · s)
$\Delta n = 0.091$
$\Delta \epsilon = 3.3$
$V_{th} = 2.73$ (V)

Example 23

Composition Example 22

| | | |
|---|---|---|
| V-HHB(2F,3F)-O2 | (No. 36) | 5.0% |
| 7-HB(F,F)-F | | 5.0% |
| 3-H2HB(F,F)-F | | 12.0% |
| 4-H2HB(F,F)-F | | 6.0% |
| 3-HHB(F,F)-F | | 10.0% |
| 3-HBB(F,F)-F | | 10.0% |
| 3-HHEB(F,F)-F | | 10.0% |
| 4-HHEB(F,F)-F | | 3.0% |
| 5-HHEB(F,F)-F | | 3.0% |
| 2-HBEB(F,F)-F | | 3.0% |
| 3-HBEB(F,F)-F | | 5.0% |
| 5-HBEB(F,F)-F | | 3.0% |
| 3-HGB(F,F)-F | | 15.0% |
| 3-HBCF2OB(F,F)-F | | 4.0% |
| 3-HHBB(F,F)-F | | 6.0% |

$T_{NI} = 80.1$ (° C.)
$\eta = 33.6$ (mPa · s)
$\Delta n = 0.087$
$\Delta \epsilon = 12.8$
$V_{th} = 1.51$ (V)

The pitch of the composition produced by adding 0.3 part by weight of an optically active compound CN to 100 parts by weight of the above composition was, P=77.0 μm.

Example 24

Composition Example 23

| | | |
|---|---|---|
| V-HHB(2F,3F)-O1 | (No. 31) | 5.0% |
| V2-HHB(2F,3F)-O1 | (No. 33) | 5.0% |
| 2-HHB(F)-F | | 2.0% |
| 3-HHB(F)-F | | 2.0% |
| 5-HHB(F)-F | | 2.0% |
| 2-HBB(F)-F | | 6.0% |
| 3-HBB(F)-F | | 6.0% |
| 2-H2BB(F)-F | | 9.0% |
| 3-H2BB(F)-F | | 9.0% |
| 3-HBB(F,F)-F | | 25.0% |
| 5-HBB(F,F)-F | | 19.0% |
| 1O1-HBBH-4 | | 5.0% |
| 1O1-HBBH-5 | | 5.0% |

$T_{NI} = 101.0$ (° C.)
$\eta = 35.8$ (mPa · s)
$\Delta n = 0.134$
$\Delta \epsilon = 6.1$
$V_{th} = 2.17$ (V)

The pitch of the composition produced by adding 0.2 part by weight of an optically active compound CM43L to 100 parts by weight of the above composition was, P=77.7 μm.

Example 25

Composition Example 24

| | | |
|---|---|---|
| V-HB(2F,3F)-O3 | (No. 11) | 15.0% |
| V2-HB(2F,3F)-O2 | (No. 8) | 15.0% |
| V-HHB(2F,3F)-O1 | (No. 31) | 10.0% |

-continued

| | | |
|---|---|---|
| V2-HHB(2F,3F)-O1 | (No. 33) | 10.0% |
| V2-HHB(2F,3F)-O2 | (No. 38) | 10.0% |
| 3-HH-EMe | | 25.0% |
| 5-HH-EMe | | 15.0% |

Example 26

Composition Example 25

| | | |
|---|---|---|
| V-HB(2F,3F)-O3 | (No. 11) | 13.0% |
| V2-HB(2F,3F)-O2 | (No. 8) | 13.0% |
| V2-HHB(2F,3F)-O1 | (No. 33) | 10.0% |
| V2-HHB(2F,3F)-O2 | (No. 38) | 10.0% |
| 3-HH-EMe | | 20.0% |
| 5-HH-EMe | | 10.0% |
| 3-HH-4 | | 10.0% |
| 3-HB-O2 | | 5.0% |
| 3-HHB-1 | | 9.0% |

Example 27

Composition Example 26

| | | |
|---|---|---|
| V-HB(2F,3F)-O3 | (No. 11) | 12.0% |
| V2-HB(2F,3F)-O2 | (No. 8) | 12.0% |
| V-HHB(2F,3F)-O2 | (No. 31) | 8.0% |
| V2-HHB(2F,3F)-O1 | (No. 33) | 8.0% |
| 3-HH-EMe | | 12.0% |
| 5-HH-EMe | | 5.0% |
| 3-HEB-O2 | | 6.0% |
| 3-HEB-O4 | | 8.0% |
| 4-HEB-O2 | | 6.0% |
| 5-HEB-O1 | | 6.0% |
| 5-HEB-O2 | | 4.0% |
| 3-HHB-1 | | 13.0% |

INDUSTRIAL APPLICABILITY

As seen from the above examples, the compound of the present invention which has two to four rings with containing an alkenyl group and 2,3-difluorophenyl group, has the following features:
1) Exhibits a wide liquid crystal phase temperature range, as well as frequent appearance of the nematic phase;
2) Significantly improves response speeds and lowers driving voltages in IPS and VA systems because of large negative $\Delta\epsilon$ and low viscosity;
3) Increases $K_{33}/K_{11}$ values and decreases $\Delta\epsilon/\epsilon\perp$, improving the steepness of the V-T curve in the STN system; and
4) Stable nematic liquid crystal compositions can be prepared therefrom without the precipitation of crystals or the appearance of the smectic phase even at extremely low temperature.

The compound of the present invention exhibits the above features 1) through 4), and provides novel liquid crystal compositions and liquid crystal diaplay devices that are stable against under the outside environment, and that can realize expansion of the usable temperature range, low voltage driving, and high response speed.

The invention claimed is:

1. A liquid crystal composition comprising at least two components, characterized by containing at least one liquid crystalline compound represented by the following general formula (1):

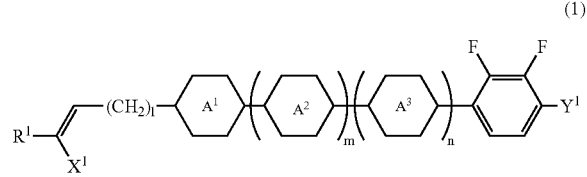

(1)

wherein
  $R^1$ represents hydrogen, fluorine, an alkyl group having 1 to 4 carbon atoms, or an alkenyl group having 2 to 4 carbon atoms;
  each of rings $A^1$, $A^2$ and $A^3$ independently represents trans-1,4-cyclohexylene group, 1,4-cyclohexenylene group, trans-1,4-silacyclohexylene group, 1,4-phenylene group, 2,3-difluoro-1,4-phenylene group, 2-fluoro-1,4-phenylene group, 3-fluoro-1,4-phenylene group, 1,3-dioxane-2,5-diyl group, tetrahydropyrane-2,5-diyl group, 1,3-dithiane-2,5-diyl group, or tetrahydro-thiopyrane-2,5-diyl group;
  $X^1$ represents hydrogen or fluorine;
  $Y^1$ represents hydrogen or an alkyl group having 1 to 10 carbon atoms, in which each of optional nonadjacent methylene groups ($-CH_2-$) may be substituted by oxygen; $\lambda$ represents an integer from 0 to 4, in which each of optional nonadjacent methylene groups in $(-CH_2-)_l$ may be substituted by oxygen; and
  each of m and n independently represents 0 or 1;
  with the proviso that when $Y^1$ represents ethoxy, one of m and n is 1 and the other is 0, $A^1$ represents trans-1,4-cyclohexylene, $A^2$ and $A^3$ are 2,3-difluoro-1,4-phenylene or 3-fluoro-1,4-phenylene, $X^1$ represents hydrogen, $\lambda$ is 0 or 2, then $R^1$ represents neither hydrogen nor methyl;
  when $Y^1$ represents ethoxy, one of m and n is 1 and the other is 0, $A^1$ represents trans-1,4-cylclohexylene, $A^2$ and $A^3$ are 2-fluoro-1,4-phenylene, $X^1$ represents hydrogen, $R^1$ represents methyl, then $\lambda$ is neither 0 nor 2; and
  when ring $A^1$ represents 1,4-phenylene group, 2,3-difluoro-1,4-phenylene group, 2-fluoro-1,4-phenylene, or 3-fluoro-1,4-phenylene group, $\lambda$ is 1 to 4.

2. A liquid crystalline compound represented by the following general formula (1):

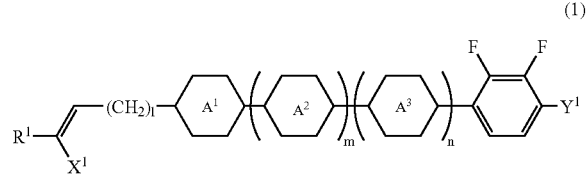

(1)

wherein
  $R^1$ represents hydrogen, fluorine, an alkyl group having 1 to 4 carbon atoms, or an alkenyl group having 2 to 4 carbon atoms;

each of rings $A^1$, $A^2$ and $A^3$ independently represents trans-1,4-cyclohexylene group, 1,4-cyclohexenylene group, trans-1,4-silacyclohexylene group, 1,4-phenylene group, 2,3-difluoro-1,4-phenylene group, 2-fluoro-1,4-phenylene group, 3-fluoro-1,4-phenylene group, 1,3-dioxane-2,5-diyl group, tetrahydropyrane-2,5-diyl group, 1,3-dithiane-2,5-diyl group, or tetrahydro-thiopyrane-2,5-diyl group;

$X^1$ hydrogen or fluorine;

$Y^1$ represents hydrogen or an alkyl group having 1 to 10 carbon atoms, in which each of optional nonadjacent methylene groups ($-CH_2-$) may be substituted by oxygen; $\Lambda$ represents an integer from 0 to 4, in which each of optional nonadjacent methylene groups in ($-CH_2-$), may be substituted by oxygen; and each of m and n independently represents 0 or 1;

with the proviso that when $Y^1$ represents ethoxy, one of m and n is 1 and the other is 0, $A^1$ represents trans-1,4-cyclohexylene, $A^2$ and $A^3$ are 2,3-difluoro-1,4-phenylene or 3-fluoro-1,4-phenylene, $X^1$ represents hydrogen, $\Lambda$ is 0 or 2, then $R^1$ represents neither hydrogen nor methyl;

when $Y^1$ represents ethoxy, one of m and n is 1 and the other is 0, $A^1$ represents trans-1,4-cylclohexylene, $A^2$ and $A^3$ are 2-fluoro-1,4-phenylene, $X^1$ represents hydrogen, $R^1$ represents methyl, then $\Lambda$ is neither 0 nor 2;

when both rings $A^1$ and $A^2$ represents 1,4-cyclohexylene, l is 2, m is 1, n is 0, both $R^1$ and $X^1$ represent hydrogen, then $Y^1$ represents hydrogen or an alkyl group having 2 to 10 carbon atoms, in which each of optional nonadjacent methylene groups ($-CH_2-$) may be substituted by oxygen; and when ring $A^1$ represents 1,4-phenylene group, 2,3-difluoro-1,4-phenylene group, 2-fluoro-1,4-phenylene group, or 3-fluoro-1,4-phenylene group, $\Lambda$ is 1 to 4.

3. A liquid crystalline compound according to claim 2, wherein each of the rings $A^1$ and $A^2$ in general formula (1) is independently trans-1,4-cyclohexylene, 2,3-difluoro-1,4-phenylene group or 1,3-dioxane-2,5-diyl group; m is 1; and n is 0.

4. A liquid crystal composition comprising at least one liquid crystalline compound according to claim 2 as a first component and at least one compound selected from a group consisting of compounds represented by the following general formulas (7), (8) and (9) as a second component;

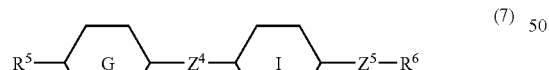

(7)

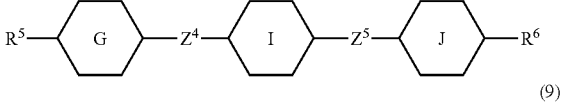

(8)

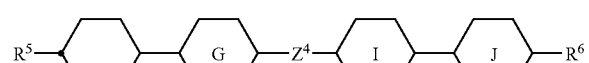

(9)

where
each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene may be substituted by fluorine;

each of rings G, I and J independently represents trans-1,4-cyclohexylene group, pyrimidine-2,5-diyl group or 1,4-phenylene group in which hydrogen may be substituted by fluorine; and each of $Z^4$ and $Z^5$ independently represents 1,2-ethylene group, vinylene group, $-COO-$, $-C\equiv C-$ or a single bond.

5. A liquid crystal composition comprising at least one liquid crystalline compound according to claims 2 as a first component; at least one compound selected from a group consisting of compounds represented by the following general formulas (7), (8) and (9):

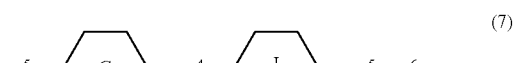

(7)

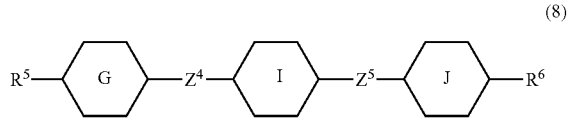

(8)

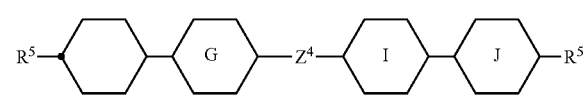

(9)

as a second component, where
each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene may be substituted by fluorine;

each of rings G, I and J independently represents trans-1,4-cyclohexylene group, pyrimidine-2,5-diyl group or 1,4-phenylene group in which hydrogen may be substituted by fluorine; and each of $Z^4$ and $Z^5$ independently represents 1,2-ethylene group, vinylene group, $-COO-$, $-C\equiv C-$ or a single bond; and at least one compound selected from a group consisting of compounds represented by the following general formulas (10), (11) and (12):

(10)

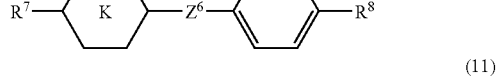

(11)

-continued

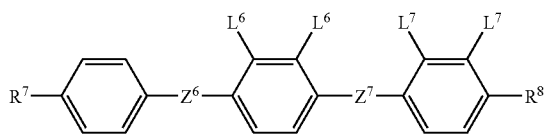
(12)

as a third component, where
each $R^7$ and $R^8$ independently represents an alkyl group having 1 to 10 carbon atoms, in which each of optional adjacent methylene groups may be substituted by oxygen or vinylene group, and in which each of optional hydrogen in these methylene groups may be substituted by fluorine;
each of rings K and M independently represents trans-1,4-cyclohexylene group or 1,4-phenylene group;
each $L^6$ and $L^7$ independently represents hydrogen or fluorine, but $L^6$ and $L^7$ are not both hydrogen simultaneously; and
each $Z^6$ and $Z^7$ independently represents —CH$_2$CH$_2$—, —CH$_2$— or a single bond.

6. A liquid crystal composition comprising at least one liquid crystalline compound according to claim 2 as a first component; at least one compound selected from a group consisting of compounds represented by the following general formulas (2), (3) and (4):

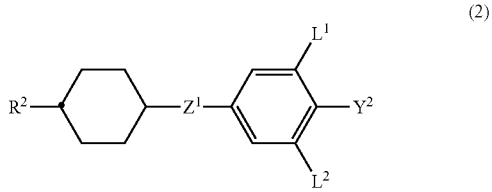
(2)

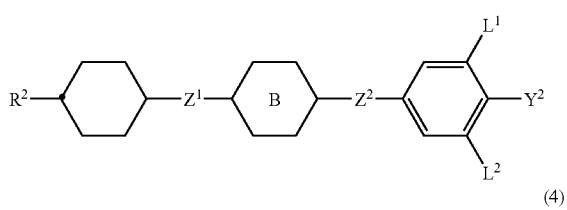
(3)

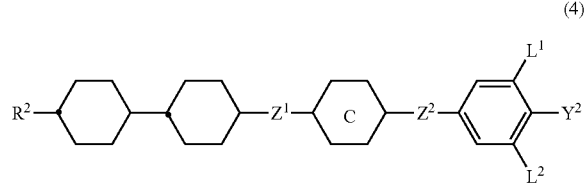
(4)

as a second component, where
$R^2$ represents an alkyl group having 1 to 10 carbon atoms, in which each of optional nonadjacent methylene groups may be substituted by oxygen or —CH═CH— group, and in which each of optional hydrogen in these methylene groups may be substituted by fluorine;
$Y^2$ represents fluorine, chlorine, —OCF$_3$, —OCF$_2$H, —CF$_3$, —CF$_2$H, —CFH$_2$, —OCF$_2$CF$_2$H or —OCF$_2$CFHCF$_3$;
each $L^1$ and $L^2$ independently represents hydrogen or fluorine; p1 each $Z^1$ and $Z^2$ independently represents 1,2-ethylene group, vinylene group, 1,4-butylene group, —COO—, —CF$_2$O—, —OCF$_2$ or a single bond;
ring B represents trans-1,4-cyclohexylene group, 1,3-dioxane-2,5-diyl group or 1,4-phenylene group, in which each of hydrogen may be substituted by fluorine; and
ring C represents trans-1,4-cyclohexylene group or 1,4-phenylene group, in which each of hydrogen may be substituted by fluorine; and
at least one compound selected from a group consisting of compounds represented by the following general formulas (7), (8) and (9):

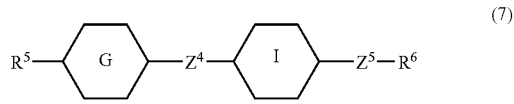
(7)

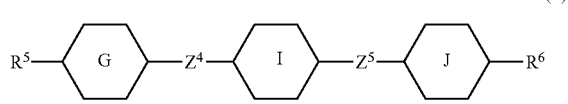
(8)

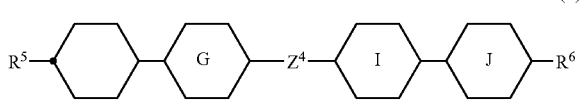
(9)

as a third component, where
each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene may be substituted by fluorine;
each of rings G, I and J independently represents trans-1,4-cyclohexylene group, pyrimidine-2,5-diyl group or 1,4-phenylene group in which hydrogen may be substituted by fluorine; and
each of $Z^4$ and $Z^5$ independently represents 1,2-ethylene group, vinylene group, —COO—, —C≡C— or a single bond.

7. A liquid crystal composition comprising at least one liquid crystalline compound according to claim 2 as a first component; at least one compound selected from a group consisting of compounds represented by the following general formulas (5) and (6):

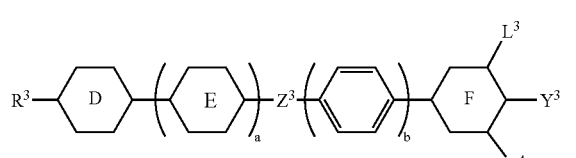
(5)

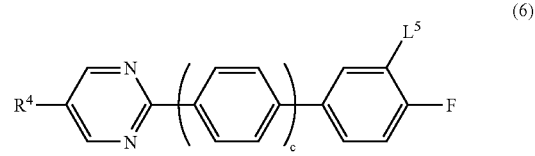
(6)

as a second component, where each of $R^3$ and $R^4$ independently represents an alkyl group having 1 to 10 carbon atoms, in which each of optional nonadjacent methylene groups may be substituted by oxygen or vinylene group, and in which each of optional hydrogen in these methylene groups may be substituted by fluorine;

$Y^3$ represents —CN or —C≡C—CN;

ring D represents trans-1,4-cyclohexylene group, 1,4-phenylene group, pyrimidine-2,5-diyl group or 1,3-dioxane-2,5-diyl group;

ring E represents trans-1,4-cyclohexylene group or 1,4-phenylene group, in which each of optional hydrogen may be substituted by fluorine or pyrimidine-2,5-diyl group;

ring F represents trans-1,4-cyclohexylene group or 1,4-phenylene group;

$Z^3$ represents 1,2-ethylene group, —COO— or a single bond;

each $L^3$, $L^4$ and $L^5$ independently represents hydrogen or fluorine; and each a, b and c independently represents 0 or 1; and at least one compound selected from a group consisting of compounds represented by the following general formulas (7), (8) and (9):

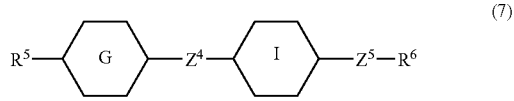
(7)

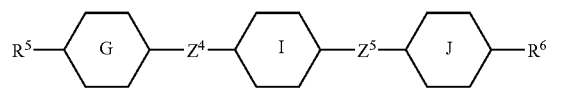
(8)

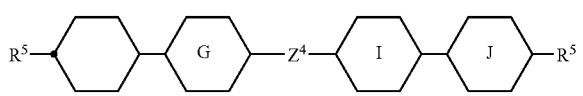
(9)

as a third component, where each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene may be substituted by fluorine;

each of rings G, I and J independently represents trans-1,4-cyclohexylene group, pyrimidine-2,5-diyl group or 1,4-phenylene group in which hydrogen may be substituted by fluorine; and each of $Z^4$ and $Z^5$ independently represents 1,2-ethylene group, vinylene group, —COO—, —C≡C— or a single bond.

8. A liquid crystal composition comprising at least one liquid crystalline compound according to claim 2 as a first component; at least one compound selected from a group consisting of compounds represented by the following general formulas (2), (3) and (4):

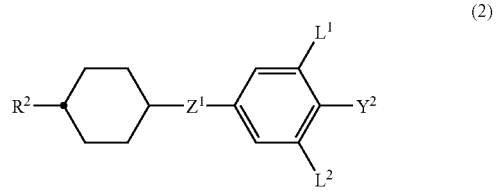
(2)

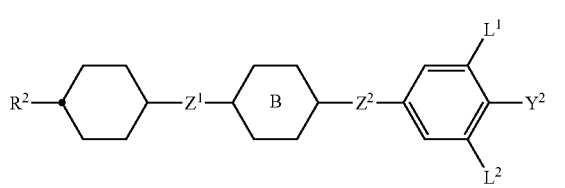
(3)

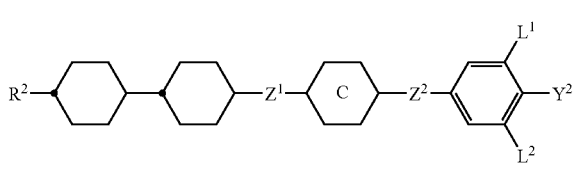
(4)

as a second component, where $R^2$ represents an alkyl group having 1 to 10 carbon atoms, in which each of optional nonadjacent methylene groups may be substituted by oxygen or —CH═CH— group, and in which each of optional hydrogen in these methylene groups may be substituted by fluorine;

$Y^2$ represents fluorine, chlorine, —OCF$_3$, —OCF$_2$H, —CF$_3$, —CF$_2$H, —CFH$_2$, —OCF$_2$CF$_2$H or —OCF$_2$CFHCF$_3$;

each $L^1$ and $L^2$ independently represents hydrogen or fluorine;

each $Z^1$ and $Z^2$ independently represents 1,2-ethylene group, vinylene group, 1,4-butylene group, —COO—, —CF$_2$O—, —OCF$_2$ or a single bond;

ring B represents trans-1,4-cyclohexylene group, 1,3-dioxane-2,5-diyl group or 1,4-phenylene group, in which each of hydrogen may be substituted by fluorine; and ring C represents trans-1,4-cyclohexylene group or 1,4-phenylene group, in which each of hydrogen may be substituted by fluorine;

at least one compound selected from a group consisting of compounds represented by the following general formulas (5) and (6):

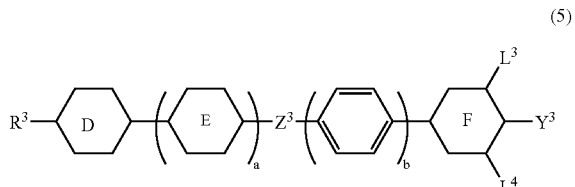
(5)

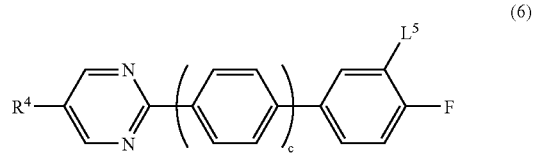
(6)

as a third component, where each of $R^3$ and $R^4$ independently represents an alkyl group having 1 to 10 carbon atoms, in which each of optional nonadjacent methylene groups may be substituted by oxygen or vinylene group, and in which each of optional hydrogen in these methylene groups may be substituted by fluorine;

$Y^3$ —CN or —C≡C—CN;

ring D represents trans-1,4-cyclohexylene group, 1,4-phenylene group, pyrimidine-2,5-diyl group or 1,3-dioxane-2,5-diyl group;

ring E represents trans-1,4-cyclohexylene group or 1,4-phenylene group, in which each of optional hydrogen may be substituted by fluorine or pyrimidine-2,5-diyl group;

ring F represents trans-1,4-cyclohexylene group or 1,4-phenylene group;

$Z^3$ represents 1,2-ethylene group, —COO— or a single bond;

each $L^3$, $L^4$ and $L^5$ independently represents hydrogen or fluorine; and each a, b and c independently represents 0 or 1; and at least one compound selected from a group consisting of compounds represented by the following general formulas (7), (8) and (9):

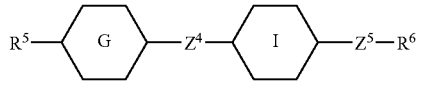
(7)

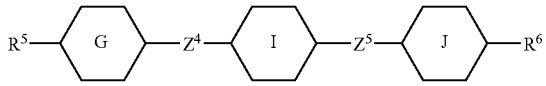
(8)

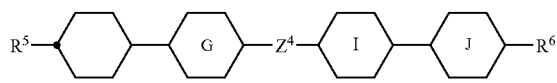
(9)

as a fourth component, where each of $R^5$ and $R^6$ independently represents an alkyl group having 1 to 10 carbon atoms, in which each of optional nonadjacent methylene groups may be substituted by oxygen or vinylene group and in which each of optional hydrogen in these methylene may be substituted by fluorine;

each of rings G, I and J independently represents trans-1,4-cyclohexylene group, pyrimidine-2,5-diyl group or 1,4-phenylene group in which hydrogen may be substituted by fluorine; and each of $Z^4$ and $Z^5$ independently represents 1,2-ethylene group, vinylene group, —COO—, —C≡C— or a single bond.

9. A liquid crystal composition according to claim 1 further comprising one or more optically active compounds.

10. A liquid crystal display device constituted from a liquid crystal composition according to claim 1.

* * * * *